(12) United States Patent
Chavan et al.

(10) Patent No.: US 10,874,339 B2
(45) Date of Patent: Dec. 29, 2020

(54) SYSTEM AND METHOD FOR MEASURING AN AMOUNT OF BLOOD AND/OR CLOTTING IN A POCKET SURROUNDING AN IMPLANTABLE MEDICAL DEVICE

(71) Applicant: Senseonics, Incorporated, Germantown, MD (US)

(72) Inventors: Abhi Chavan, Germantown, MD (US); James Masciotti, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 249 days.

(21) Appl. No.: 16/009,912

(22) Filed: Jun. 15, 2018

(65) Prior Publication Data

US 2018/0360355 A1    Dec. 20, 2018

Related U.S. Application Data

(60) Provisional application No. 62/520,088, filed on Jun. 15, 2017.

(51) Int. Cl.
| | | |
|---|---|---|
| *A61B 5/1455* | (2006.01) | |
| *A61B 5/1495* | (2006.01) | |
| *A61B 5/02* | (2006.01) | |
| *A61B 5/1459* | (2006.01) | |

(Continued)

(52) U.S. Cl.
CPC ........ *A61B 5/1495* (2013.01); *A61B 5/02042* (2013.01); *A61B 5/1459* (2013.01); *A61B 5/6861* (2013.01); *A61B 5/1451* (2013.01); *A61B 5/14532* (2013.01);

(Continued)

(58) Field of Classification Search
CPC . A61B 5/1455; A61B 5/1459; A61B 5/14556; A61B 5/14532; A61B 5/14546; A61B 5/6846; A61B 5/686; A61B 5/72
See application file for complete search history.

(56) References Cited

U.S. PATENT DOCUMENTS 6,216,022 B1 *  4/2001  Tyrrell ............... A61B 5/14532
                                                              600/310
8,073,548 B2   12/2011  Colvin, Jr. et al.
(Continued)

FOREIGN PATENT DOCUMENTS

WO    2016/059635 A1    4/2016

*Primary Examiner* — Eric F Winakur
(74) *Attorney, Agent, or Firm* — Rothwell, Figg, Ernst & Manbeck, P.C.

(57) ABSTRACT

A system and method for measuring an amount of blood and/or clotting in a pocket around an implantable device. The system may include a first light source configured to emit light over a first wavelength range. The system may include a first photodetector configured to output a first signal indicative of an amount of the first light received by the first photodetector. The system may include the implantable device and an external device. The implantable device may include one of the first light source and the first photodetector, and the external device may include the other of the first light source and the first photodetector. In some embodiments, the external device may include a controller configured to calculate the amount of blood/or clotting in the pocket around the implantable device using at least a measurement of the first signal.

22 Claims, 39 Drawing Sheets

(51) Int. Cl.
    *A61B 5/00*     (2006.01)
    *A61B 5/145*    (2006.01)
(52) U.S. Cl.
    CPC ... *A61B 5/14556* (2013.01); *A61B 2560/0276* (2013.01); *A61B 2562/0238* (2013.01)

(56) References Cited

U.S. PATENT DOCUMENTS

| | | |
|---|---|---|
| 8,320,983 B2 * | 11/2012 | Martini .............. A61B 5/14532 600/310 |
| 9,414,775 B2 | 8/2016 | Colvin, Jr. et al. |
| 9,427,182 B2 | 8/2016 | Emken et al. |
| 9,693,714 B2 | 7/2017 | DeHennis et al. |
| 2003/0050542 A1 | 3/2003 | Reihl et al. |
| 2003/0130570 A1 | 7/2003 | Krivitski et al. |
| 2012/0296189 A1 | 11/2012 | Bhogal et al. |
| 2013/0241745 A1 | 9/2013 | Colvin, Jr. et al. |
| 2014/0275869 A1 | 9/2014 | Kintz et al. |
| 2015/0077050 A1 | 3/2015 | Van Funderburk |

\* cited by examiner

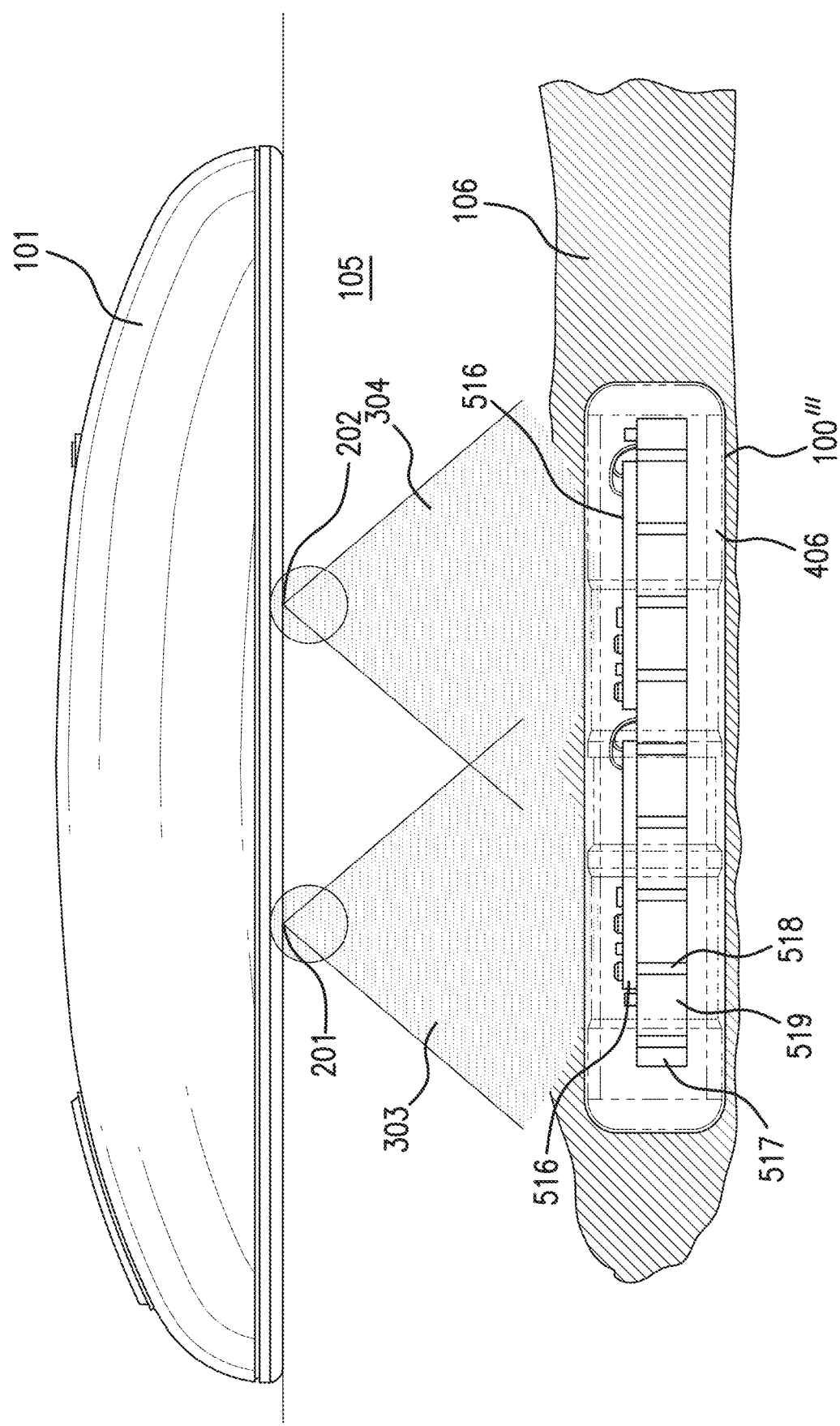

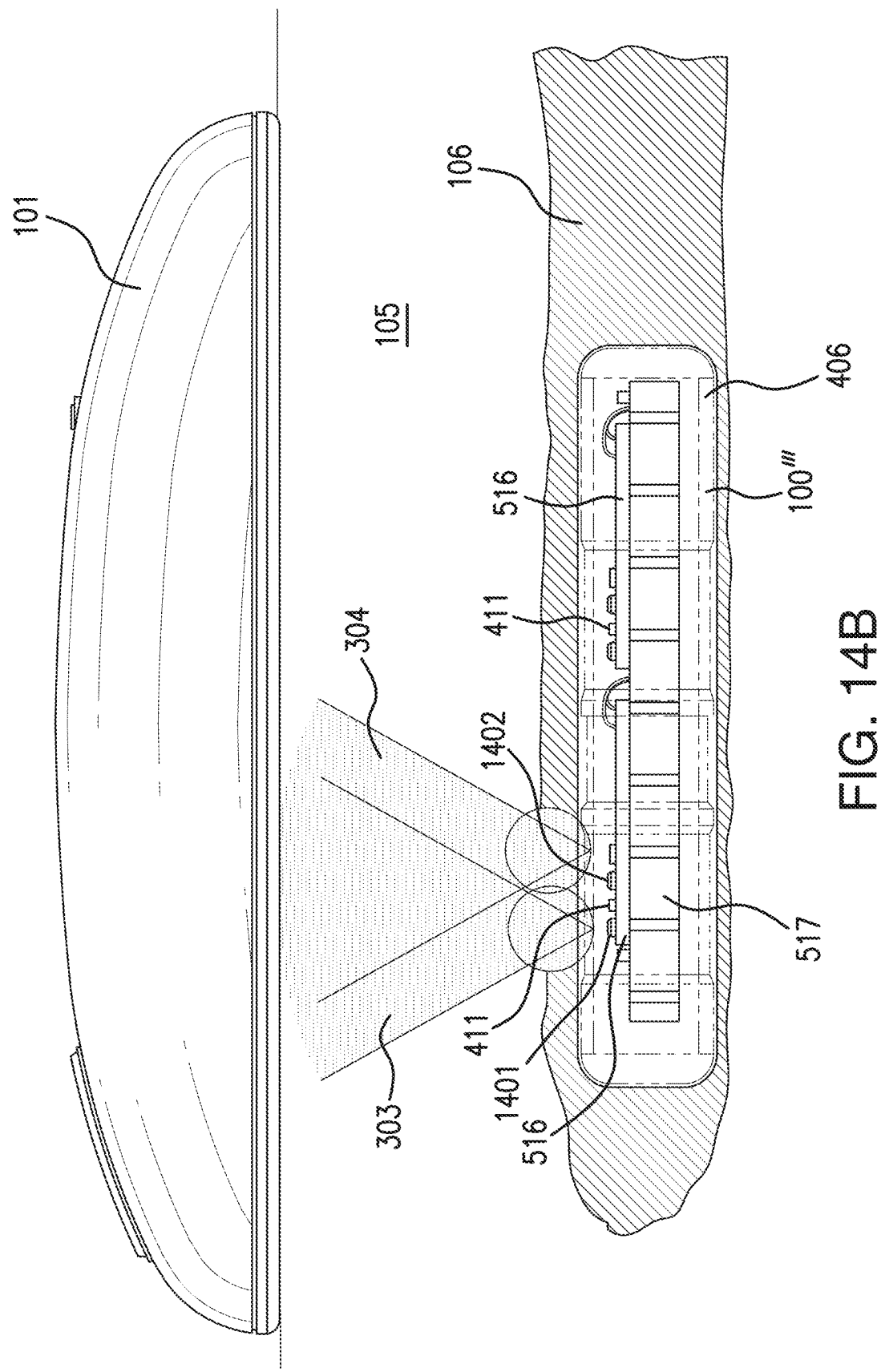

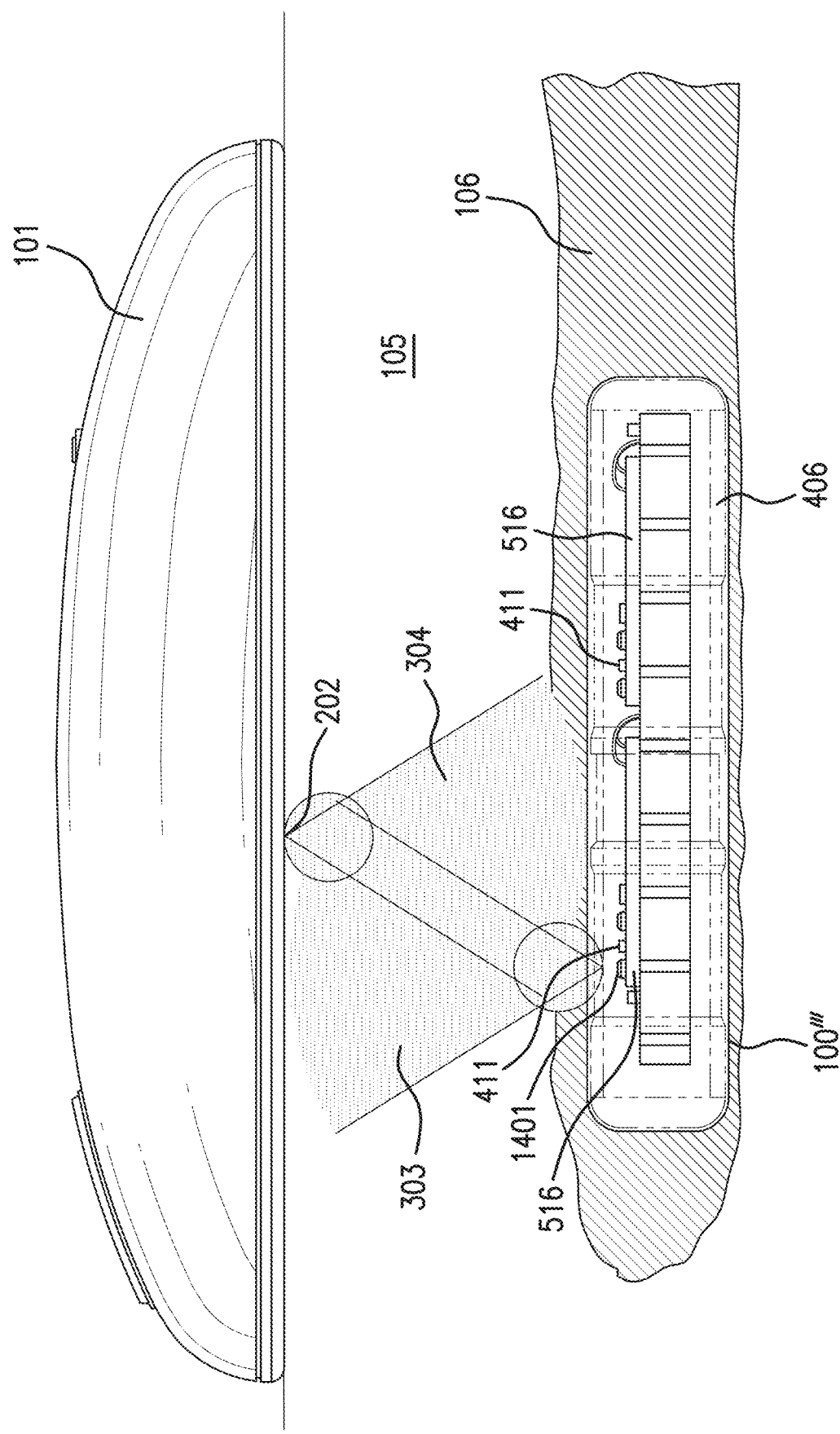

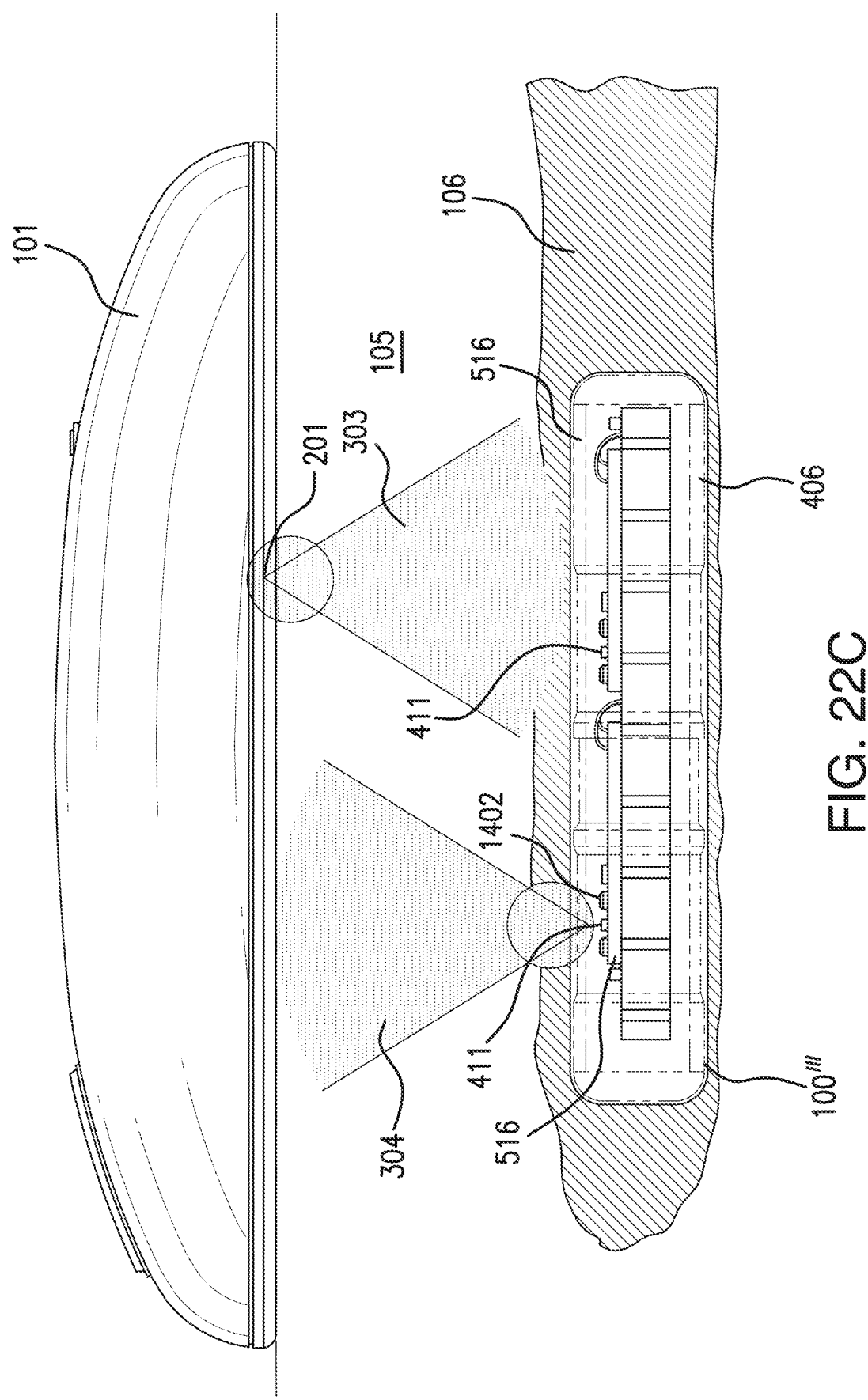

SYSTEM AND METHOD FOR MEASURING AN AMOUNT OF BLOOD AND/OR CLOTTING IN A POCKET SURROUNDING AN IMPLANTABLE MEDICAL DEVICE

CROSS-REFERENCE TO RELATED APPLICATION

The present application claims the benefit of priority to U.S. Provisional Application Ser. No. 62/520,088, filed on Jun. 15, 2017, which is incorporated herein by reference in its entirety.

BACKGROUND

Field of Invention

The present invention relates generally to measuring an amount or volume of blood and/or clotting in a pocket surrounding an implantable medical device. The present invention may additionally or alternatively relate to compensating for the effect of the blood and/or clotting in the pocket surrounding the implantable medical device on an analyte measurement. Specifically, the present invention may relate to using an analyte monitoring system to (1) measure an amount or volume of blood and/or clotting in a pocket surrounding an implantable medical device using at least one or more of (a) externally-emitted and internally-detected light, (b) internally-emitted and externally-detected light, and (c) internally-emitted and internally-detected light, (2) measure an analyte level, and (3) compensate for the effect of the measured amount or volume of blood and/or clotting on the measured analyte level.

Discussion of the Background

Implantable devices may be used for a variety of purposes. For example, implantable devices may be used for sensing of physiological and/or clinical parameters. For another example, implantable devices may be additionally or alternatively used for delivering certain types of electrical/heat therapy. Implantable devices include fully implantable devices and partially implantable devices (e.g., transcutaneous sensing electrodes). Implantable devices may be implanted in a variety of locations, such as, for example and without limitation, under muscle tissue or subcutaneously. When implanted, an implantable device rests in a pocket in the tissue, and the pocket surrounds the implantable device. The pocket may be created by a tissue dissector tool before implantation of the implantable device or by the implantation process.

An implantable device may include an analyte indicator. For example, the analyte indicator may be an electrical, optical, or chemical transduction mechanism. In case of an implantable analyte sensor, analyte signal transduction may be accomplished by measuring a modulation of a detectable property exhibited by the analyte indicator (e.g., fluorescence intensity modulation) using a sensing element (e.g., an optical system).

The implantable device may be part of a system that additionally includes an external device. The external device may power the implantable device and/or receive measurements (e.g., digital representations) of sensed signals (e.g., sensed optical signals) from the implantable device. There is presently a need in the art for improved performance of a system including an implantable device and an external device.

SUMMARY

Ideally, the amount of emission light (e.g., the fluourescence responsivity) of an analyte indicator is proportional to the analyte level in a medium (e.g., interstitial fluid) in proximity to the analyte indicator. However the magnitude of the optical signal is also impacted by other factors such as, for example and without limitation, the opacity of the indicator element (e.g., hydrogel) in which the analyte indicator is located, the amount of blood that is present on the surface of the indicator element, and the amount of hemeprotein that the analyte indicator adsorbs or absorbs. Sensor performance can also be impacted negatively by localized restrictions on the transport of analyte, which may be caused by a fibrous capsule and by coagulated blood that is formed around the sensor after implant. Subsequent tissue repair action may clear the clotted blood, which may change the opacity and resulting amount of emission light (e.g., fluorescent light) emitted by the analyte indicator in the indicator element and detected by the sensor. This change in signal due to the blood and clotting in the pocket may dynamically impact an analyte measurement. Some embodiments of the present invention may maintain and/or improve analyte measurement accuracy by detecting changes due to blood and clotting in the pocket and compensating for the detected change.

A change in hemodynamics (blood pressure heart rate) can impact the transport time of an analyte (e.g., glucose) from arterial blood to interstitial fluid and thus have an impact of the apparent blood analyte to sensor analyte "lag." Some embodiments of the present invention may maintain and/or improve analyte measurement accuracy by additionally or alternatively detecting changes in hemodynamics and compensating for the detected change.

Some embodiments of the present invention may measure the level and status of the blood and the subsequent dynamic status of the clot by generating an optical signal which is proportional to the amount of blood in the pocket. When there is high amount of blood, a larger proportion of the optical signal will be absorbed. When there is less blood and/or the clot is cleared, a larger proportion of the optical signal will be reflected, scattered back and/or transmitted. The reflection can occur at the transition boundaries of the gel to tissue. Some embodiments of the present invention may maintain and/or improve analyte measurement accuracy by determining the dynamic status of the blood and related clot in the pocket and (at least partially) compensating the effect of the blood/clot on the analyte measurement.

Some embodiments of the invention may improve the accuracy of analyte measurements during the early transient period of tissue healing (e.g., following sensor implantation). Some embodiments of the invention may additionally or alternatively provide a measurement of chronic physiologic parameters, such as, for example and without limitation, oxygenation or heart rate. In some embodiments, the physiological parameters may be correlated to impact on analyte measurement over time and/or may be used to compensate for physiological effects. In some embodiments, the physiological parameters may additionally or alternatively be of general health interest.

One aspect of the invention may provide a system including a first light source, a first photodetector, an implantable device, and an external device. The first light source may be configured to emit light over a first wavelength range. The first photodetector may be configured to output a first signal indicative of an amount of the first light received by the first photodetector. The implantable device may include one of the first light source and the first photodetector, and an external device may include the other of the first light source and the first photodetector.

In some embodiments, the external device may further include a controller configured to calculate an amount of blood in a pocket around the implantable device using at least a measurement of the first signal.

In some embodiments, the system may further include a second light source configured to emit light over a second wavelength range, which may be different than the first wavelength range. One of the implantable device and the external device may include the second light source. In some embodiments, the first photodetector may be a common photodetector configured to output the first signal indicative of the amount of the first light received by the common photodetector and to output a second signal indicative of an amount of the second light received by the common photodetector. In some embodiments, the system may further include a second photodetector configured to output a second signal indicative of an amount of the second light received by the second photodetector, and the first and second photodetectors may be different photodetectors. In some embodiments, one of the implantable device and the external device may include the first and second light sources, and the other of the implantable device and the external device may include the first and second photodetectors. In some embodiments, one of the implantable device and the external device may include the first light source and the second photodetector, and the other of the implantable device and the external device may include the second light source and the first photodetector. In some embodiments, the external device may further include a controller configured to calculate an amount of blood in a pocket around the implantable device using at least a measurement of the first signal and a measurement of the second signal.

In some embodiments, the implantable device may further include an excitation light source, an analyte indicator, and an analyte photodetector. The excitation light source may be configured to emit excitation light over an excitation wavelength range. The analyte indicator may be configured to receive the excitation light and emit emission light over an emission light wavelength range, and the amount of emission light may vary in accordance with an amount or concentration of an analyte in a medium within a living animal. The analyte photodetector may be configured to output an analyte signal indicative of an amount of the emission light received by the analyte photodetector. In some embodiments, the external device may include a controller configured to calculate an analyte level based on at least a measurement of analyte signal and one or more of a measurement of the first signal and a measurement of the second signal. In some embodiments, the controller may be further configured to compensate for the calculated amount of blood in the pocket when calculating the analyte level. In some embodiments, the emission wavelength range may include fluorescent light, the first wavelength range may include red light, and the second wavelength range may include infrared light.

In some embodiments, the first wavelength ranges may include red light, and the second wavelength range may include infrared light. In some embodiments, one of the implantable device and the external device may further include a controller configured to cause the first and second light sources to emit the first light and second light simultaneously. In some embodiments, one of the implantable device and the external device may further include a controller configured to cause the first light source to emit the first light during a first time period and to cause the second light source to emit the second light during a second time period, and the first and second time periods may be different time periods.

Another aspect of the invention may provide a method including using a first light source to emit light over a first wavelength range. The method may include using a first photodetector to output a first signal indicative of an amount of the first light received by the first photodetector. An implantable device may include one of the first light source and the first photodetector, and an external device may include the other of the first light source and the first photodetector.

In some embodiments, the method may further include using a controller of the external device to calculate an amount of blood in a pocket around the implantable device using at least a measurement of the first signal. In some embodiments, the method may further include using a second light source to emit light over a second wavelength range, which is different than the first wavelength range, and one of the implantable device and the external device may include the second light source. In some embodiments, the method may further include using the first photodetector to output the first signal indicative of the amount of the first light received by the first photodetector and to output a second signal indicative of an amount of the second light received by the first photodetector. In some embodiments, the method may further include using a second photodetector to output a second signal indicative of an amount of the second light received by the second photodetector, and the first and second photodetectors may be different photodetectors. In some embodiments, the method may further include using a controller to calculate an amount of blood in a pocket around the implantable device using at least a measurement of the first signal and a measurement of the second signal.

In some embodiments, the method may further include using an excitation light source of the implantable device to emit excitation light over an excitation wavelength range. The method may include using an analyte indicator of the implantable device to receive the excitation light and emit emission light over an emission light wavelength range, and the amount of emission light may vary in accordance with an amount or concentration of an analyte in a medium within a living animal. The method may include using an analyte photodetector of the implantable device to output an analyte signal indicative of an amount of the emission light received by the analyte photodetector.

In some embodiments, the method may further include using a controller of the external device to calculate an analyte level based on at least a measurement of analyte signal and one or more of a measurement of the first signal and a measurement of the second signal. In some embodiments, calculating the analyte level may include compensating for the calculated amount of blood in the pocket.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 7G is a schematic view illustrating a system, which includes an external device and the third non-limiting example of the implantable device and embodies aspects of the present invention, in use.

FIGS. 14B and 14C are schematic views illustrating systems, which include an external device and an implantable device and embody aspects of the present invention, in use.

FIGS. 22A-22C are schematic views illustrating systems, which include an external device and an implantable device and embody aspects of the present invention, in use.

DETAILED DESCRIPTION OF PREFERRED EMBODIMENTS

Figure 1A:
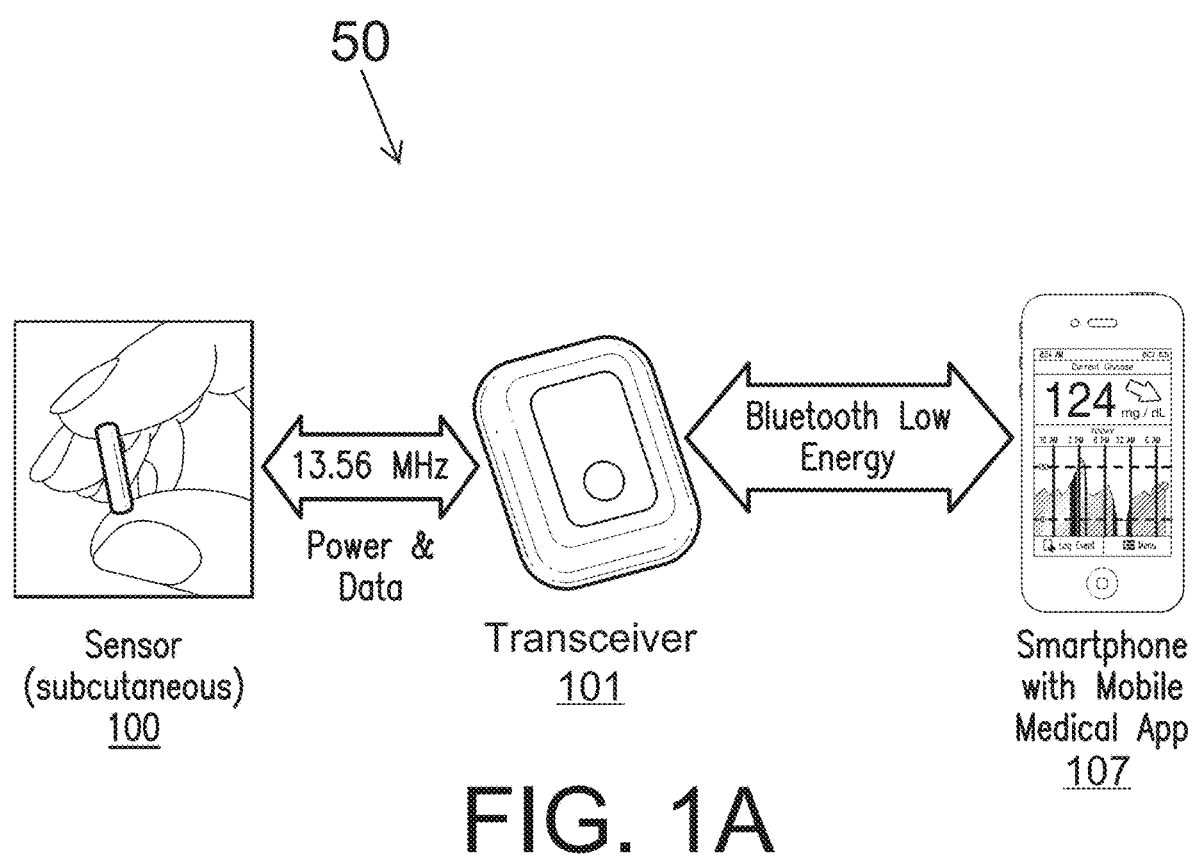
FIG. 1A is a schematic view illustrating a system embodying aspects of the present invention.

FIG. 1A is a schematic view of an exemplary system 50 embodying aspects of the present invention. In some non-limiting embodiments, the system 50 may be an analyte monitoring system. In some non-limiting embodiments, the system 50 may be a continuous analyte monitoring system (e.g., a continuous glucose monitoring system). In some embodiments, the system 50 may include one or more of an implantable device 100, an external device 101, and a display device 107. In some embodiments, the implantable device 100 may be an analyte sensor. In some non-limiting embodiments, the implantable device 100 may be a small, fully subcutaneously implantable sensor that measures the amount or concentration of an analyte (e.g., glucose) in a medium (e.g., interstitial fluid) of a living animal (e.g., a living human). However, this is not required, and, in some alternative embodiments, the implantable device 100 may be a partially implantable (e.g., transcutaneous) device. In addition, although embodiments of the invention are described with respect to an analyte monitoring system in which the implantable device 100 is an analyte sensor, this is not required. In some alternative embodiments, the implantable device 100 is not a sensor and is instead a different type of implantable device, such as, for example and without limitation, an insulin pump, pacemaker, or electrical/heat therapy device.

In some embodiments, the external device 101 may be an externally worn device (e.g., attached via an armband, wristband, waistband, or adhesive patch). In some embodiments, the external device 101 may remotely power and/or communicate with the implantable device 100 (e.g., via near field communication (NFC)). However, this is not required, and, in some alternative embodiments, the external device 101 may power and/or communicate with the implantable device 100 via one or more wired connections. In some embodiments, the external device 101 may power and/or communicate with the implantable device 100 to initiate and receive the measurements from the implantable device 100. In some embodiments, the external device 101 may be a transceiver. In some non-limiting embodiments, the external device 101 may be a smartphone (e.g., an NFC-enabled smartphone). In some embodiments, the external device 101 may communicate information (e.g., one or more analyte measurements) wirelessly (e.g., via a Bluetooth™ communication standard such as, for example and without limitation Bluetooth Low Energy) to a hand held application running on a display device 107 (e.g., smartphone).

Figure 1B:
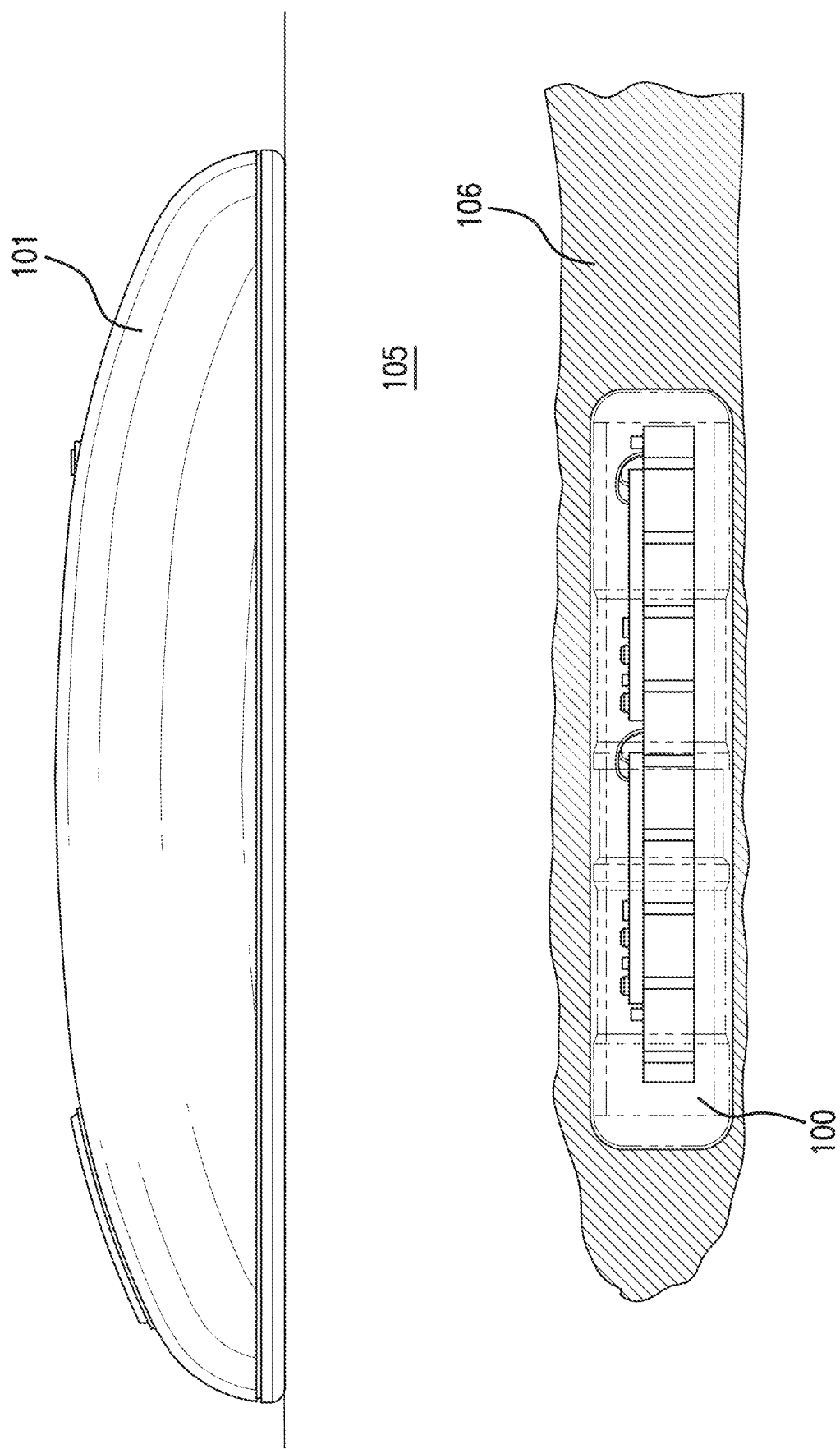
FIG. 1B is a schematic view illustrating an implantable device and an external device of a system embodying aspects of the present invention.

In some non-limiting embodiments, as illustrated in FIG. 1B, when the system 50 is in use, the implantable device 100 may be implanted in the tissue 105 of the living animal, and the external device 101 may be external to the tissue 105. In some embodiments, the back of the external device 101 may be adjacent to the tissue 105 (e.g., adjacent to the skin of the living animal). As shown in FIG. 1B, after implantation, the implantable device 100 may rest in a pocket 106 in the tissue 105, and the pocket 106 may surround the implantable device 100. In some non-limiting embodiments, the pocket 106 may be created by a tissue dissector tool before implantation of the implantable device 100 or by the implantation process.

Figure 2:
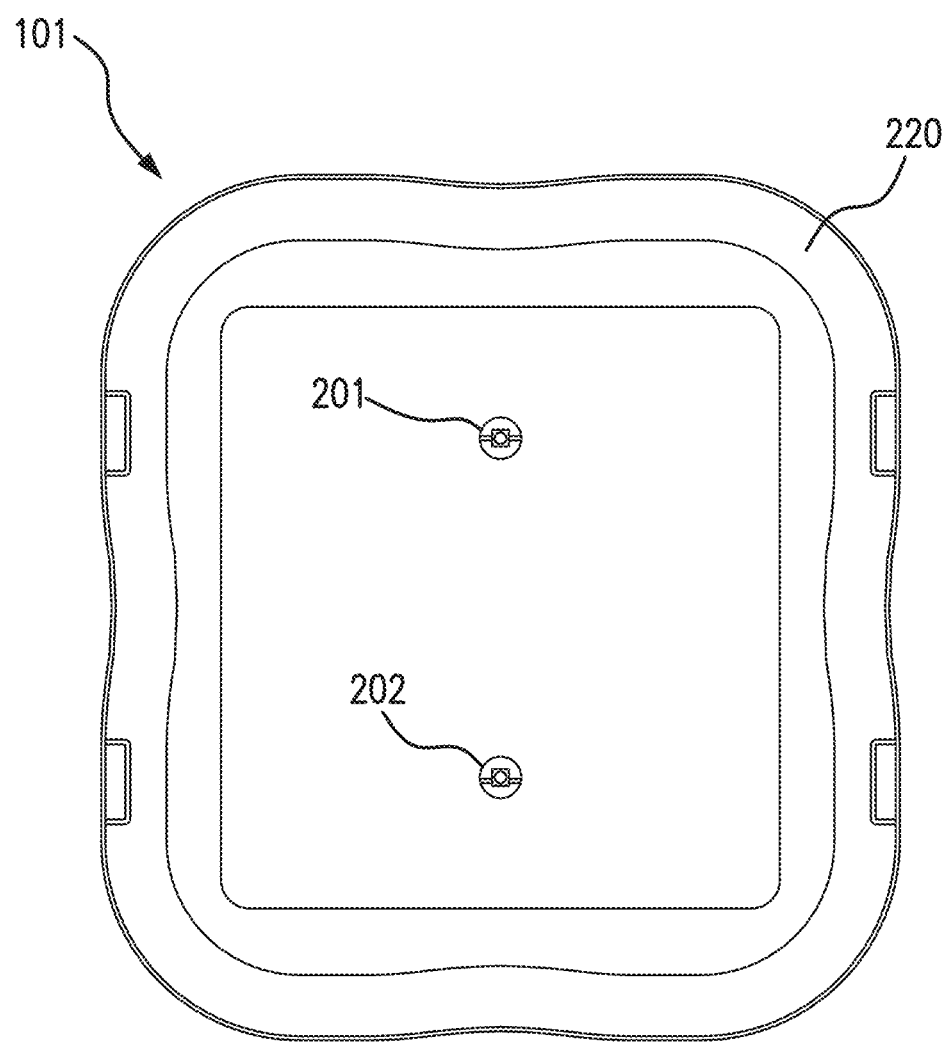
FIG. 2 is a back view of an external device including first and second external light sources and embodying aspects of the present invention.

FIG. 2 is a back view illustrating an external device 101 embodying aspects of the present invention. In some embodiments, as shown in FIG. 2, the external device 101 may include a housing 220, which may be a back housing. In some embodiments, as shown in FIG. 2, the external device 101 may include one or more first external light sources 201 and/or one or more second external light sources 202.

Figure 3:
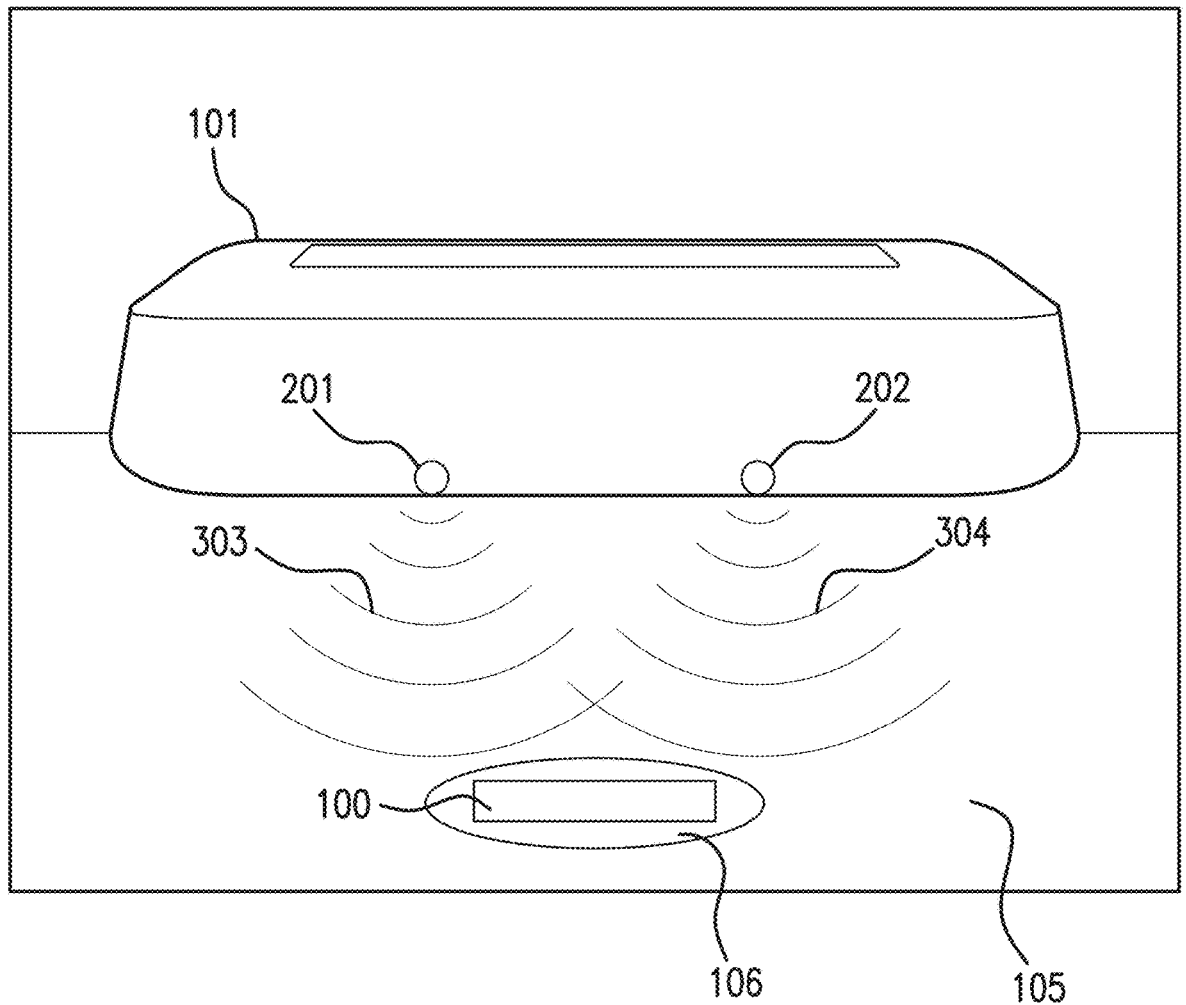
FIG. 3 is a schematic view illustrating an implantable device and an external device of a system embodying aspects of the present invention.

FIG. 3 is a schematic view illustrating an implantable device 100 and an external device 101 of a system 50 embodying aspects of the present invention. In some embodiments, as shown in FIG. 3, the first external light source 201 may emit first light 303. In some embodiments, the first light 303 may be over a first wavelength range. In some embodiments, as shown in FIG. 3, the one or more second external light sources 202 may emit second light 304. In some embodiments, the second light 303 may be over a second wavelength range, which may be different than the first wavelength range. In some non-limiting embodiments, the first and second wavelength ranges do not overlap, but this not required, and, in some alternative embodiments, the first and second wavelength ranges may overlap.

Figure 24A:
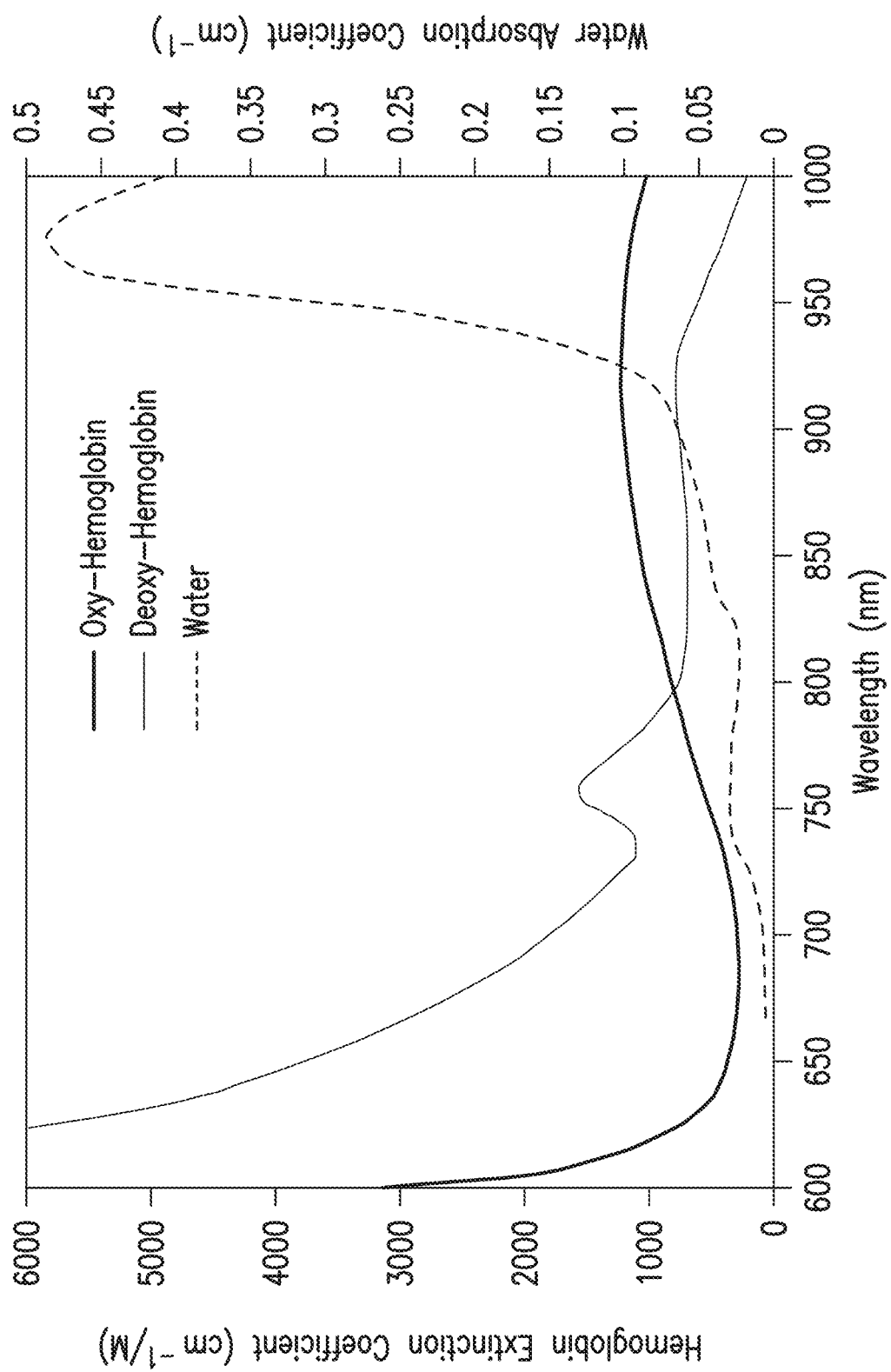
FIG. 24A is a graph illustrating oxy-hemoglobin extinction, de-oxy hemoglobin, and water absorption coefficients at different wavelengths.
Figure 24B:
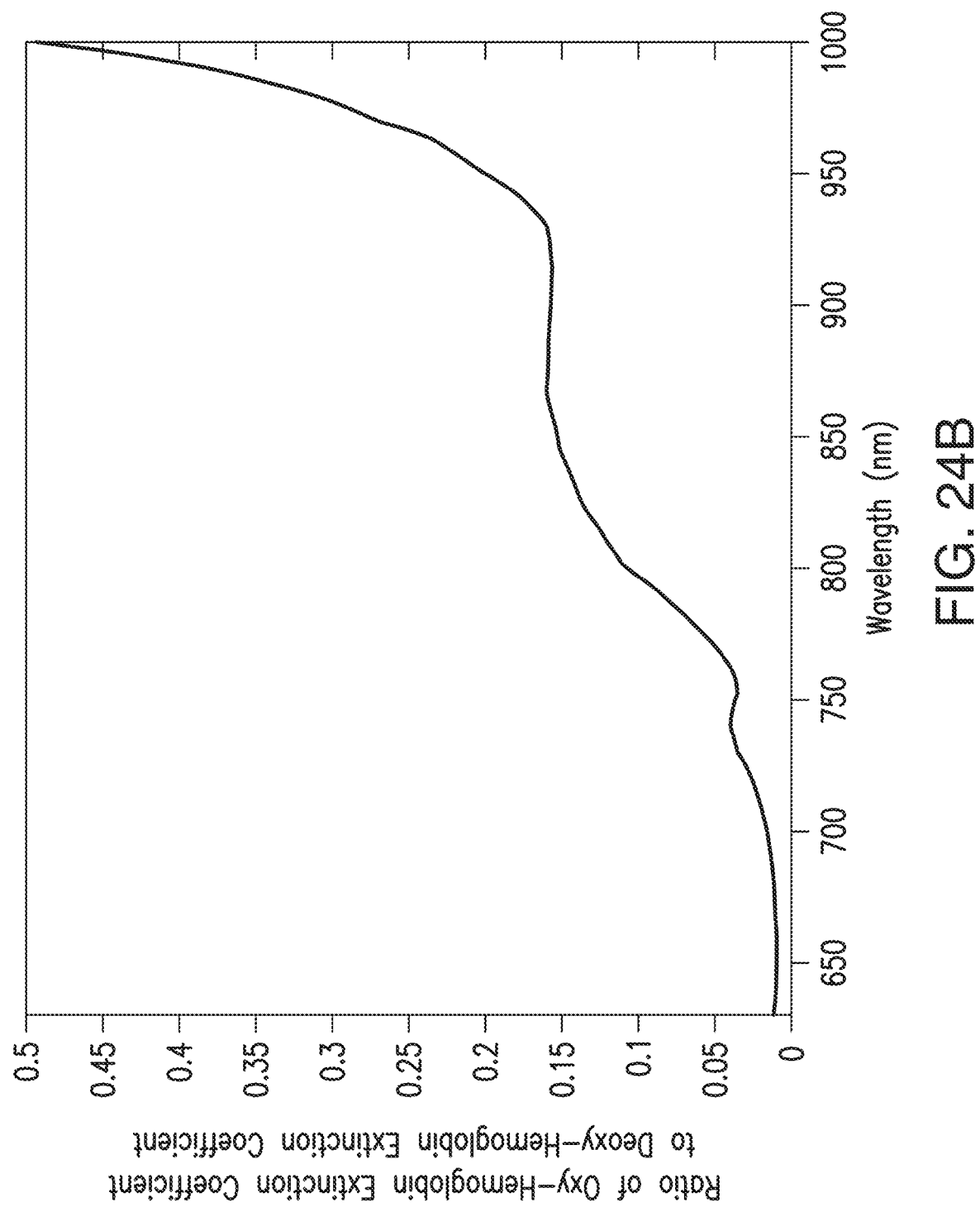
FIG. 24B is a graph illustrating a ratio of the oxy-hemoglobin extinction coefficient to the doxy-hemoglobin coefficient at different wavelengths.

In some non-limiting embodiments, the wavelengths of the first and second light 303 and 304 may be such that blood oxygenation may be determined from measurements of the first and second light 303 and 304. FIG. 24A is a graph illustrating oxy-hemoglobin extinction, de-oxy hemoglobin, and water absorption coefficients at different wavelengths. FIG. 24B is a graph illustrating a ratio of the oxy-hemoglobin extinction coefficient to the doxy-hemoglobin coefficient at different wavelengths. In some non-limiting embodiments, the first and second wavelength ranges may be such that (i) the absorption of the first and second wavelengths of light is not so much that no signal can be measured but not so little that hemoglobin has no effect on them (see FIG. 24A), and (ii) the ratio of oxyhemoglobin absorption to de-oxy hemoglobin absorption is significantly different at the first and second wavelengths (see FIG. 24B). In some non-limiting embodiments, the first and second wavelength ranges may be outside a wavelength range at which too much of the first and second light 303 and 304 would be absorbed by water (see FIG. 24A). In some non-limiting embodiments, the first wavelength may be a wavelength at which the ratio of the oxy-hemoglobin extinction coefficient to the doxy-hemoglobin coefficient is small, and the second wavelength may be a wavelength at which the ratio of the oxy-hemoglobin extinction coefficient to the doxy-hemoglobin coefficient is large.

In some non-limiting embodiments, the first light 303 may include one or more of red light and infrared light. In non-limiting embodiments, the first light 303 may include red light. In some non-limiting embodiments, the second light 304 may include one or more of red light and infrared light. In non-limiting embodiments, the second light 304 may include infrared light. In some non-limiting embodiments, the first and second wavelength ranges may be centered at, for example and without limitation, (a) 660 nm and 800 nm, respectively, (b) 750 nm and 850 nm, respectively, (c) 800 nm and 840 nm, respectively, (d) 654 and 740, respectively, (e) 740 nm and 800 nm, respectively, or (f) 660 nm and 940 nm, respectively. In some embodiments, the first light 303 may substantially pass through oxygenated hemoglobin but substantially be absorbed by deoxygenated hemoglobin. In some embodiments, the second light 304 may substantially pass through deoxygenated hemoglobin but substantially be absorbed by oxygenated hemoglobin.

In some embodiments, deoxygenated hemoglobin may absorb a greater percentage of the first light 303 than the percentage of the second light 304 absorbed by deoxygenated hemoglobin. In some embodiments, deoxygenated hemoglobin may pass through or reflect a greater percentage of the second light 304 than the percentage of the first light 303 passed through or reflected by deoxygenated hemoglobin. In some embodiments, oxygenated hemoglobin may absorb a greater percentage of the second light 304 than the percentage of the first light 303 absorbed by oxygenated hemoglobin. In some embodiments, oxygenated hemoglobin may pass through or reflect a greater percentage of the first light 303 than the percentage of the second light 304 passed through or reflected by oxygenated hemoglobin.

In some embodiments, one or more of the first and second external light sources 201 and 202 may emit the first light 303 and/or the second light 304 into the tissue 105. Some or all of the first and second light 303 and 304 may pass through the tissue 105, through any blood and/or clotting in the pocket 106 in the tissue 105 surrounding the implantable device 100, and into the implantable device 100. In some embodiments, the amount of the first light 303 that passes through any blood and/or clotting in the pocket 106 may vary in accordance with the amount of blood and/or clotting in the pocket 106. In some non-limiting embodiments, the amount of the first light 303 that passes through any blood and/or clotting in the pocket 106 may vary in accordance with the amount of deoxygenated hemoglobin in the pocket 106. In some embodiments, the amount of the second light 304 that passes through any blood and/or clotting in the pocket 106 may vary in accordance with the amount of blood and/or clotting in the pocket 106. In some non-limiting embodiments, the amount of the second light 304 that passes through any blood and/or clotting in the pocket 106 may vary in accordance with the amount of oxygenated hemoglobin in the pocket 106.

Figure 4:
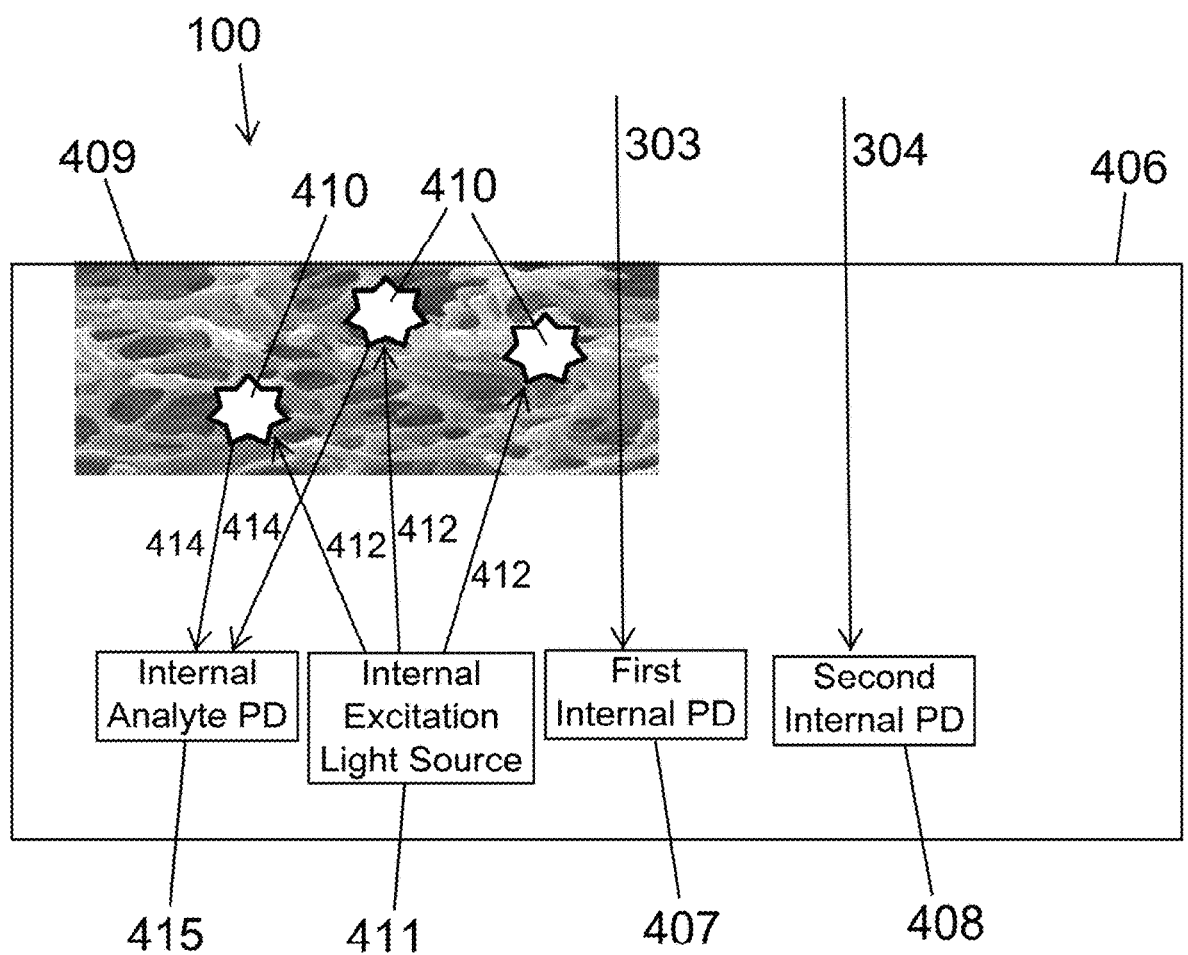
FIG. 4 is a schematic view of an implantable device including first and second internal photodetectors and embodying aspects of the present invention.

FIG. 4 is a schematic view illustrating an implantable device 100 embodying aspects of the present invention. In some embodiments, the implantable device 100 may include one or more internal photodetectors (e.g., photodiodes, phototransistors, photoresistors, or other photosensitive elements). In some embodiments, the one or more photodetectors of the implantable device 100 may include one or more first internal photodetectors 407. In some non-limiting embodiments, the one or more first internal photodetectors 407 may be configured to output a first signal indicative of an amount of the first light 303 received by the one or more first internal photodetectors 407. In some non-limiting embodiments, the one or more first internal photodetectors 407 may be configured to output a first signal indicative of an amount of the first light 303 received by the one or more first internal photodetectors 407 because one or more optical filters may prevent light outside the first wavelength range (i.e., light outside the wavelength range of the first light 303 emitted by the one or more first external light sources 201) from reaching the one or more first internal photodetectors 407. In some embodiments, the first signal may vary in accordance with the amount of blood and/or clotting in the pocket 106. In some non-limiting embodiments, the first signal may vary in accordance with the amount of deoxygenated hemoglobin in the pocket 106.

In some embodiments, the one or more internal photodetectors of the implantable device 100 may include one or more second photodetectors 408. In some non-limiting embodiments, the one or more second photodetectors 408 may be configured to output a second signal indicative of an amount of the second light 304 received by the one or more second photodetectors 408. In some non-limiting embodiments, the one or more second internal photodetectors 408 may be configured to output a second signal indicative of an amount of the second light 304 received by the one or more second internal photodetectors 408 because one or more optical filters may prevent light outside the second wavelength range (i.e., light outside the wavelength range of the second light 304 emitted by the one or more second external light sources 202) from reaching the one or more second internal photodetectors 408. In some embodiments, the second signal may vary in accordance with the amount of blood and/or clotting in the pocket 106. In some non-limiting embodiments, second signal may vary in accordance with the amount of oxygenated hemoglobin in the pocket 106.

In some non-limiting embodiments, the implantable device 100 may be an analyte sensor that may detect the presence, amount, and/or concentration of an analyte (e.g., glucose, oxygen, cardiac markers, low-density lipoprotein (LDL), high-density lipoprotein (HDL), or triglycerides). In some non-limiting embodiments, the implantable device 100 may be an optical sensor (e.g., fluorometers). In some embodiments, the implantable device 100 may be a chemical or biochemical sensor. In some embodiments, the implantable device 100 may be a radio frequency identification (RFID) device. In some embodiments, the implantable device 100 may be powered by a radio frequency (RF) signal from the external device 101.

In some non-limiting embodiments, as illustrated in FIG. 4, the implantable device 100 may include a housing 406 (i.e., body, shell, capsule, or encasement), which may be rigid and biocompatible. In one non-limiting embodiment, the housing 406 may be a silicon tube. However, this is not required, and, in other embodiments, different materials and/or shapes may be used for the housing 406. In some embodiments, the implantable device 100 may include a transmissive optical cavity. In some non-limiting embodiments, the transmissive optical cavity may be formed from a suitable, optically transmissive polymer material, such as, for example, acrylic polymers (e.g., polymethylmethacrylate (PMMA)). However, this is not required, and, in other embodiments, different materials may be used for the transmissive optical cavity.

In some embodiments, as shown in FIG. 4, the implantable device 100 may include one or more indicator elements 409, such as, for example, a polymer graft or hydrogel coated, diffused, adhered, embedded, or grown on or in at least a portion of the exterior surface of the housing 406. In some non-limiting embodiments, the housing 406 may include one or more cutouts or recesses, and the one or more indicator elements 409 may be located (partially or entirely) in the cutouts or recesses. In some embodiments, the one or more indicator element 409 may be porous and may allow the analyte (e.g., glucose) in a medium (e.g., interstitial fluid) to diffuse into the one or more indicator element 409.

In some embodiments, the one or more indicator elements 409 (e.g., polymer grafts or hydrogels) of the implantable device 100 may include an analyte indicator 410. In some embodiments, the analyte indicator 410 may exhibit one or more detectable properties (e.g., optical properties) that vary in accordance with the amount or concentration of the analyte in proximity to the one or more indicator elements 409. In some non-limiting embodiments, the analyte indicator 410 may emit an amount of emission light 414 that varies in accordance with the amount or concentration of the analyte in proximity to the one or more indicator elements 409. In some embodiments, the analyte indicator 410 may include one or more analyte indicator molecules (e.g., fluorescent analyte indicator molecules), which may be distributed throughout the indicator element 409. In some non-limiting embodiments, the analyte indicator 410 may be a phenylboronic-based analyte indicator. However, a phenylboronic-based analyte indicator is not required, and, in some alternative embodiments, the implantable device 100 may include a different analyte indicator, such as, for example and without limitation, a glucose oxidase-based indicator, a glucose dehydrogenase-based indicator, or a glucose binding protein-based indicator.

In some embodiments, as shown in FIG. 4, the implantable device 100 may include one or more internal excitation light sources 411 that emit excitation light 412 over an excitation wavelength range. In some non-limiting embodiments, the excitation wavelength range may be a range of wavelengths that interact with the analyte indicator 410 in the indicator element 409. In some non-limiting embodiments, the excitation light 412 may be ultraviolet (UV) light. In some non-limiting embodiments, the first, second, and excitation wavelength ranges may be different wavelength ranges. In some non-limiting embodiments, the first, second, and excitation wavelength ranges may be non-overlapping wavelength ranges.

In some embodiments, the implantable device 100 may include one or more sensor elements configured to detect a detectable property of the indicator element 409 and output an analyte signal indicative of the amount or concentration of the analyte in the medium within the living animal. In some embodiments, as shown in FIG. 4, the one or more internal photodetectors of the implantable device 100 may include one or more internal analyte photodetectors 415. In some non-limiting embodiments, the one or more internal analyte photodetectors 415 may be configured to output an analyte signal indicative of an amount of the emission light 414 (e.g., fluorescent light) received by the one or more internal analyte photodetectors 415. In some non-limiting embodiments, the one or more internal analyte photodetectors 415 may be configured to output an analyte signal indicative of an amount of the emission light 414 received by the one or more internal analyte photodetectors 415 because one or more optical filters may prevent light outside the emission light wavelength range (i.e., light outside the wavelength range of the emission light 414 emitted by the analyte indicator 410) from reaching the one or more internal analyte photodetectors 415. In some embodiments, as the amount of emission light 414 emitted by the analyte indicator 410 may be vary in in accordance with the amount or concentration of the analyte in proximity to the indicator element 409, the analyte signal output by the one or more internal analyte photodetectors 415 may be indicative of an amount or concentration of an analyte in a medium in proximity to the indicator element 409.

Figure 5A:
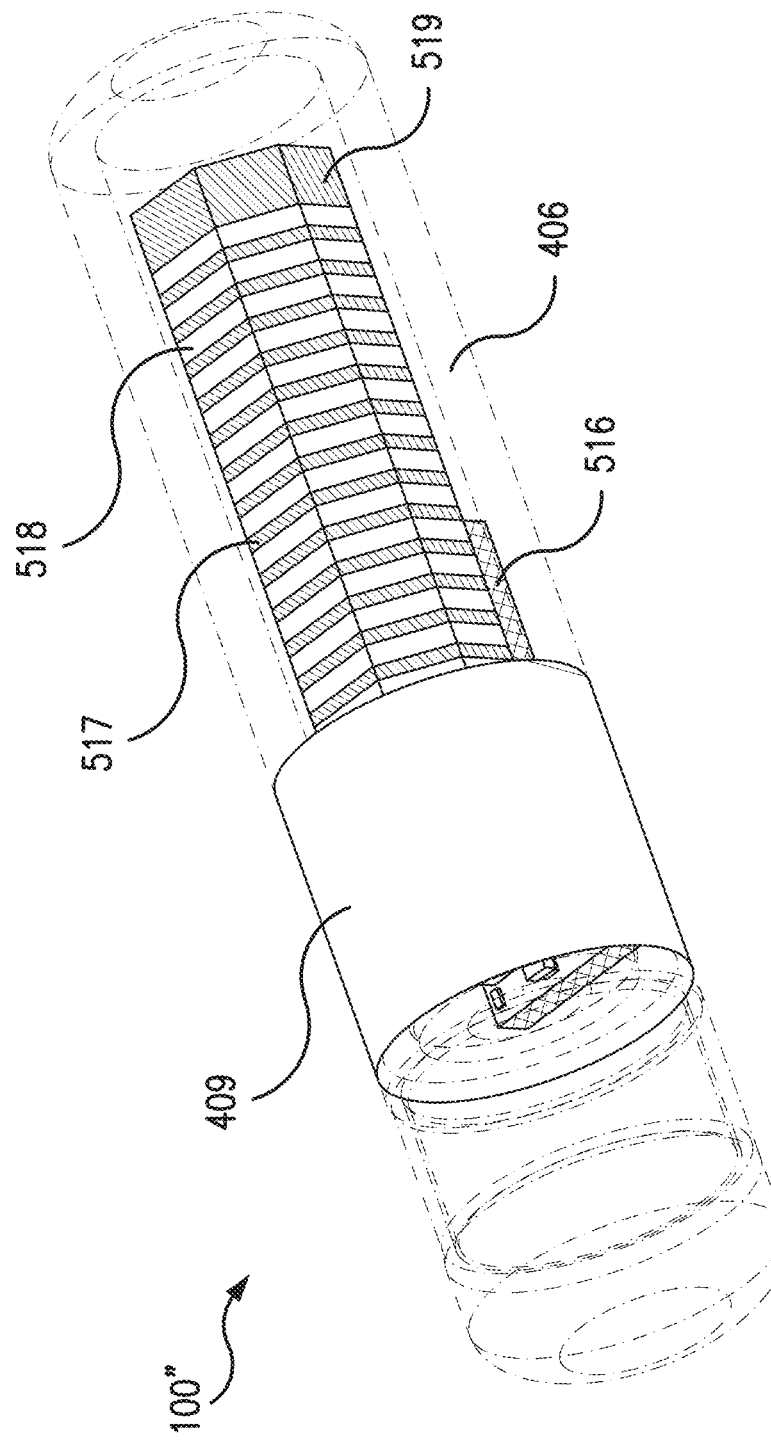
FIG. 5A is a perspective view illustrating a first non-limiting example of an implantable device embodying aspects of the present invention.
Figure 5B:
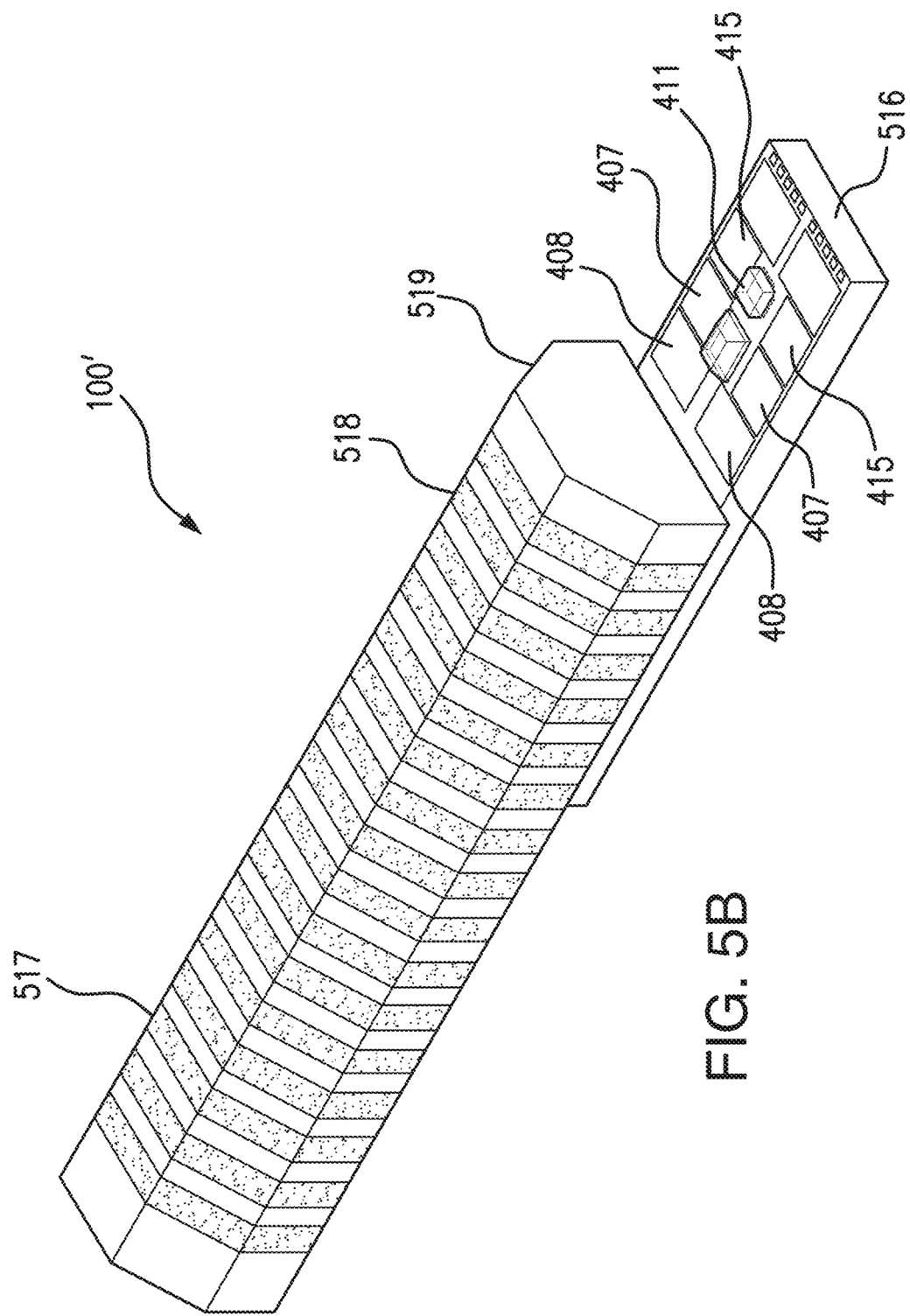
FIG. 5B is a perspective view illustrating elements of the first non-limiting example of the implantable device embodying aspects of the present invention.

FIG. 5A is a perspective view illustrating an implantable device 100' that is a first non-limiting example of the implantable device 100 of the system 50, and FIG. 5B is a perspective view illustrating elements of the implantable device 100'. In some embodiments, as shown in FIGS. 5A and 5B, the implantable device 100 may include one or more of the housing 406, indicator element 409, internal photodetectors 407, 408, and 415, and internal light source(s) 411. In some embodiments, as shown in FIGS. 5A and 5B, the implantable device 100 may include a substrate 516. In some non-limiting embodiments, the substrate 516 may be a circuit board (e.g., a printed circuit board (PCB) or flexible PCB) on which one or more of circuit components (e.g., analog and/or digital circuit components) may be mounted or otherwise attached. However, in some alternative embodiments, the substrate 516 may be a semiconductor substrate.

Figure 6:
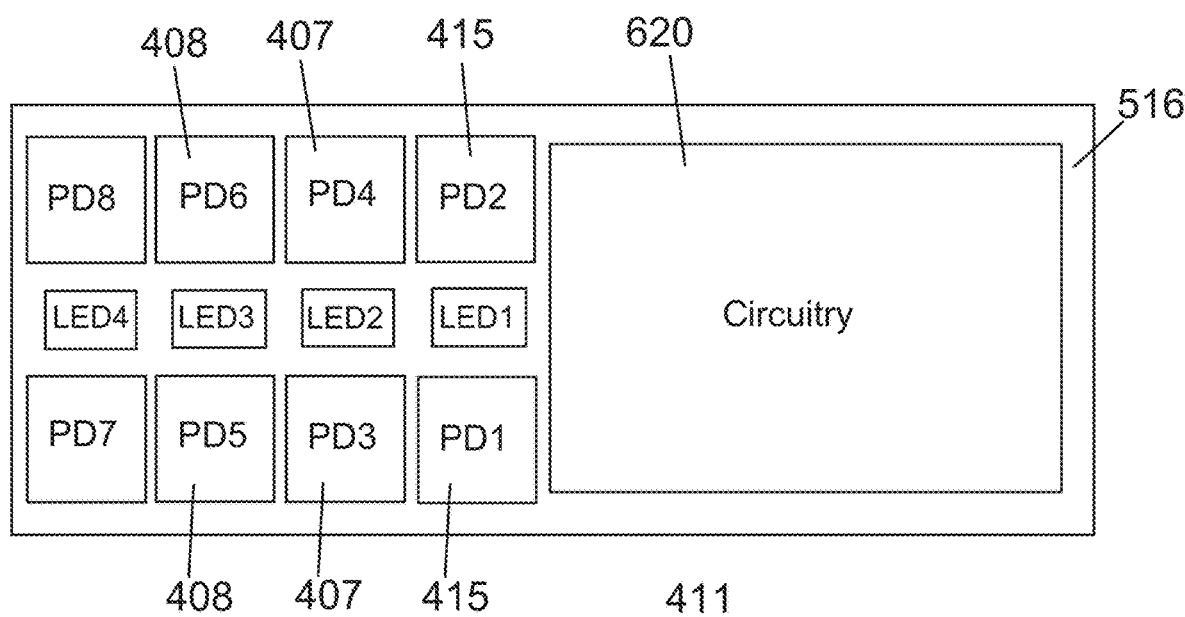
FIG. 6 is a schematic view illustrating the layout of a semiconductor substrate of an implantable device embodying aspects of the present invention.

FIG. 6 is a schematic view illustrating the layout of substrate 516 that is a semiconductor substrate embodying aspects of the present invention. As shown in FIG. 6, the semiconductor substrate 516 may have one or more of circuit components fabricated therein. For instance, the fabricated circuit components 620 may include analog and/or digital circuitry. Also, in some embodiments in which the substrate 516 is a semiconductor substrate, in addition to the circuit components 620 fabricated in the semiconductor substrate, circuit components may be mounted or otherwise attached to the semiconductor substrate. In other words, in some semiconductor substrate embodiments, a portion or all of the circuit components, which may include discrete circuit elements, an integrated circuit (e.g., an application specific integrated circuit (ASIC)) and/or other electronic components (e.g., a non-volatile memory), may be fabricated in the semiconductor substrate with the remainder of the circuit components is secured to the semiconductor substrate, which may provide communication paths between the various secured components.

In some embodiments, as shown in FIGS. 5B and 6, the implantable device 100 may include one or more light sources 411, and one or more of the light sources 411 may be mounted on or fabricated within in the substrate 516. In some embodiments, the implantable device 100 may include one or more photodetectors 407, 408, 415, and one or more of the photodetectors 407, 408, 415 may be mounted on or fabricated in the substrate 516. In some non-limiting embodiments, one or more light sources 411 may be mounted on the substrate 516, one or more photodetectors 407, 408, 415 may be fabricated within the substrate 516, and all or a portion of the circuit components may be fabricated within the substrate 516.

Although the implantable device 100' illustrated in FIGS. 5A and 5B has one substrate 516, this is not required, and, in some alternative embodiments, the implantable device 100' may include more than one substrate 516 (e.g., more than one semiconductor substrate). In some non-limiting alternative embodiments, at least the one or more first internal photodetectors 407 may be on a first substrate, and at least the one or more second internal photodetectors 408 may be a second substrate that is separate and distinct from the first substrate.

Figure 7A:
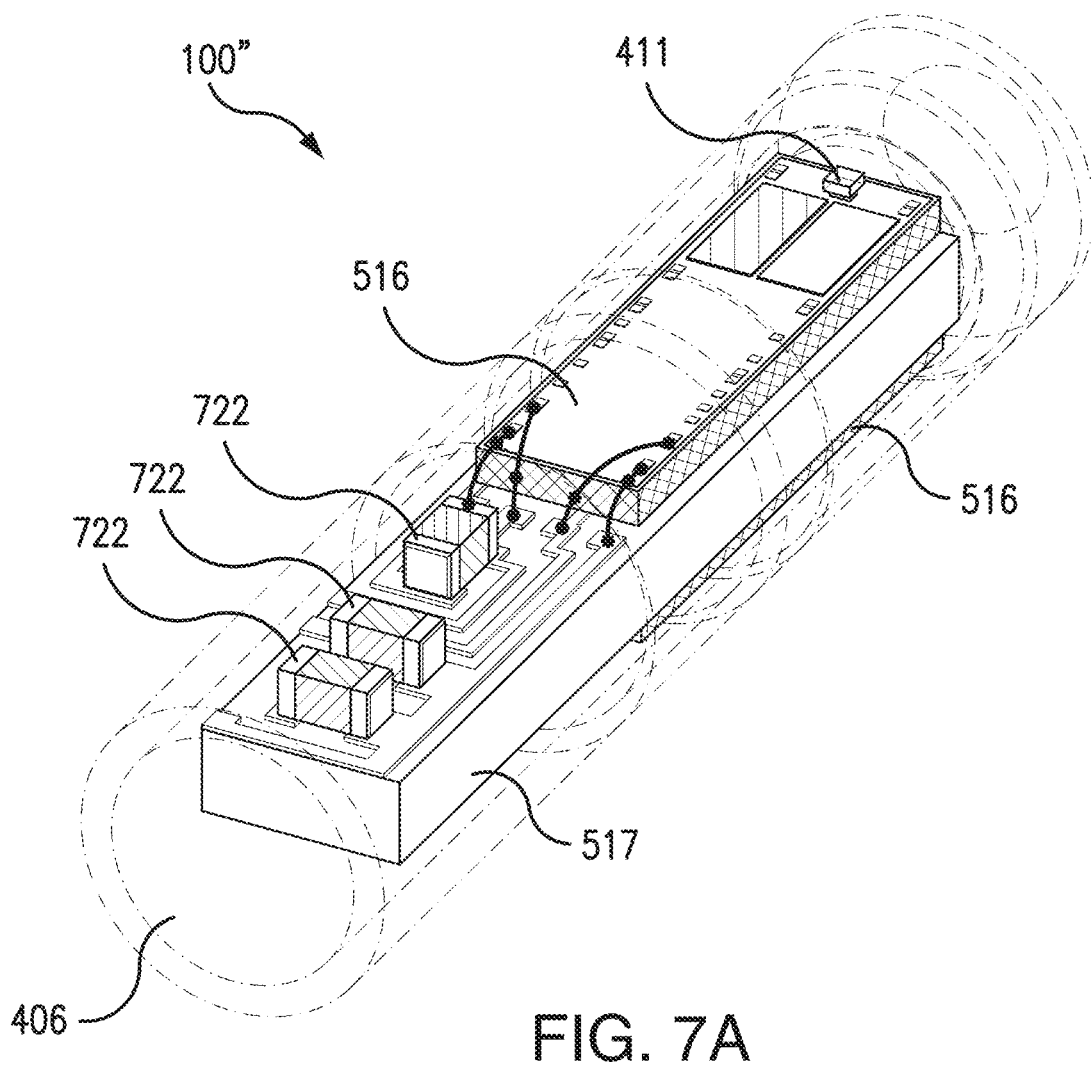
FIGS. 7A-7C are perspective, side, and cross-sectional views, respectively, of a second non-limiting example of an implantable device embodying aspects of the present invention.
Figure 7B:
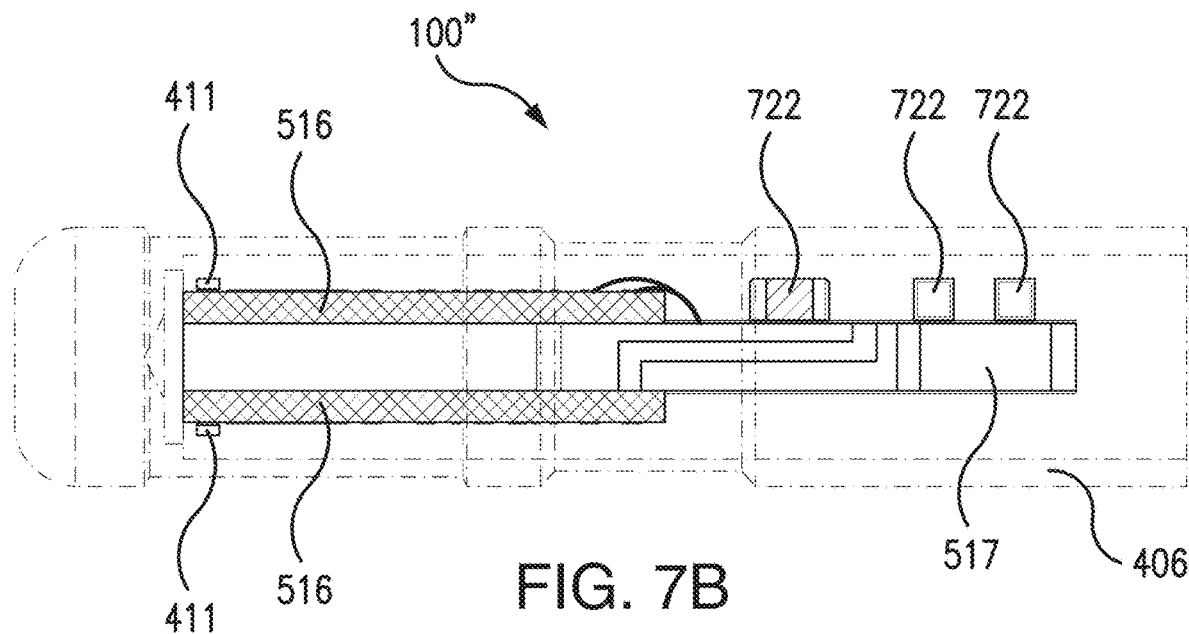
Figure 7C:
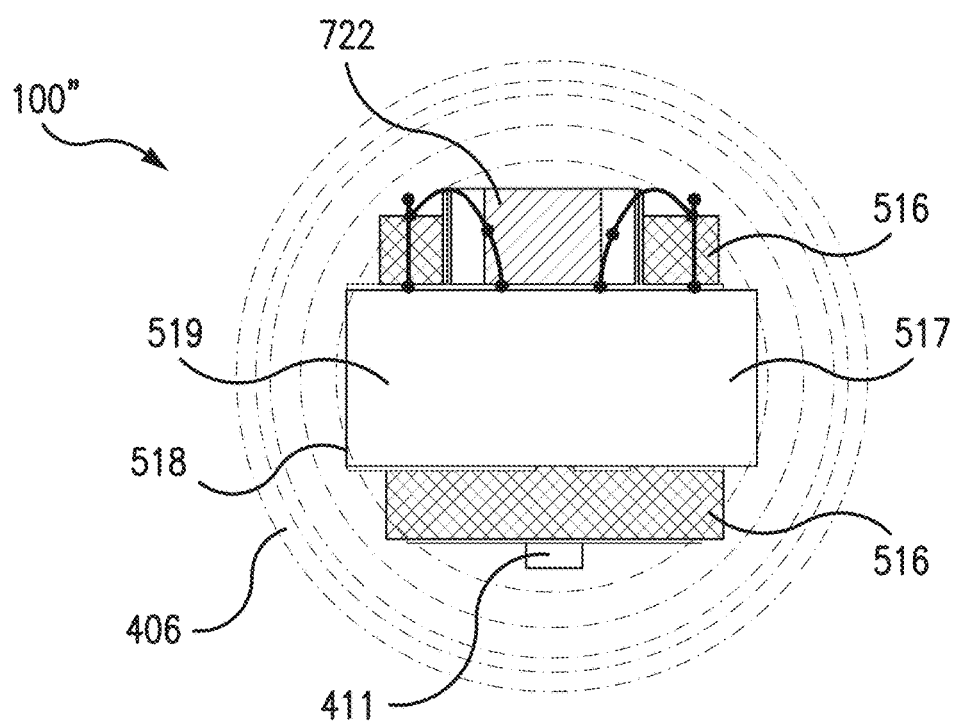
Figure 7D:
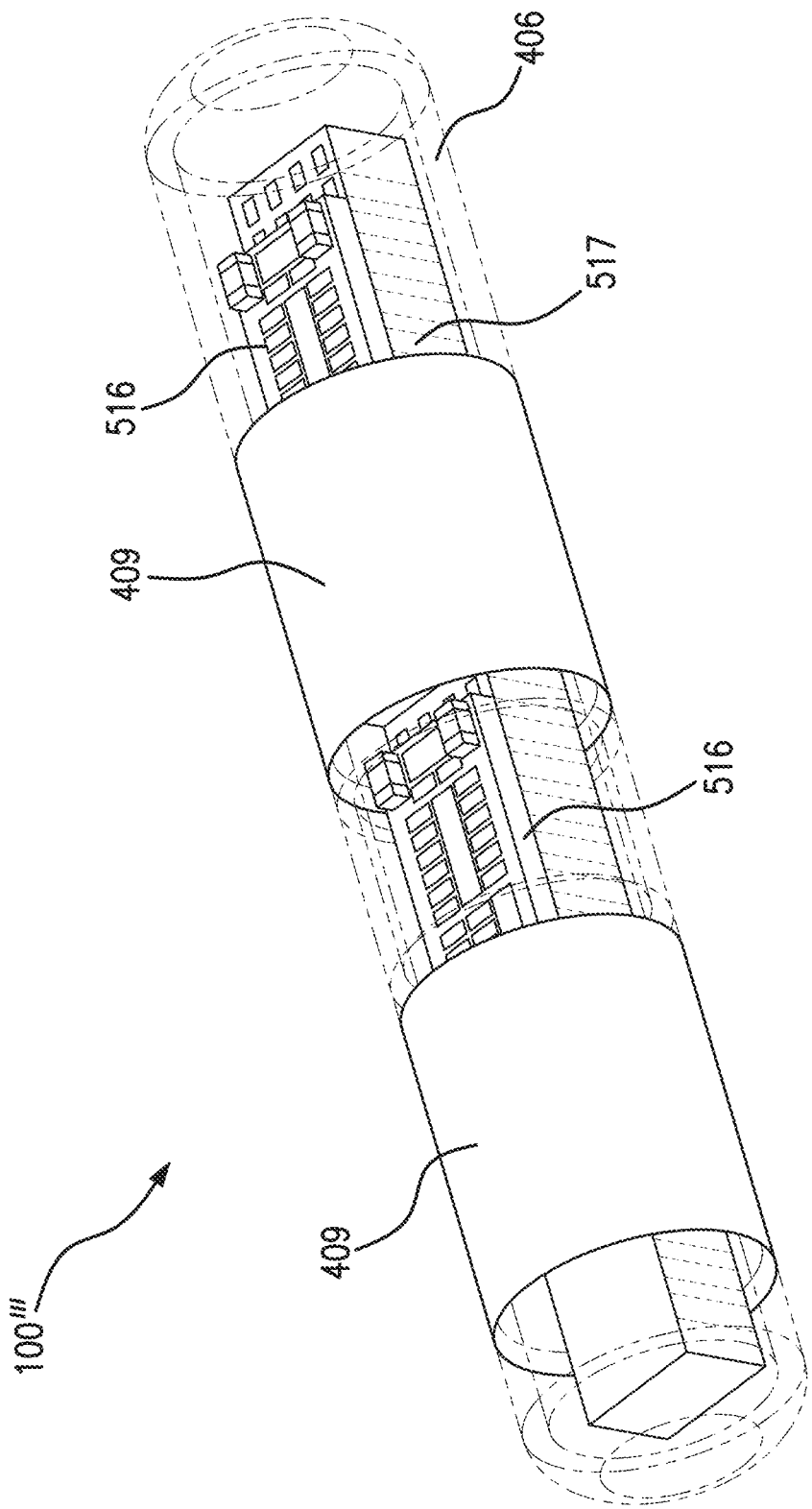
FIGS. 7D, 7E, and 7F are perspective, perspective, and side views, respectively, of a third non-limiting implantable device embodying aspects of the present invention.
Figure 7E:
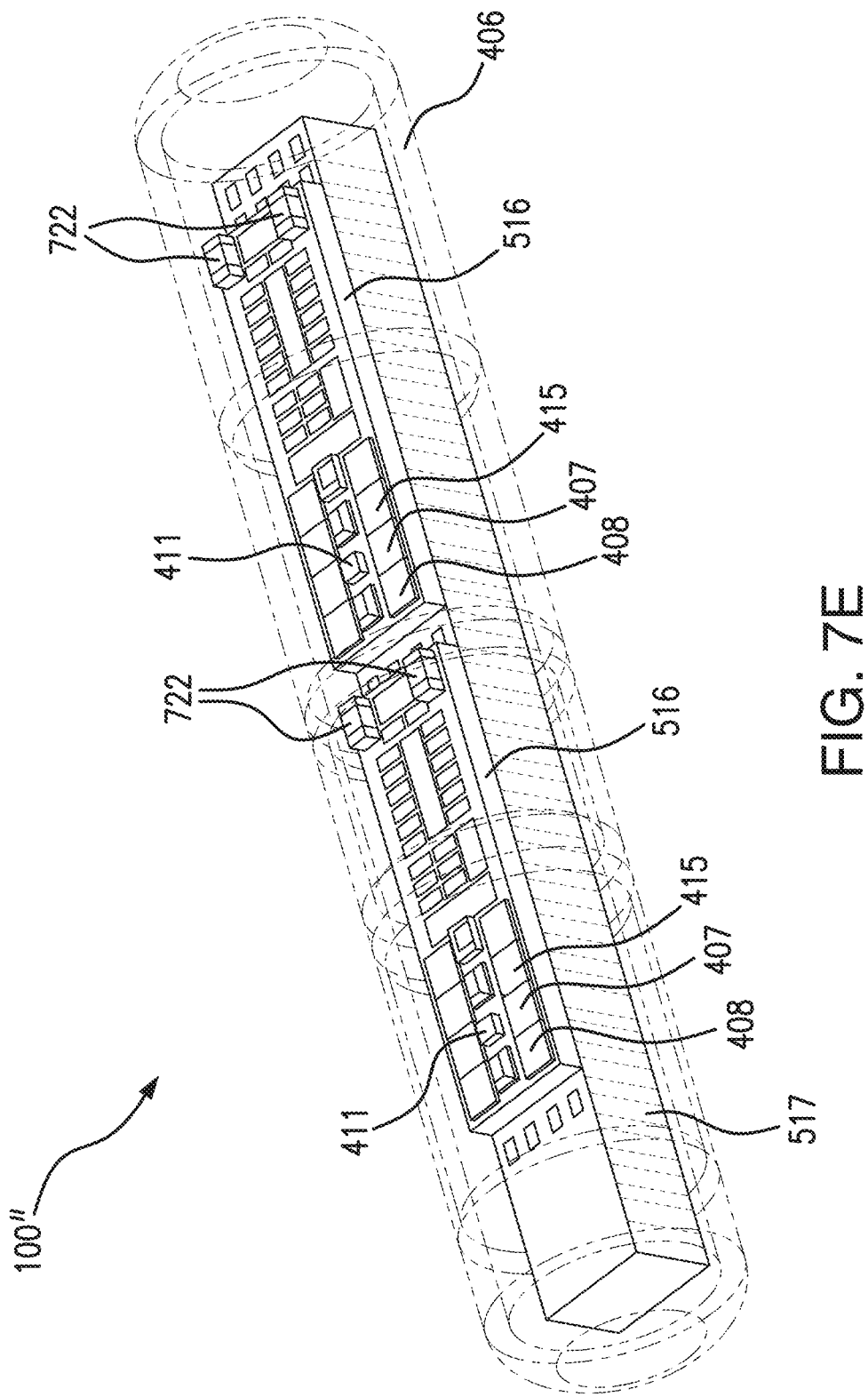
Figure 7F:
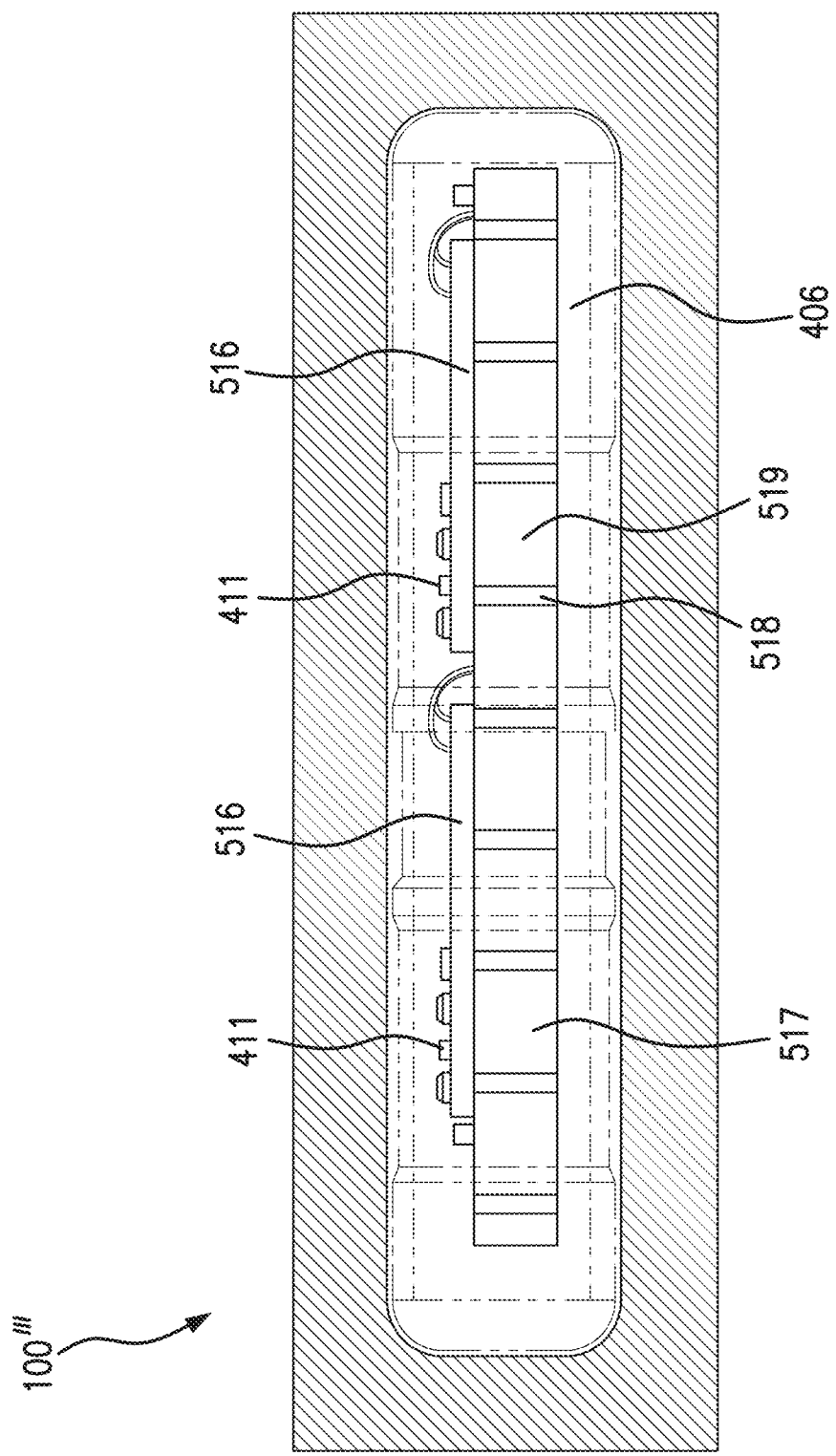

FIGS. 7A-7C are perspective, side, and cross-sectional views, respectively, of an implantable device 100" that is a second non-limiting example of the implantable device 100 of the system 50. FIGS. 7D, 7E, and 7F are perspective and side views, respectively, of an implantable device 100'" that is a third non-limiting example of the implantable device 100 of the system 50. In some embodiments, as shown in FIGS. 7A-7F, the implantable device 100 may include more than one substrate 516.

In some embodiments, as shown in FIGS. 7A-7C, the implantable device 100 may include one substrate 516 on one side of an inductive element 517 and another substrate 516 on an opposite side of the inductive element 517. Also, in some embodiments, as shown in FIGS. 7A-7C, the implantable device 100 may additionally or alternatively have one or more circuit components 722 (e.g., capacitors) mounted to the inductive element 517.

In some alternative embodiments, as shown in FIGS. 7D-7F, the implantable device 100 may include two or more substrates 516 on one side of an inductive element 517. In some non-limiting embodiments, as shown in FIG. 7E, one or more first internal photodetectors 407, one or more second internal photodetectors 408, and/or one or more internal analyte photodetectors 415 may be mounted on or fabricated in each of the two or more substrates 516. However, this is not required, and, in some alternative embodiments, the one or more first internal photodetectors 407 may be mounted on or fabricated in only one of the substrates 516, and the one or more second internal photodetectors 408 may be mounted on or fabricated in only another one of the substrates 516.

FIG. 7G is a schematic view illustrating the external device 101 and implantable device 100'" in use. In some embodiments, the one or more first external light sources 201 may emit first light 303 over the first wavelength range, and the one or more second external light source 202 may emit second light 304 over the second wavelength range. In some embodiments, the one or more first internal photodetectors 407 may output a first signal indicative of a received amount of the first light 303. In some embodiments, the one or more second internal photodetectors 408 may output a second signal indicative of a received amount of the second light 304. In some non-limiting embodiments, one or more first internal photodetectors 407 and one or more second internal photodetectors 408 may be mounted on or fabricated in each of the two or more substrates 516. However, this is not required, and, in some alternative embodiments, one or more first internal photodetectors 407 may be mounted on or fabricated in a first one of the substrates 516 (and not mounted on or fabricated in a second one of the substrates 516), and one or more second internal photodetectors 408 may be mounted on or fabricated in the second one of the substrates 516 (and not mounted on or fabricated in a first one of the substrates 516).

In some embodiments, the implantable device 100 may communicate with the external device 101. In some embodiments, the external device 101 may be an electronic device that communicates with the implantable device 100 to power the implantable device 100 and/or receive measurement data (e.g., photodetector and/or temperature sensor readings) from the implantable device 100. The measurement data may include one or more readings from one or more photodetectors 407, 408, 415 of the implantable device 100 and/or one or more readings from one or more temperature sensors of the analyte sensor 100. In some embodiments, the external device 101 may calculate analyte concentrations from the measurement data received from the implantable device 100. However, it is not required that the external device 101 perform the analyte concentration calculations itself, and, in some alternative embodiments, the external device 101 may instead convey/relay the measurement data received from the implantable device 100 to another device for calculation of analyte concentrations. In other alternative embodiments, the implantable device 100 may perform the analyte concentration calculations.

In some embodiments, the implantable device 100 may include an external interface. In some embodiments, the external interface may include an antenna. In some of alternative embodiments (e.g., transcutaneous embodiments), the external interface may include a wired connection between the implantable device 100 and the external device 101.

In some embodiments (e.g., embodiments in which the analyte sensor 100 is a fully implantable sensing system), the external device 101 may implement a passive telemetry for communicating with the implantable device 100 via an inductive magnetic link for power and/or data transfer. In some embodiments, as shown in FIGS. 5A, 5B, and 7A-7G, the external interface of the analyte sensor 100 may include an inductive element 517, which may be, for example, a ferrite based micro-antenna. In some embodiments, as shown in FIGS. 5A, 5B, 7C, 7F, and 7G, the inductive element 517 may include a conductor 518 in the form of a coil and a magnetic core 519. In some non-limiting embodiments, the core 519 may be, for example and without limitation, a ferrite core. In some embodiments, the inductive element 517 may be connected to circuitry (e.g., an application specification integrated circuit (ASIC)) of the implantable device 100. In some embodiments, the implantable device 100 may not include a battery, and, as a result, the implantable device 100 may rely on the external device 101 to provide power for the implantable device 100 of the system 105 and a data link to convey data from the implantable device 100 to the external device 101.

In some non-limiting embodiments, the external device 101 may provide energy to run the implantable device 100 via a magnetic field. In some embodiments, the magnetic external device-implantable device link can be considered as "weakly coupled transformer" type. In some non-limiting embodiments, the external device 101 and implantable device 100 may communicate using near field communication (e.g., at a frequency of 13.56 MHz, which can achieve high penetration through the skin and is a medically approved frequency band) for power transfer. However, this is not required, and, in other embodiments, different frequencies may be used for powering and communicating with the implantable device 100.

Although in some embodiments, as illustrated in FIGS. 1A, 1B, and 3-7G, the implantable device 100 may be a fully implantable sensor, this is not required, and, in some alternative embodiments, the implantable device 100 may be a transcutaneous device having a wired connection to the external device 101. For example, in some alternative embodiments, the implantable device 100 may be located in or on a transcutaneous needle (e.g., at the tip thereof). In these embodiments, instead of wirelessly communicating using inductive elements, the implantable device 100 and external device 101 may communicate using one or more wires connected between the external device 101 and the transcutaneous needle that includes the implantable device 100. For another example, in some alternative embodiments, the implantable device 100 may be located in a catheter (e.g., for intravenous blood glucose monitoring) and may communicate (wirelessly or using wires) with the external device 101.

In some embodiments, the one or more of the indicator element 409, light source(s) 411, photodetectors 407, 408, 415, circuit components, and substrate 516 of the implantable device 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, and U.S. application Ser. No. 14/142,017, filed on Dec. 27, 2013, all of which are incorporated by reference in their entireties. Similarly, the structure, function, and/or features of the sensor housing 406, implantable device 100, and/or external device 101 may be as described in one or more of U.S. application Ser. Nos. 13/761,839, 13/937,871, 13/650,016, and 14/142,017. For instance, the sensor housing 406 may have one or more hydrophobic, hydrophilic, opaque, and/or immune response blocking membranes or layers on the exterior thereof.

Figure 8:
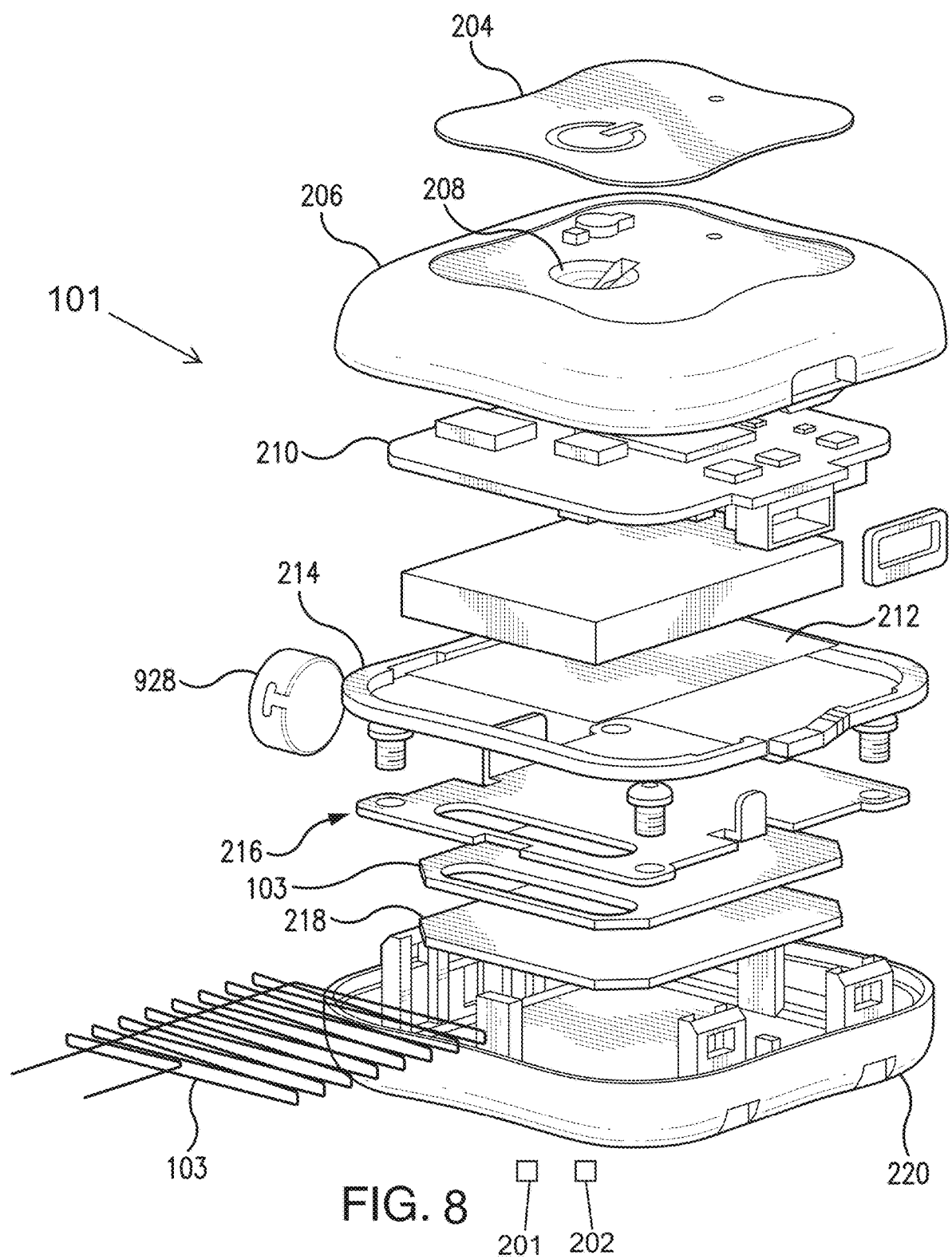
FIG. 8 is an exploded, perspective view of an external device including first and second external light sources and embodying aspects of the invention.

FIG. 8 is an exploded view illustrating a non-limiting embodiment of the external device 101, which may be included in the system 50 illustrated in FIG. 1A. As illustrated in FIG. 8, in some non-limiting embodiments, the external device 101 may include one or more of a first external light source 201, a second external light source 202, a graphic overlay 204, front housing 206, button 208, printed circuit board (PCB) assembly 210, battery 212, gaskets 214, antenna 103, frame 218, reflection plate 216, back housing 220, and vibration motor 928.

In some embodiments, as illustrated in FIG. 8, the antenna 103 may be contained within the housing 206 and 220 of the external device 101. In some embodiments, the antenna 103 in the external device 101 may be small and/or flat so that the antenna 103 fits within the housing 206 and 220 of a small, lightweight external device 101. In some embodiments, the antenna 103 may be robust and capable of resisting various impacts. In some embodiments, the external device 101 may be suitable for placement, for example, on an abdomen area, upper-arm, wrist, or thigh of a patient body. In some non-limiting embodiments, the external device 101 may be suitable for attachment to a patient body by means of a biocompatible patch. Although, in some embodiments, the antenna 103 may be contained within the housing 206 and 220 of the external device 101, this is not required, and, in some alternative embodiments, a portion or all of the antenna 103 may be located external to the housings 206 and 220. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 9:
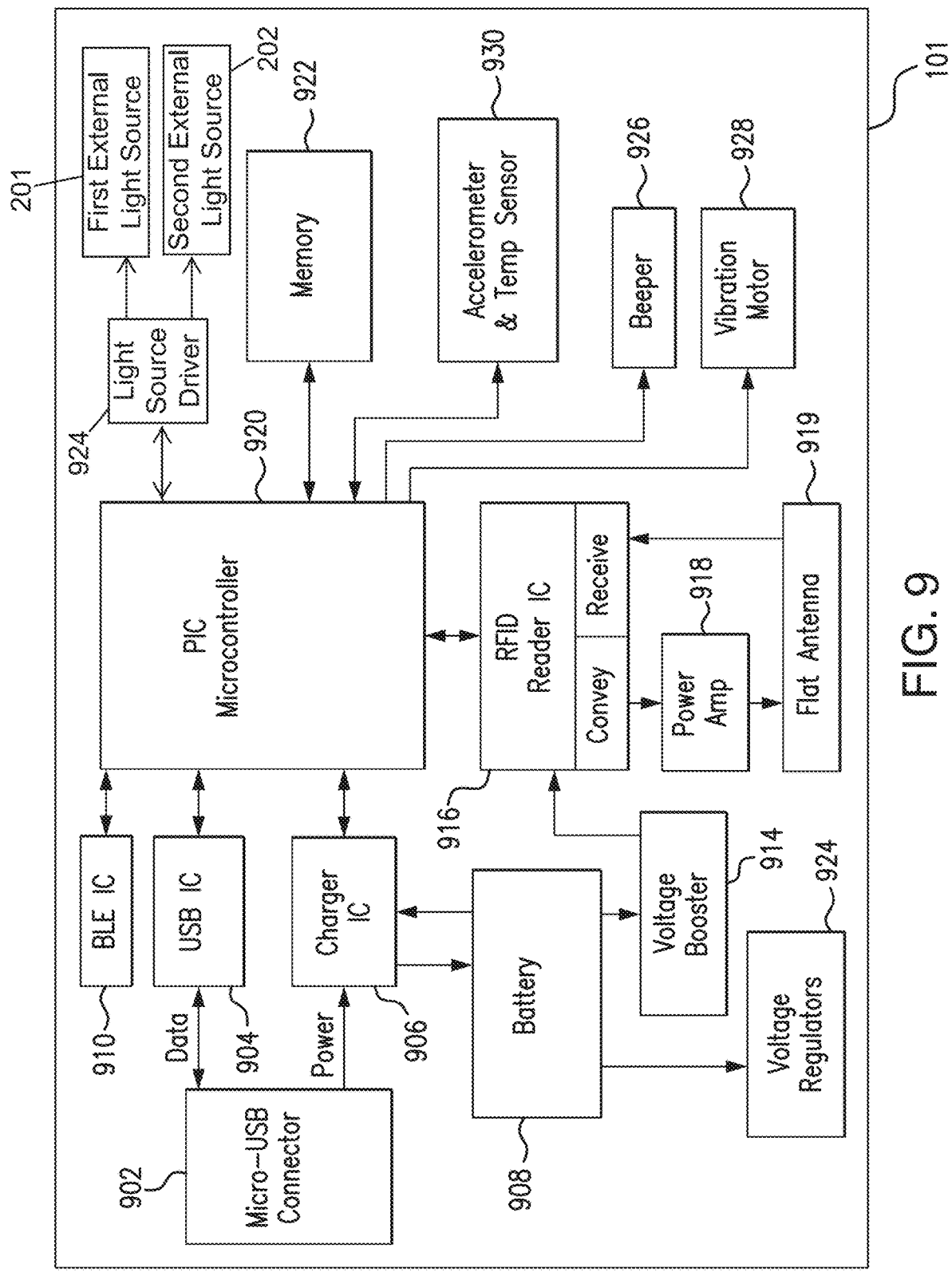
FIG. 9 is a schematic view illustrating an external device including first and second external light sources and embodying aspects of the present invention.

FIG. 9 is a schematic view of an external device 101 according to a non-limiting embodiment. In some embodiments, the external device 101 may have a connector 902, such as, for example, a Micro-Universal Serial Bus (USB) connector. The connector 902 may enable a wired connection to an additional device, such as a personal computer (e.g., personal computer 109) or a display device 107 (e.g., a smartphone).

The external device 101 may exchange data to and from the additional device through the connector 902 and/or may receive power through the connector 902. The external device 101 may include a connector integrated circuit (IC) 904, such as, for example, a USB-IC, which may control transmission and receipt of data through the connector 902.

The external device 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the external device 101 may include one or more connectors in addition to (or as an alternative to) Micro-USB connector 904. For example, in one alternative embodiment, the external device 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 107 (e.g., a smartphone) and/or to receive power, which may be used, for example, to charge the battery 908.

In some embodiments, the external device 101 may have a wireless communication IC 910, which enables wireless communication with an external device, such as, for example, one or more personal computers (e.g., personal computer 109) or one or more display devices 107 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0).

In some embodiments, the external device 101 may include a display interface device, which may enable communication by the external device 101 with one or more display devices 107. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the external device 101 may include voltage regulators 912 and/or a voltage booster 914. The battery 908 may supply power (via voltage booster 914) to radio-frequency identification (RFID) reader IC 916, which may use the inductive element 103 to convey information (e.g., commands) to the implantable device 100 and receive information (e.g., measurement information) from the implantable device 100. In some non-limiting embodiments, the implantable device 100 and external device 101 may communicate using near field communication (NFC) (e.g., at a frequency of 13.56 MHz). In the illustrated embodiment, the inductive element 103 is a flat antenna 919. In some non-limiting embodiments, the antenna may be flexible. However, as noted above, the inductive element 103 of the external device 101 may be in any configuration that permits adequate field strength to be achieved when brought within adequate physical proximity to the inductive element 114 of the implantable device 100. In some embodiments, the external device 101 may include a power amplifier 918 to amplify the signal to be conveyed by the inductive element 103 to the implantable device 100.

In some embodiments, the external device 101 may include a peripheral interface controller (PIC) controller 920 and memory 922 (e.g., Flash memory), which may be non-volatile and/or capable of being electronically erased and/or rewritten. The PIC controller 920 may control the overall operation of the external device 101. For example, the PIC controller 920 may control the connector IC 904 or wireless communication IC 910 to transmit data via wired or wireless communication and/or control the RFID reader IC 916 to convey data via the inductive element 103. The PIC controller 920 may also control processing of data received via the inductive element 103, connector 902, or wireless communication IC 910.

In some embodiments, the transceiver 101 may include an interface device, which may enable communication by the external device 101 with an implantable device 100. In some embodiments, the interface device may include the inductive element 103. In some non-limiting embodiments, the interface device may additionally include the RFID reader IC 916 and/or the power amplifier 918. However, in some alternative embodiments where there exists a wired connection between the implantable device 100 and the external device 101 (e.g., transcutaneous embodiments), the interface device may include the wired connection.

In some embodiments, the external device 101 may include a speaker 926 (e.g., a beeper) and/or vibration motor 928, which may be activated, for example, in the event that an alarm condition (e.g., detection of a hypoglycemic or hyperglycemic condition) is met. The external device 101 may also include one or more additional sensors 930, which may include an accelerometer and/or temperature sensor, that may be used in the processing performed by the PIC controller 920.

In some embodiments, as shown in FIG. 9, the external device 101 may include a light source driver 924. In some embodiments, the light source driver 924 may drive one or more of the first and second external light sources 201 and 202 to emit the first and second light 303 and 304, respectively. In some embodiments, the light source driver 924 may drive one or more of the first and second light sources 201 and 202 under the control of the PIC controller 920.

In some embodiments, the external device 101 (e.g., the PIC controller 920 and/or light source driver 924 of the external device 101) may be configured such that the first and second external light sources 201 and 202 emit the first light 303 and second light 304 simultaneously. FIGS. 3 and 7G show non-limiting examples where the first and second external light sources 201 and 202 emit the first and second light 303 and 304 simultaneously. However, this is not required, and, in some alternative embodiments, the external device 101 (e.g., the PIC controller 920 and/or light source driver 924 of the external device 101) may be configured such that the first and second external light sources 201 and 202 emit the first light 303 and second light 304 at different times. For example, the one or more first external light sources 201 may emit the first light 303 during first time periods, and the one or more second external light source 202 may emit the second light 304 during second time periods that are different than the first time periods. In one non-limiting embodiment, the external device 101 may cycle through the first and second time periods multiple times (e.g., 30 times) during a measurement period (e.g., 1 second). In some non-limiting embodiments, the cycle may additionally include third time periods during which both the first and second external light sources 201 and 202 are off.

Figure 10A:
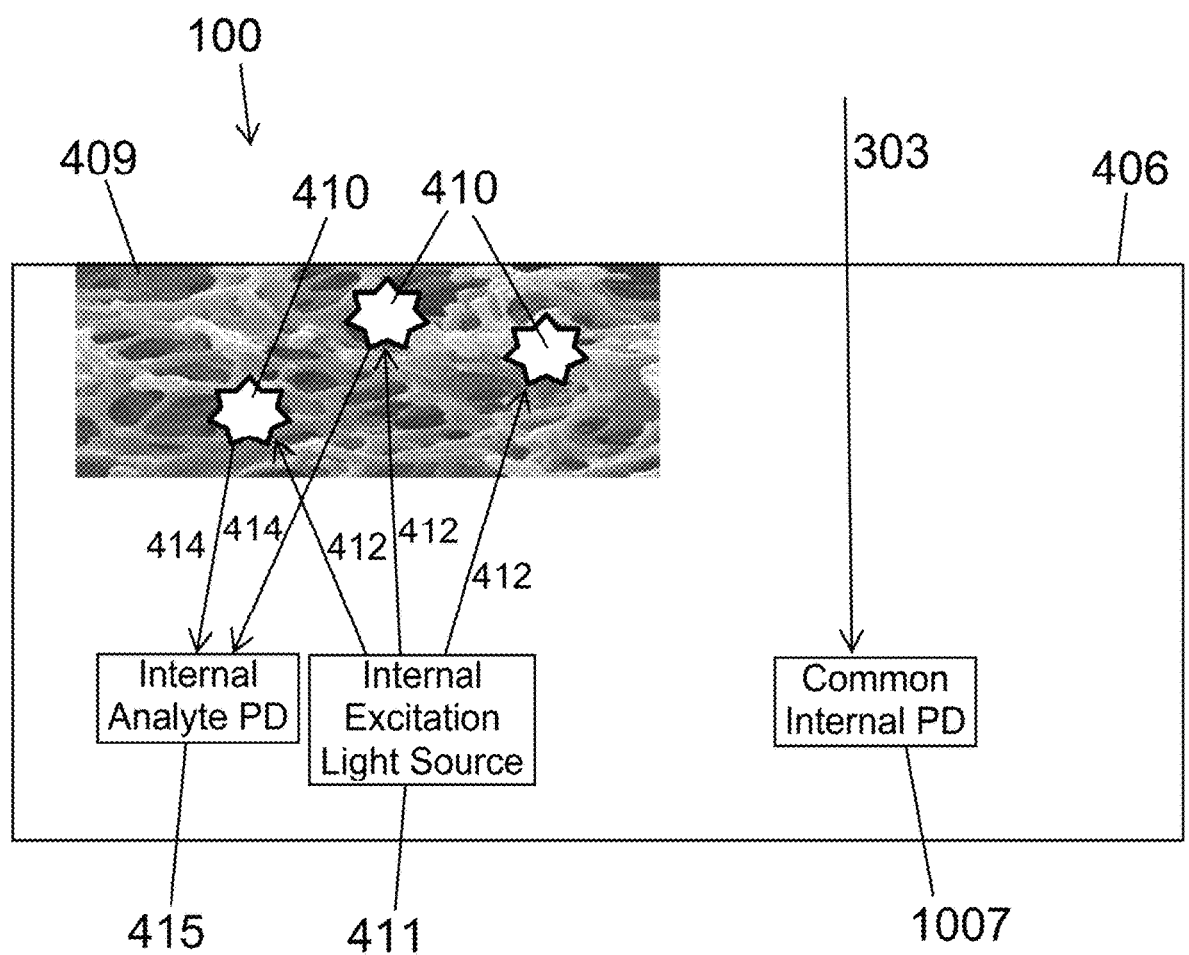
FIGS. 10A and 10B are schematic views of an implantable device including a common internal photodetector and embodying aspects of the present invention.
Figure 10B:
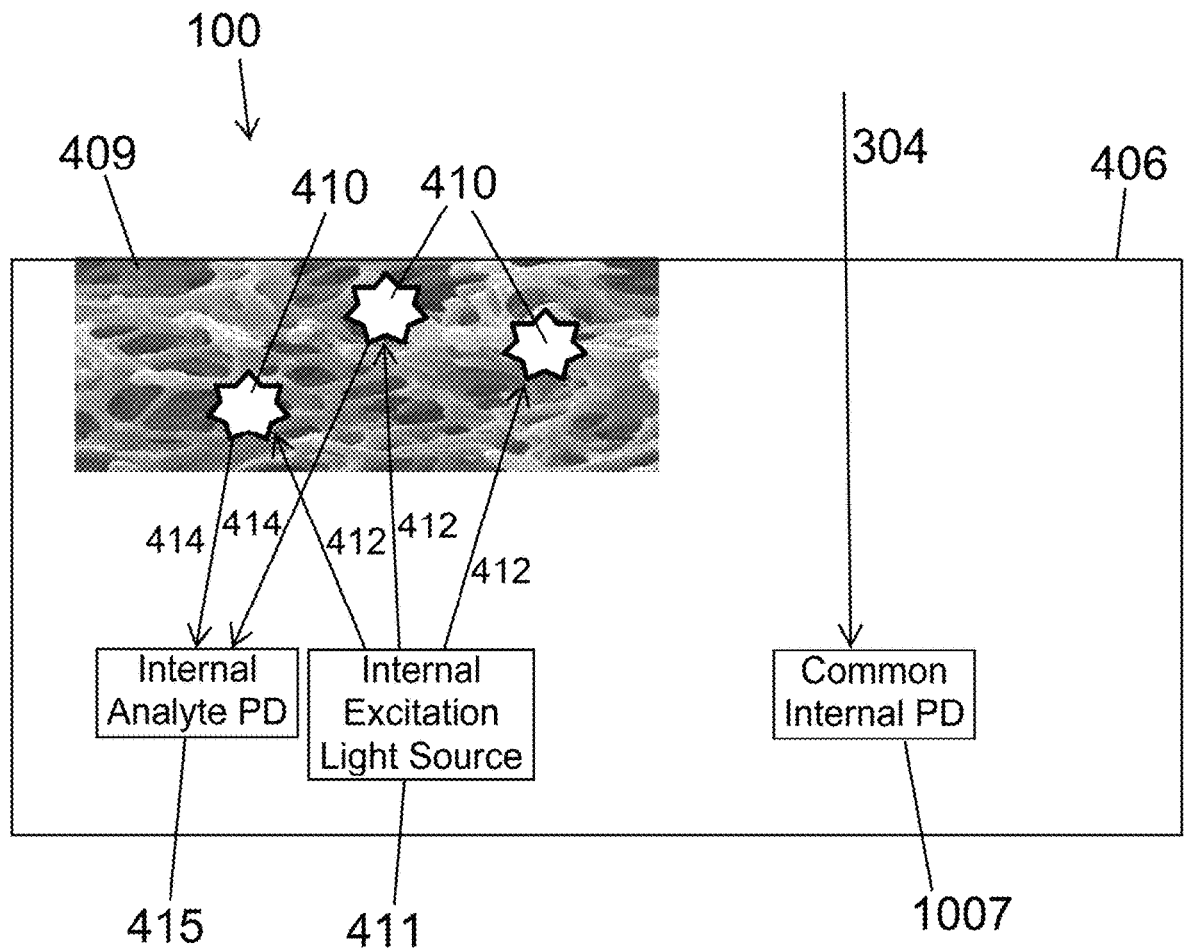

In some of the non-simultaneous alternative embodiments, as shown in FIG. 4 (and FIGS. 5B, 6, and 7E), the implantable device 100 may include first and second internal photodetectors 407 and 408 that output first and second signals, respectively, in accordance with the received amount of the first and second light 303 and 304, respectively. However, this is not required, and, in some other non-simultaneous alternative embodiments, as illustrated in FIGS. 10A and 10B, the implantable device 100 may instead include one or more common internal photodetectors 1007.

In some embodiments, the one or more common internal photodetectors 1007 may be mounted on or fabricated in one or more substrates 516 of the implantable device 100.

In some embodiments, the one or more common internal photodetectors 1007 may be configured to output a first signal during a first time period during which the one or more first external light sources 201 emit first light 303 and to output a second signal during a second time period during which the one or more second external light sources 202 emit second light 304. The first signal may be indicative of the amount of first light 303 received by the one or more common internal photodetectors 1007 during the first time period, and the second signal may be indicative of the amount of second light 304 received by the one or more common internal photodetectors 1007 during the second time period. In some non-limiting embodiments, the one or more common internal photodetectors 1007 may be configured to output the first and second signals because one or more optical filters may allow light within a wavelength range including the first and second wavelength ranges of the first and second light 303 and 304 to pass through while preventing light outside the wavelength range from reaching the one or more common photodetectors 1007. FIG. 10A shows a common internal photodetector 1007 receiving the first light 303 during a first period, and FIG. 10B shows the common internal photodetector 1007 receiving the second light 304 during a second period.

In some embodiments, the interface device of the external device 101 (e.g. the inductive element 103) may be configured to receive data from the implantable device 101. In some embodiments, the received data may include one or more of a first measurement indicative of the amount of the first light 303 received by the first internal photodetector 407 (or by the common internal photodetector 1007) of the implantable device 100, a second measurement indicative of the amount of second light 304 received by the second internal photodetector 408 (or by the common internal photodetector 1007), an analyte measurement indicative of the amount of emission light 414 received by the internal analyte photodetector 415, and a temperature measurement indicative of a temperature within the implantable device 100. In some embodiments, the external device 101 (e.g., the PIC controller 920 of the external device 101) may be configured to calculate an analyte level using at least one or more of the first, second, analyte, and temperature measurements. In some embodiments, the external device 101 (e.g., the PIC controller 920 of the external device 101) may be additionally or alternatively configured to calculate an amount or volume of blood in a pocket around the implantable device 101 using at least one or more of the first and second measurements.

Figure 11:
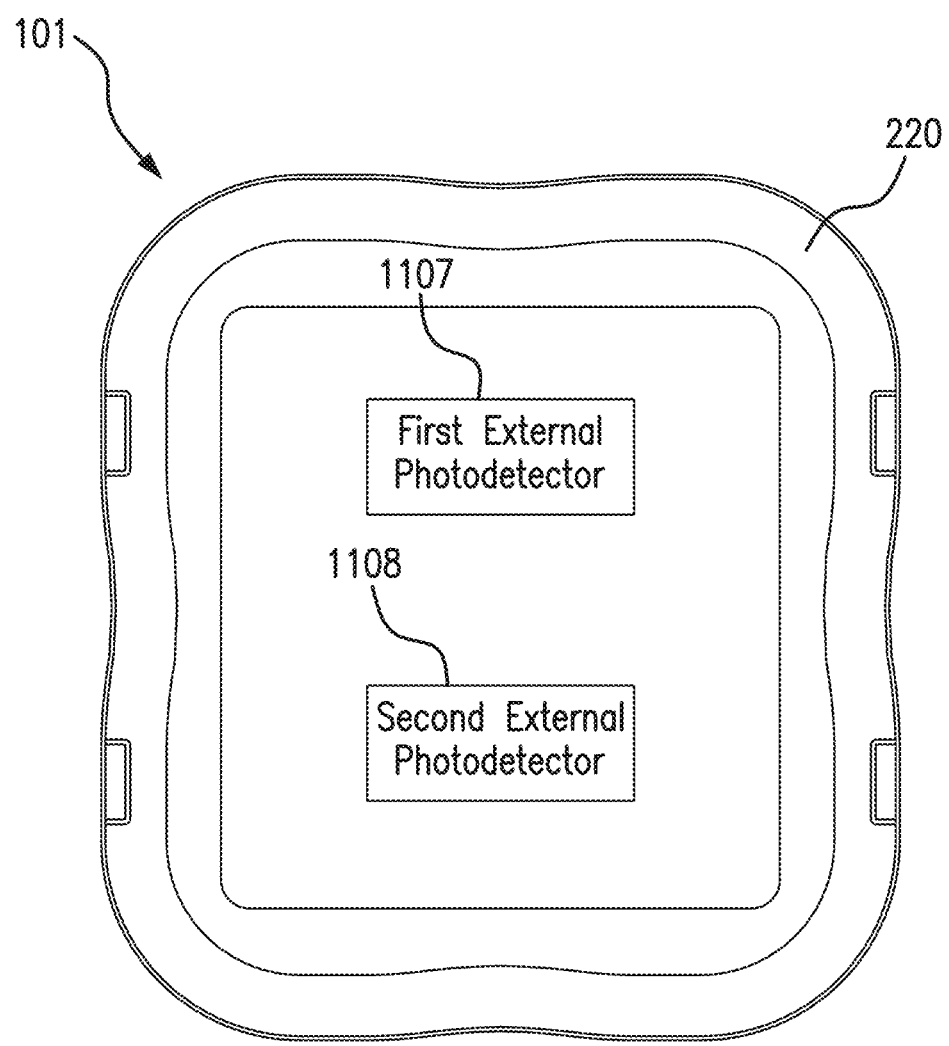
FIG. 11 is a back view of an external device including first and second external photodetectors and embodying aspects of the present invention.

FIG. 11 is a back view illustrating a non-limiting embodiment of an external device 101 embodying aspects of the present invention and which may be included in the system 50 shown in FIG. 1. In some embodiments, as shown in FIG. 11, the external device 101 may include a housing 220, which may be a back housing. In some embodiments, as shown in FIG. 11, the external device 101 may include one or more external photodetectors (e.g., photodiodes, phototransistors, photoresistors, or other photosensitive elements). In some embodiments, the one or more photodetectors of the external device 101 may include one or more first external photodetectors 1107. In some embodiments, the one or more photodetectors of the implantable device 100 may include one or more second external photodetectors 1108.

Figure 12:
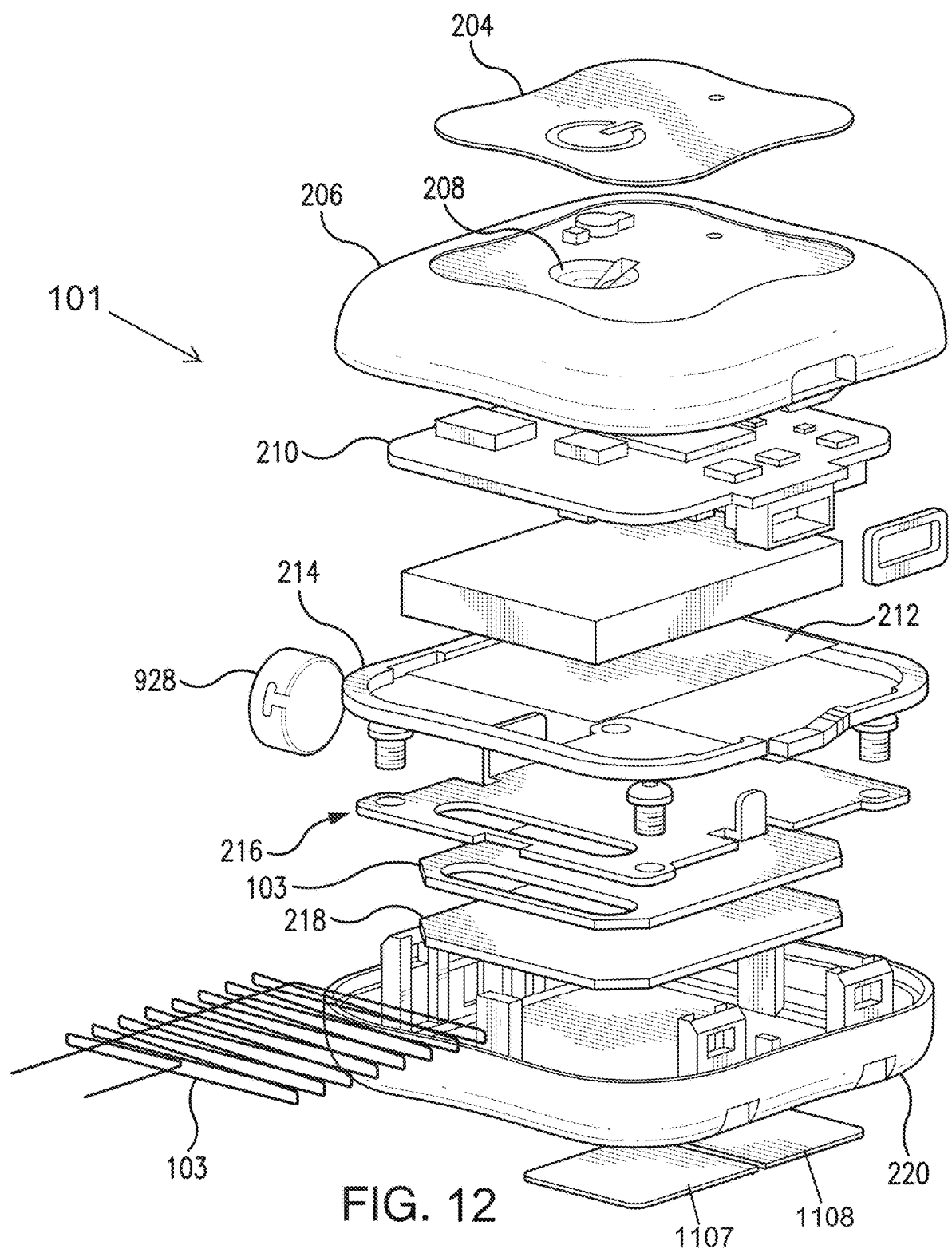
FIG. 12 is an exploded, perspective view of an external device including first and second external photodetectors and embodying aspects of the invention.

FIG. 12 is an exploded view illustrating the non-limiting embodiment of the external device 101 having one or more external photodetectors and embodying aspects of the present invention. In some non-limiting embodiments, as illustrated in FIG. 12, the external device 101 may include one or more of a first external photodetector 1107, a second external photodetector 1108, a graphic overlay 204, front housing 206, button 208, printed circuit board (PCB) assembly 210, battery 212, gaskets 214, antenna 103, frame 218, reflection plate 216, back housing 220, and vibration motor 928.

Figure 13:
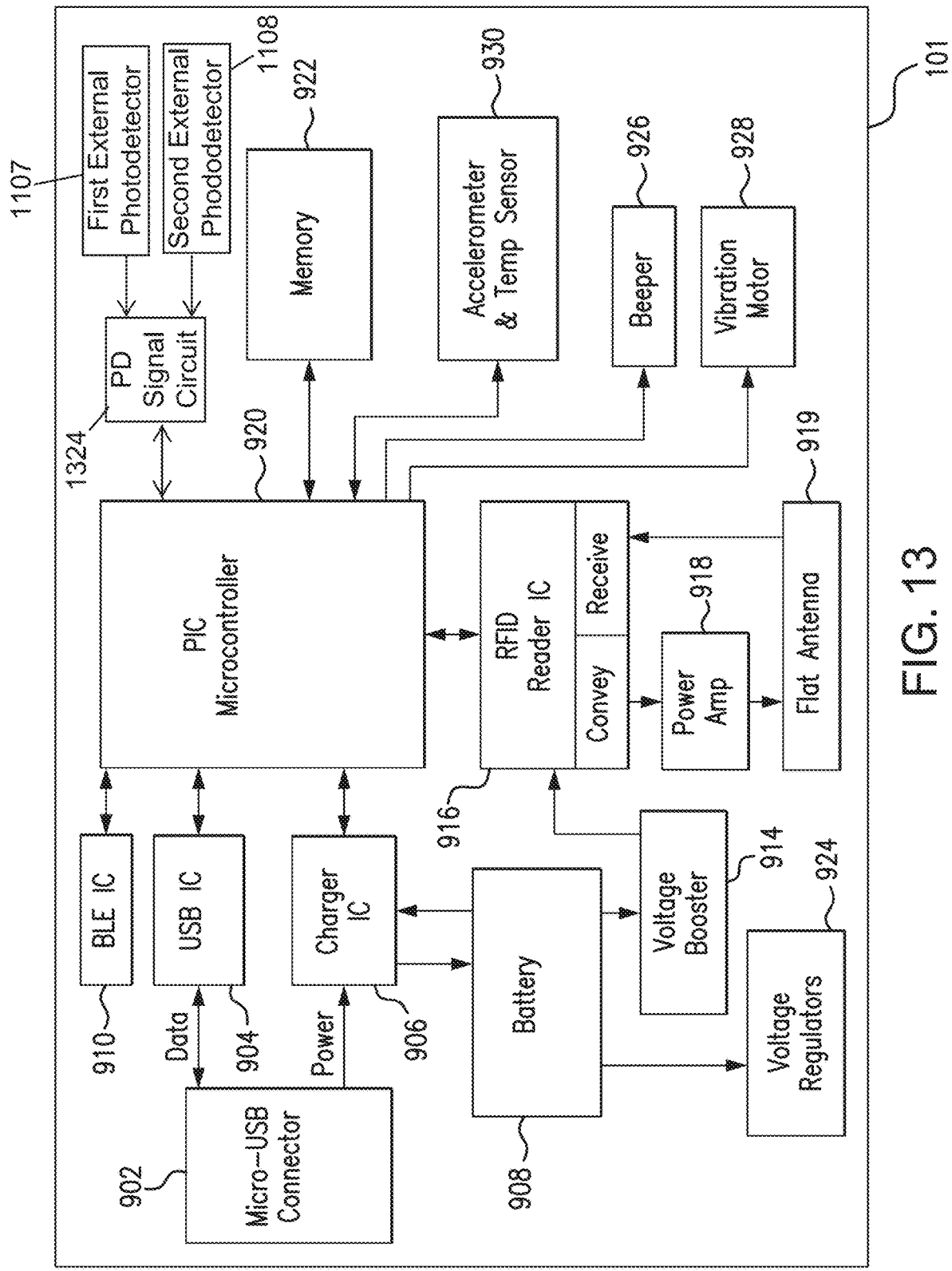
FIG. 13 is a schematic view illustrating an external device including first and second external photodetectors and embodying aspects of the present invention.

FIG. 13 is a schematic view illustrating the non-limiting embodiment of the external device 101 having one or more external photodetectors and embodying aspects of the present invention. In some embodiments, as shown in FIG. 13, the external device 101 may include a photodetector signal processing circuit 1324. In some embodiments, the photodetector signal processing circuit 1324 may process one or more of a first signal output by the first external photodetector 1107 and a second signal output by the second external photodetector 1108. In some embodiments, the photodetector signal processing circuit 1324 may include one or more amplifiers, one or more current-to-voltage converters, and/or one or more analog-to-digital convertors. In some embodiments, the photodetector signal processing circuit 1324 may convert one or more of the first signal output by the first external photodetector 1107 and the second signal output by the second external photodetector 1108 to digital signals for further processing by the PIC microcontroller 920.

Figure 14A:
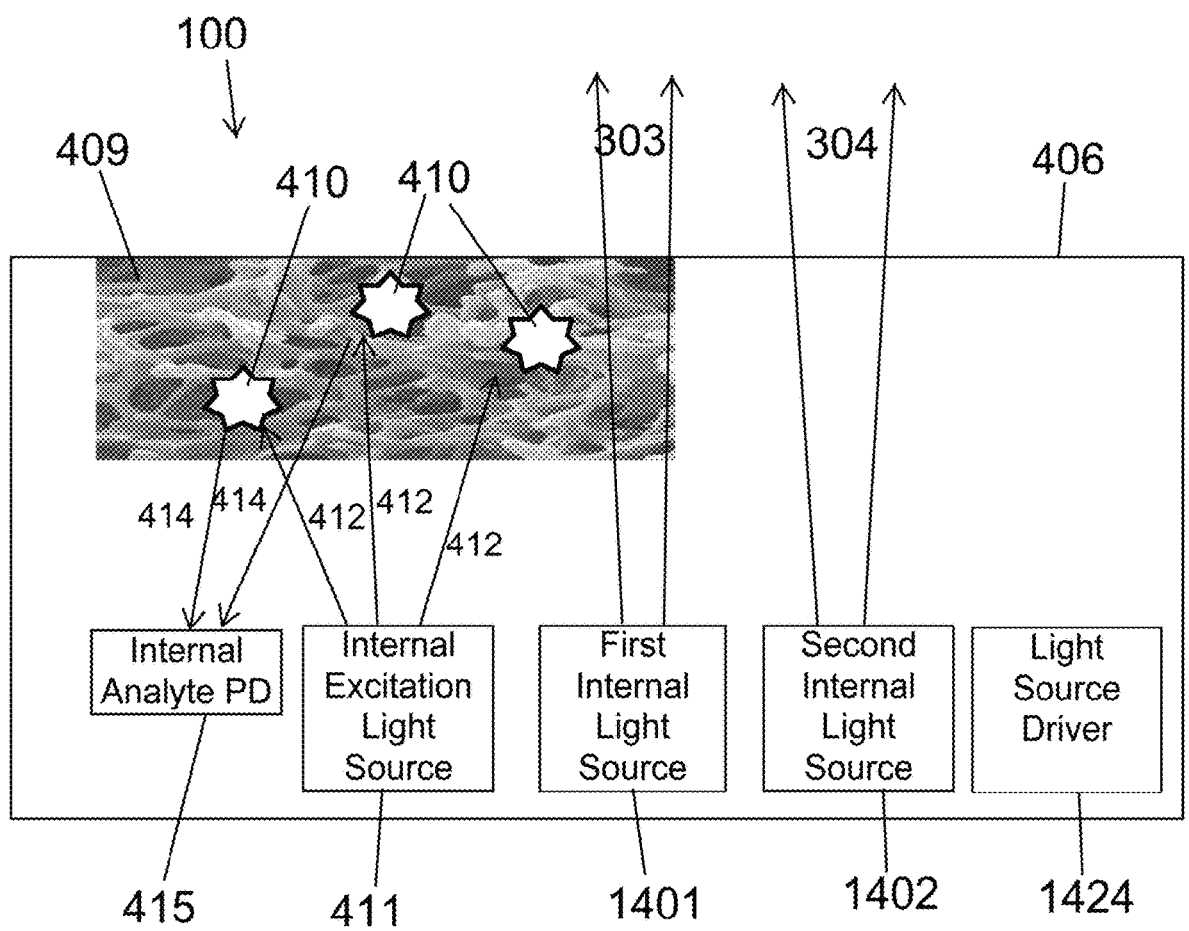
FIG. 14A is a schematic view of an implantable device including first and second internal light sources and embodying aspects of the present invention.

FIG. 14A is a schematic view illustrating an implantable device 100 embodying aspects of the present invention. In some embodiments, the implantable device 100 may include one or more first internal light sources 1401 configured to emit first light 303. In some embodiments, the implantable device 100 may include one or more second internal light sources 1402 configured to emit second light 304.

In some embodiments, the implantable device 100 may be implanted in the tissue of a living animal, and the external device 101 may be external to the tissue. In some embodiments, the back of the external device 101 may be adjacent to the tissue (e.g., adjacent to the skin of the living animal). In some embodiments, one or more of the first and second internal light sources 1401 and 1402 of the implantable device 101 may emit the first light 303 and/or the second light 304, which may pass out of the implantable device 100. Some or all of the first and second light 303 and 304 may pass through any blood and/or clotting in a pocket in the tissue surrounding the implantable device 100, through the tissue, and reach one or more photodetectors of the external device 101.

In some non-limiting embodiments, the one or more first external photodetectors 1107 of the external device 101 may be configured to output a first signal indicative of an amount of the first light 303 received by the one or more first external photodetectors 1107. In some non-limiting embodiments, the one or more first external photodetectors 1107 may be configured to output a first signal indicative of an amount of the first light 303 received by the one or more first external photodetectors 1107 because one or more optical filters may prevent light outside the first wavelength range (i.e., light outside the wavelength range of the first light 303 emitted by the first internal light source 1401) from reaching the one or more first external photodetectors 1107. In some embodiments, the first signal may vary in accordance with the amount of blood and/or clotting in the pocket. In some non-limiting embodiments, the first signal may vary in accordance with the amount of deoxygenated hemoglobin in the pocket.

In some embodiments, the one or more second external photodetectors 1108 may be configured to output a second signal indicative of an amount of the second light 304 received by the one or more second external photodetectors 1108. In some non-limiting embodiments, the one or more second external photodetectors 1108 may be configured to output a second signal indicative of an amount of the second light 304 received by the one or more second external photodetectors 1108 because one or more optical filters may prevent light outside the second wavelength range (i.e., light outside the wavelength range of the second light 304 emitted by the second internal light source 1402) from reaching the one or more second external photodetectors 1108. In some embodiments, the second signal may vary in accordance with the amount of blood and/or clotting in the pocket. In some non-limiting embodiments, second signal may vary in accordance with the amount of oxygenated hemoglobin in the pocket.

In some embodiments, the amount of the first light 303 that passes through any blood and/or clotting in the pocket may vary in accordance with the amount of blood and/or clotting in the pocket. In some non-limiting embodiments, the amount of the first light 303 that passes through any blood and/or clotting in the pocket may vary in accordance with the amount of deoxygenated hemoglobin in the pocket. In some embodiments, the amount of the second light 304 that passes through any blood and/or clotting in the pocket may vary in accordance with the amount of blood and/or clotting in the pocket. In some non-limiting embodiments, the amount of the second light 304 that passes through any blood and/or clotting in the pocket may vary in accordance with the amount of oxygenated hemoglobin in the pocket.

In some embodiments, the implantable device 100 may include one or more light source drivers 1424. In some embodiments, the one or more light source drivers 1424 may be mounted on or fabricated in one or more substrates 516 of the implantable device 100 (e.g., one light source driver 1424 per substrate 516). In some embodiments, the one or more light source drivers 1424 may drive one or more of the first and second internal light sources 1401 and 1402 to emit the first and second light 303 and 304, respectively. In some embodiments, the one or more light source drivers 1424 may drive one or more of the first and second light sources 1401 and 1402 under the control of one or more measurement controllers (e.g., a measurement controller may be mounted on or fabricated on each substrate 516 and may control any light source driver 1424 mounted on or fabricated on the same substrate 516). In some non-limiting embodiments, all or a portion of one or more of the light source driver 1424 and the measurement controller may be included in the circuit components 620 fabricated in a semiconductor substrate 516 of the implantable device 100 (see FIG. 6).

Figure 14C:
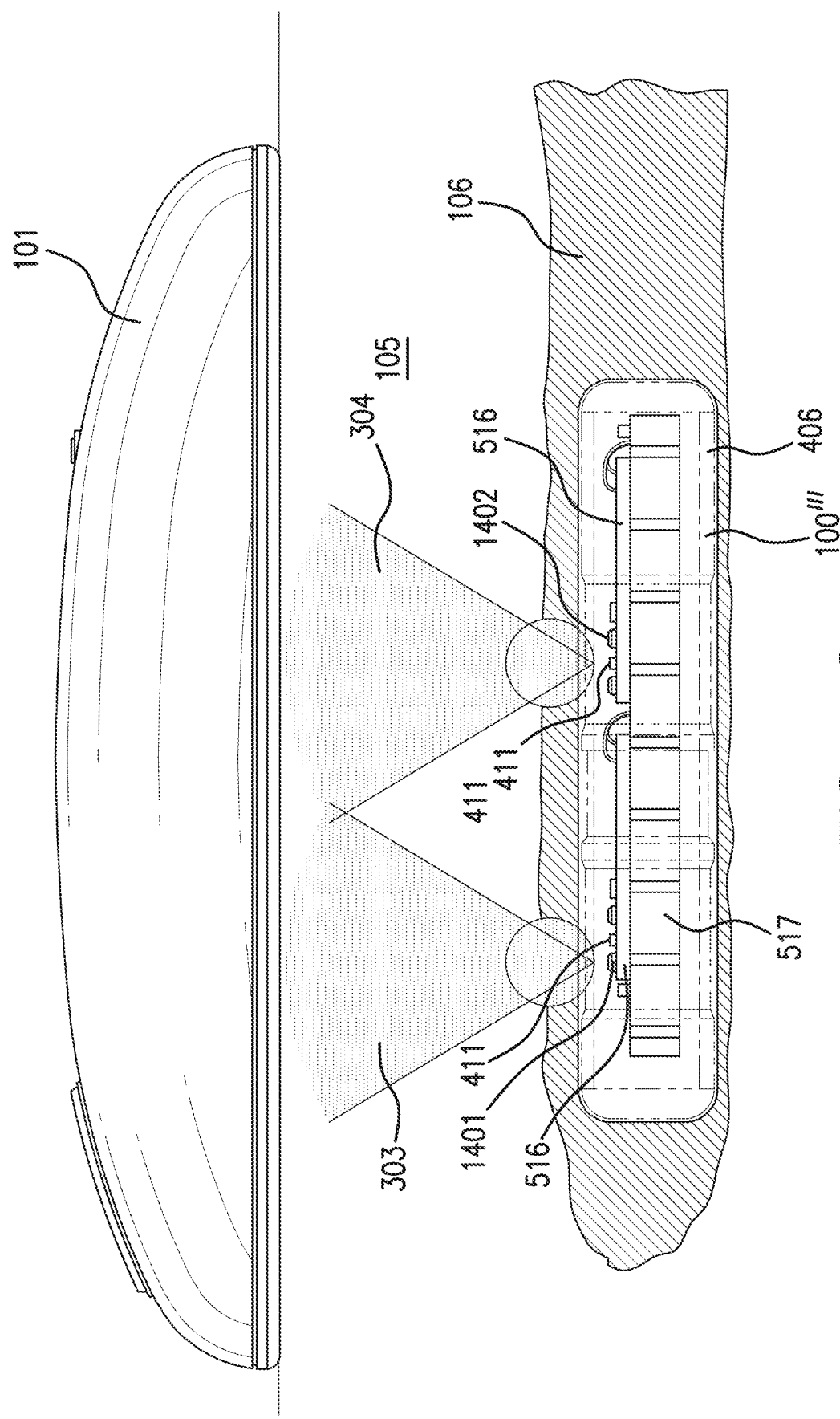

In some embodiments, the implantable device 100 may include two or more substrates 516 (e.g., on opposite sides of the inductive element 517 as shown in FIGS. 7A-7C or on the same side of the inductive element 517 as shown in FIGS. 7D-7F). In some non-limiting embodiments, as shown in FIG. 14B, one or more first internal light sources 1401 and one or more second internal light sources 1402 may be mounted on or fabricated in one of the substrates 516. In some alternative embodiments, as shown in FIG. 14C, one or more first internal light sources 1401 may be mounted on or fabricated in one of the substrates 516, and one or more second internal lights sources 1402 may be mounted on or fabricated in another one of the substrates. In some alternative embodiments, one or more first internal light sources 1401 and one or more second internal light sources 1402 may be mounted on or fabricated in each of the substrates 516.

In some embodiments, the implantable device 100 (e.g., the measurement controller(s) and/or light source driver(s) 1424 of the implantable device 100) may be configured such that the first and second internal light sources 1401 and 1402 emit the first light 303 and second light 304 simultaneously. FIGS. 14A-14C shows an example where the first and second internal light sources 1401 and 1402 emit the first and second light 303 and 304 simultaneously. However, this is not required, and, in some alternative embodiments, the implantable device 100 (e.g., the measurement controller(s) and/or light source driver(s) 1424 of the implantable device 100) may be configured such that the first and second internal light sources 1401 and 1402 emit the first light 303 and second light 304 at different times. For example, the one or more first internal light sources 1401 may emit the first light 303 during first time periods, and the one or more second internal light source 1402 may emit the second light 304 during second time periods that are different than the first time periods. In one non-limiting embodiment, the implantable device 100 may cycle through the first and second time periods multiple times (e.g., 30 times) during a measurement period (e.g., 1 second). In some non-limiting embodiments, the cycle may additionally include third time periods during which both the first and second internal light sources 1401 and 1402 are off.

Figure 15:
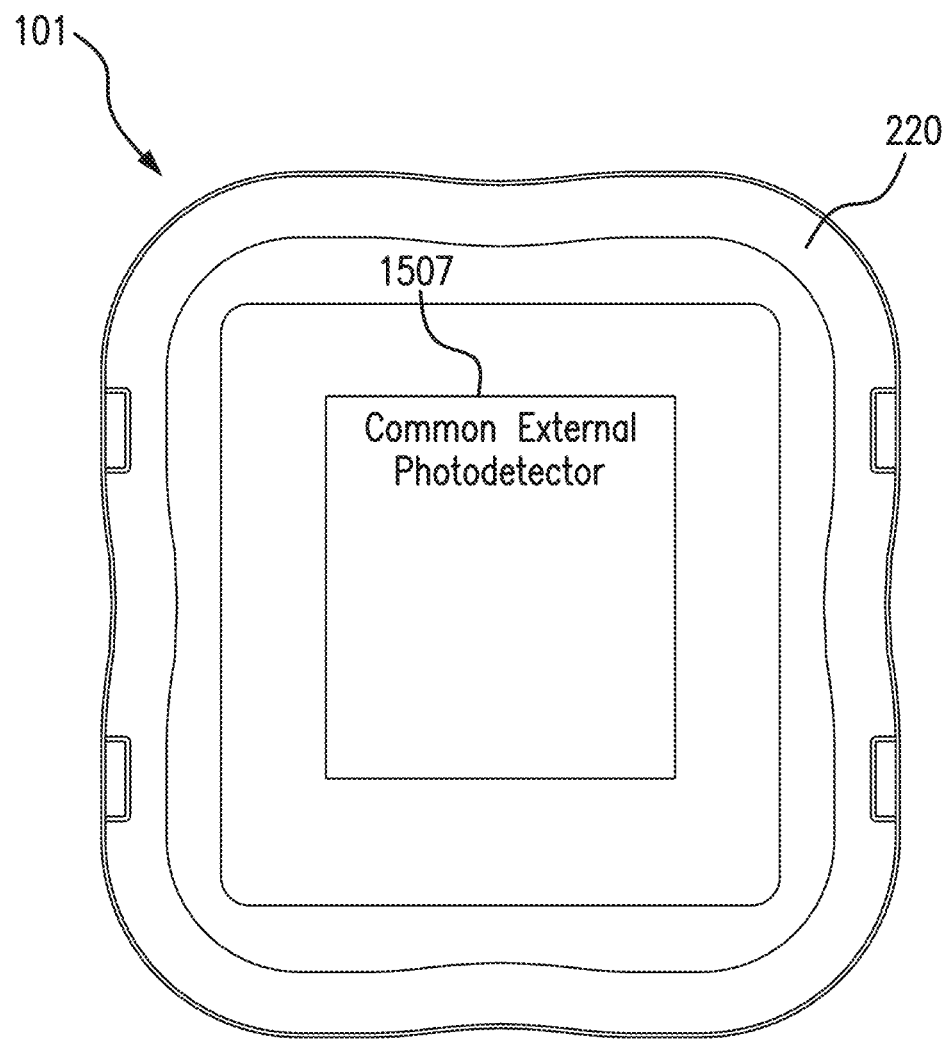
FIG. 15 is a back view of an external device including a common external photodetector and embodying aspects of the present invention.
Figure 16:
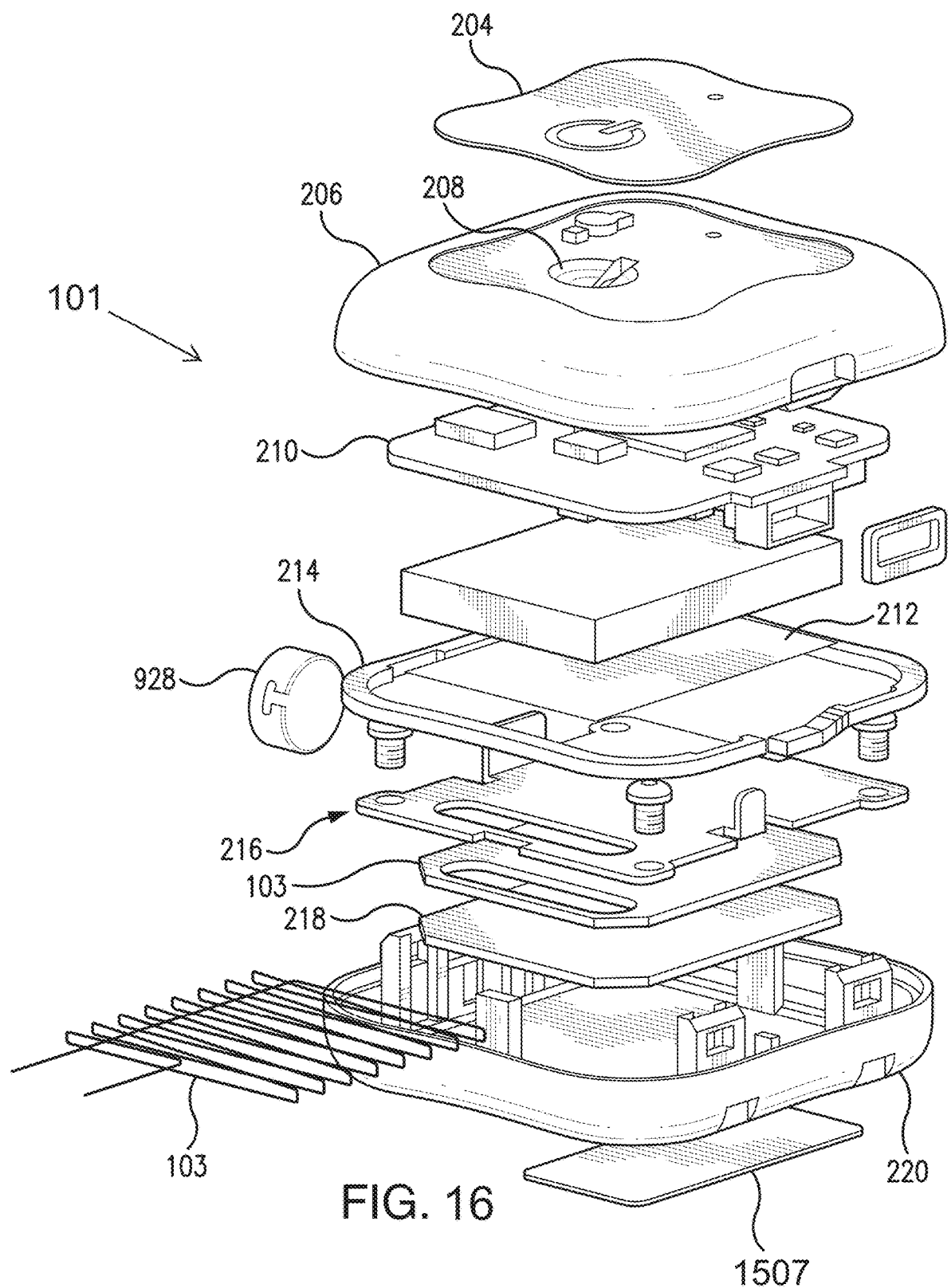
FIG. 16 is an exploded, perspective view of an external device including a common external photodetector and embodying aspects of the invention.
Figure 17:
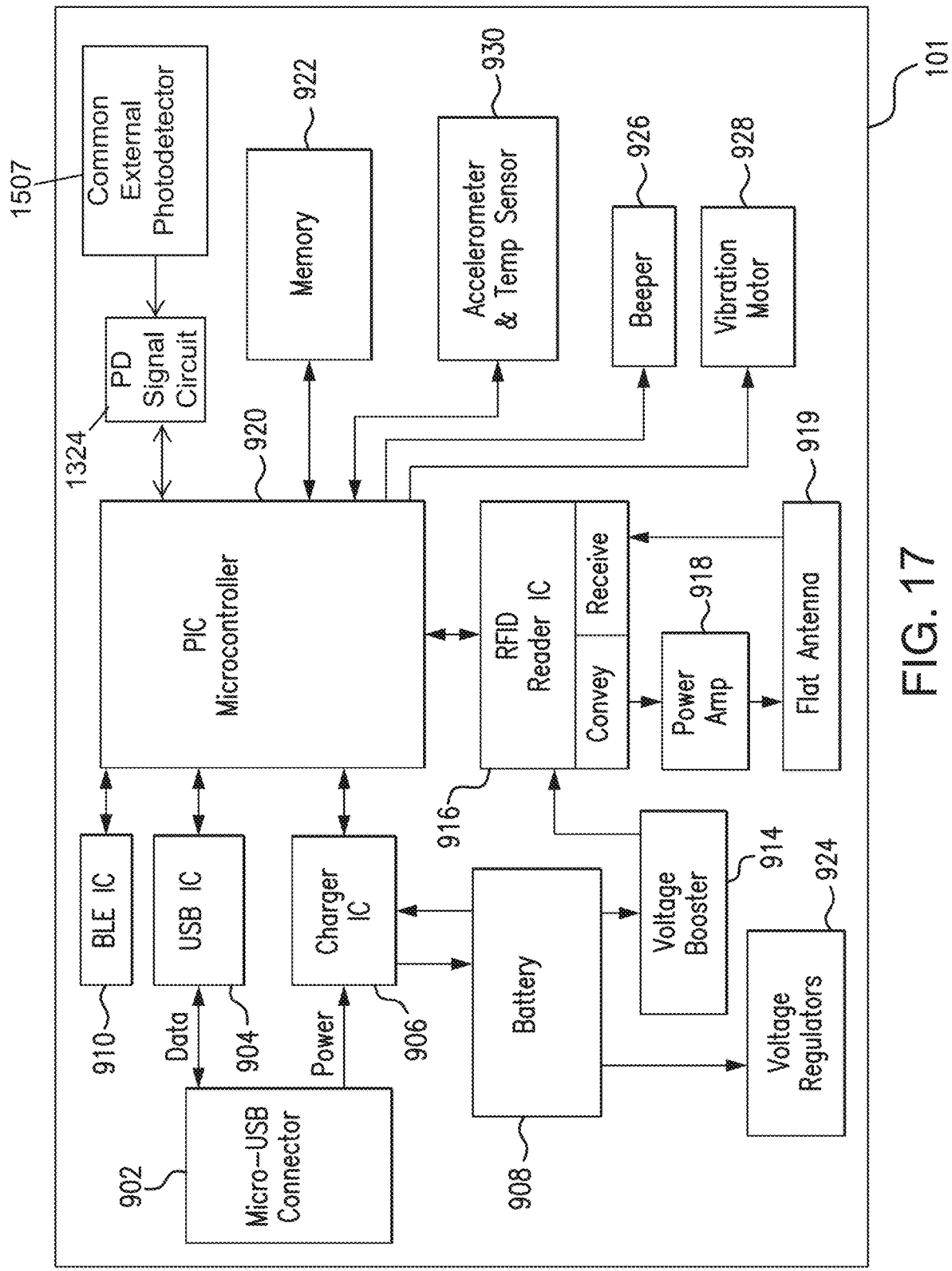
FIG. 17 is a schematic view illustrating an external device including a common external photodetector and embodying aspects of the present invention.

In some of the non-simultaneous alternative embodiments, as shown in FIGS. 11-13, the external device 101 may include first and second external photodetectors 1107 and 1108 that output first and second signals, respectively, in accordance with the received amount of the first and second light 303 and 304, respectively. However, this is not required, and, in some other non-simultaneous alternative embodiments, as illustrated in FIGS. 15-17, the external device 101 may instead include one or more common internal photodetectors 1507. FIGS. 15-17 are back, exploded, and schematic views, respectively, of a non-limiting embodiment of an external device 101 that includes one or more common internal photodetectors 1507.

Figure 18A:
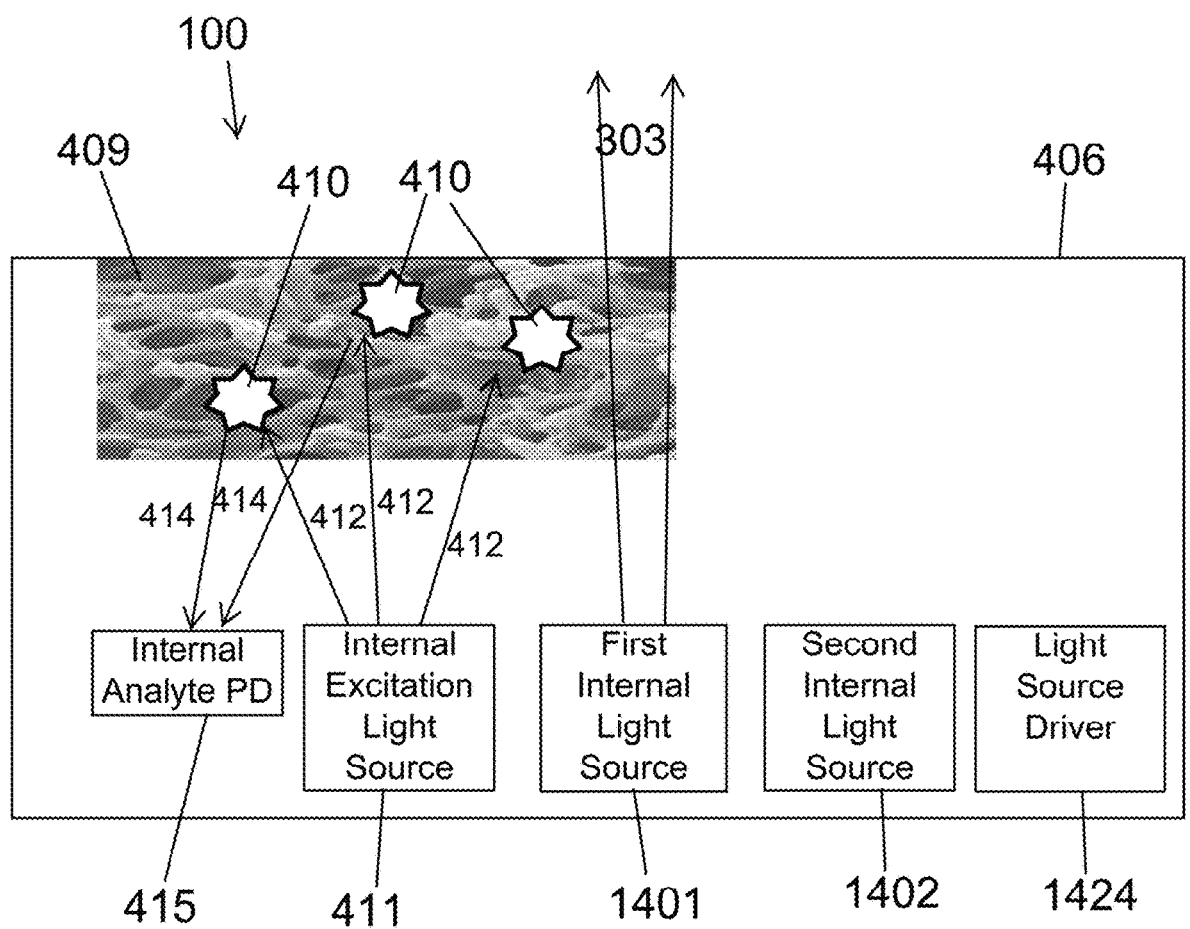
FIGS. 18A and 18B are schematic views of an implantable device including first and second light sources and embodying aspects of the present invention.
Figure 18B:
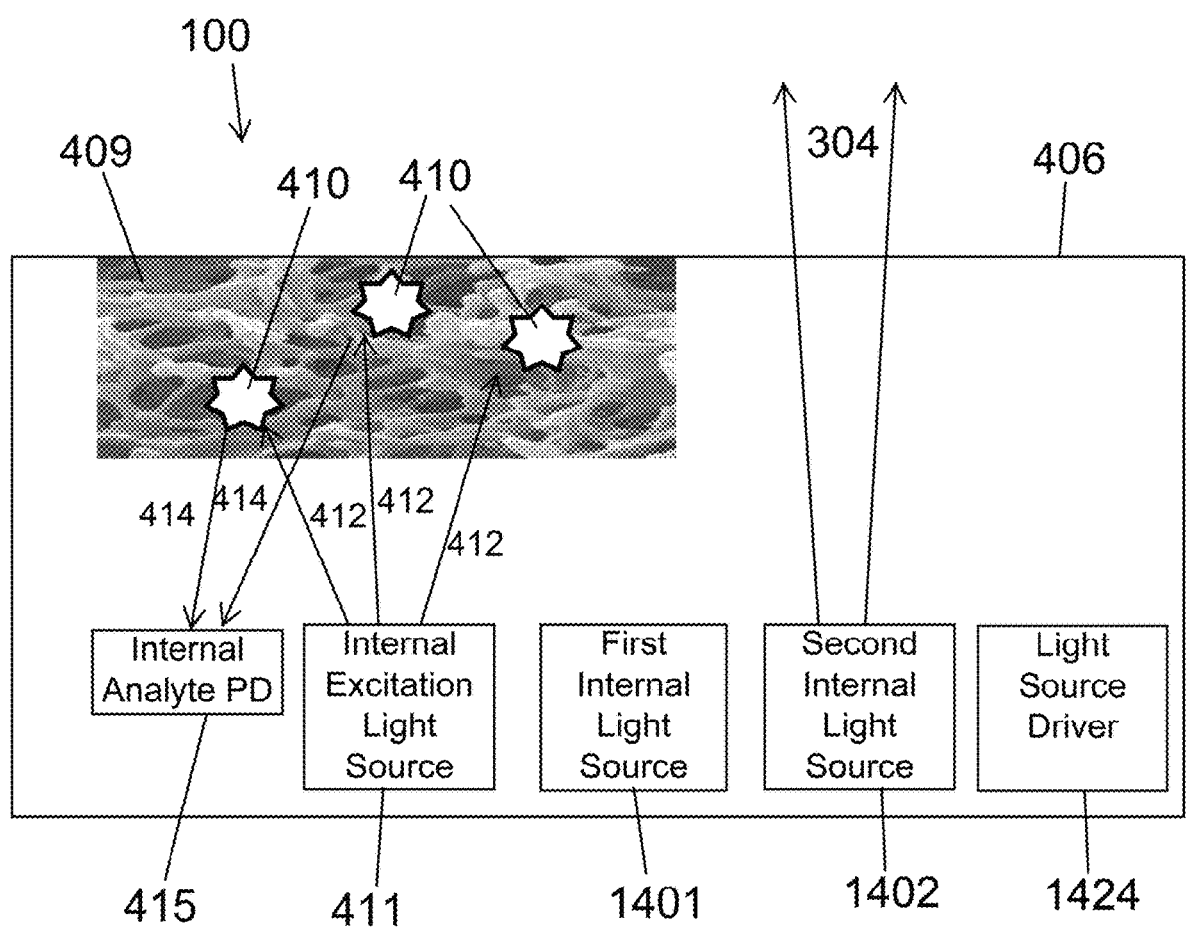

In some embodiments, the one or more common external photodetectors 1507 may be configured to output a first signal during a first time period during which the one or more first internal light sources 1401 emit first light 303 and to output a second signal during a second time period during which the second internal light source 1402 emits second light 304. The first signal may be indicative of the amount of first light 303 received by the one or more common external photodetectors 1507 during the first time period, and the second signal may be indicative of the amount of second light 304 received by the one or more common external photodetectors 1507 during the second time period. In some non-limiting embodiments, the one or more common external photodetectors 1507 may be configured to output the first and second signals because one or more optical filters may allow light within a wavelength range including the first and second wavelength ranges of the first and second light 303 and 304 to pass through while preventing light outside the wavelength range from reaching the one or more common external photodetectors 1507. FIG. 18A shows a first internal light source 1401 emitting the first light 303 during a first period, and FIG. 15B shows a second internal light source 1402 emitting the second light 304 during a second period.

In some embodiments, the interface device of the external device 101 (e.g. the inductive element 103) may be configured to receive data from the implantable device 101. In some embodiments, the received data may include one or more of an analyte measurement indicative of the amount of emission light 414 received by the internal analyte photodetector 415 and a temperature measurement indicative of a temperature within the implantable device 100. In some embodiments, the external device 101 (e.g., the PIC controller 920 of the external device 101) may be configured to calculate an analyte level using at least one or more of the received analyte measurement, the received temperature measurement, the first signal output by the first external photodetector 1107 (or the common external photodetector 1507) (e.g., after processing by the photodetector signal processing circuit 1324), and the second signal output by the second external photodetector 1108 (or the common external photodetector 1507) (e.g., after processing by the photodetector signal processing circuit 1324). In some embodiments, the external device 101 (e.g., the PIC controller 920 of the external device 101) may be additionally or alternatively configured to calculate an amount or volume of blood in a pocket around the implantable device 101 using at least one or more of the first and second signals (e.g., after processing by the photodetector signal processing circuit 1324).

Figure 19:
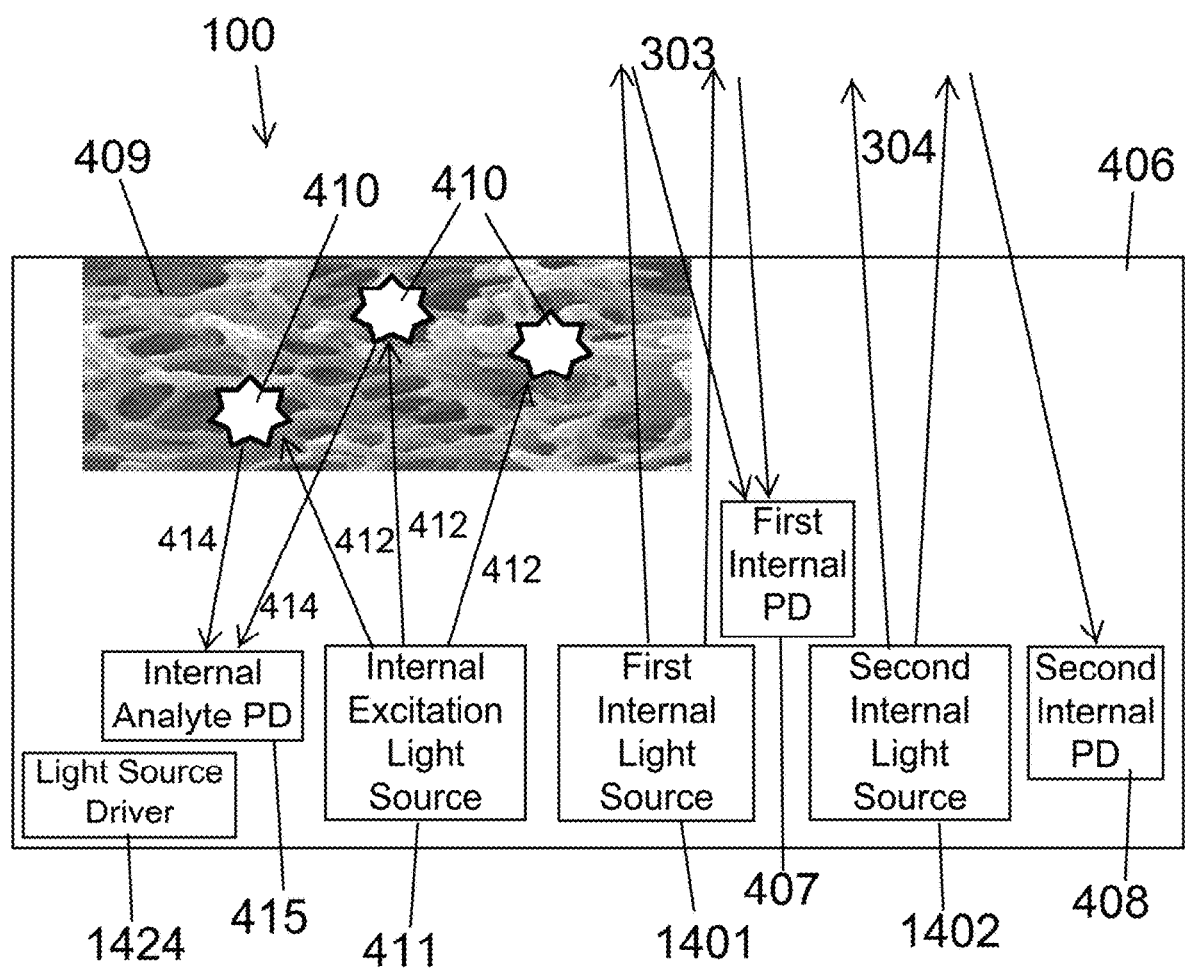
FIG. 19 is a schematic view of an implantable device including first and second internal light sources and first and second internal photodetectors and embodying aspects of the present invention.
Figure 20:
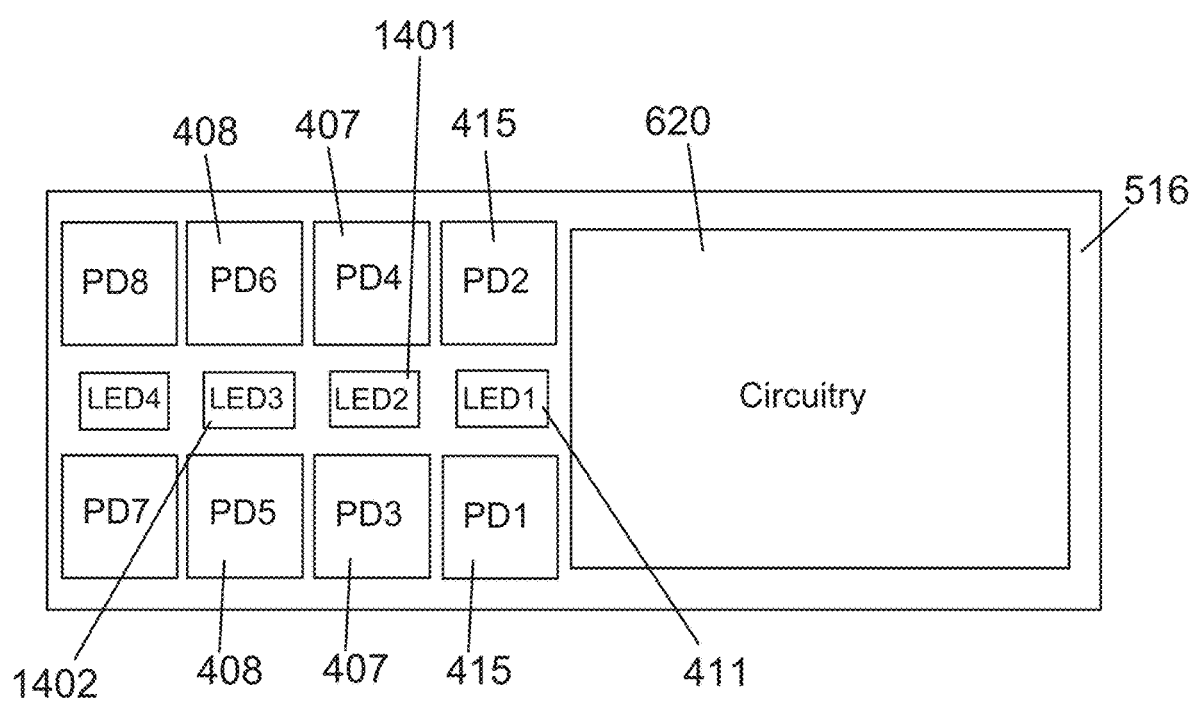
FIG. 20 is a schematic view illustrating the layout of a semiconductor substrate of an implantable device embodying aspects of the present invention.

FIG. 19 is a schematic view illustrating a non-limiting embodiment of an implantable device 100 embodying aspects of the present invention and which may be included in the system 50 shown in FIG. 1. In some embodiments, the implantable device 100 may include one or more first internal light sources 1401 configured to emit first light 303. In some embodiments, the implantable device 100 may include one or more second internal light sources 1402 configured to emit second light 304. In some embodiments, the implantable device 100 may include one or more first internal photodetectors 407 configured to output a first signal indicative of an amount of the first light 303 received by the one or more first internal photodetectors 407. In some non-limiting embodiments, the implantable device 100 may include one or more second photodetectors 408 configured to output a second signal indicative of an amount of the second light 304 received by the one or more second photodetectors 408. FIG. 20 is a schematic view illustrating the layout of the substrate 516 included in the non-limiting embodiment of the implantable device shown in FIG. 19. In some alternative embodiments, one or more of the photodetectors 407, 408, and 415 and/or one or more of the lights sources 411, 1401, and 1402 may additionally or alternatively be mounted on or fabricated in one or more additional substrates 516 of the implantable device 100.

In some embodiments, the implantable device 100 may be implanted in the tissue of a living animal. In some embodiments, one or more of the first and second internal light sources 1401 and 1402 of the implantable device 100 may emit the first light 303 and/or the second light 304, which may pass out of the implantable device 100. Some or all of the first and second light 303 and 304 may be reflected by any blood and/or clotting in a pocket 106 in the tissue 105 surrounding the implantable device 100. The reflected first and/or second light 303 and 304 may be received by one or more photodetectors of the implantable device 100.

In some embodiments, the amount of reflected first light 303 (and the first signal output by the first internal photodetector 407) may vary in accordance with the amount of blood and/or clotting in the pocket. In some non-limiting embodiments, the amount of reflected first light 303 (and the first signal output by the first internal photodetector 407) may vary in accordance with may vary in accordance with the amount of deoxygenated hemoglobin in the pocket 106. In some embodiments, the amount of reflected second light 304 (and the second signal output by the second internal photodetector 408) may vary in accordance with the amount of blood and/or clotting in the pocket 106. In some non-limiting embodiments, the amount of reflected second light 304 (and the second signal output by the second internal photodetector 408) may vary in accordance with the amount of oxygenated hemoglobin in the pocket.

In some embodiments, the amount of blood and/or clotting in a pocket 106 in the tissue 106 around the implantable device 100 may be calculated using measurements of the reflected amounts of first and second light 303 and 304. In some alternative embodiments, in addition to the implantable device 100 detecting the amount of reflected first and second light 303 and 304, the external device 101 may detect the amount of first and second light 303 and 304 that passes through pocket 106 without being reflected (e.g., using one or more first external photodetectors 1107 and one or more second external photodetectors 1108 of the external device 101). In some of these alternative embodiments, the amount of blood and/or clotting in a pocket 106 in the tissue 105 around the implantable device 100 may be calculated using measurements of the reflected amounts of first and second light 303 and 304 and measurements of amounts of first and second light 303 and 304 that pass through the pocket 106.

In some embodiments, the implantable device 100 (e.g., the measurement controller(s) and/or light source driver(s) 1424 of the implantable device 100) may be configured such that the first and second internal light sources 1401 and 1402 emit the first light 303 and second light 304 simultaneously. FIG. 19 shows an example where the first and second internal light sources 1401 and 1402 emit the first and second light 303 and 304 simultaneously. However, this is not required, and, in some alternative embodiments, the implantable device 100 (e.g., the measurement controller(s) and/or light source driver(s) 1424 of the implantable device 100) may be configured such that the first and second internal light sources 1401 and 1402 emit the first light 303 and second light 304 at different times. For example, the one or more first internal light sources 1401 may emit the first light 303 during first time periods, and the one or more second internal light sources 1402 may emit the second light 304 during second time periods that are different than the first time periods.

Figure 21A:
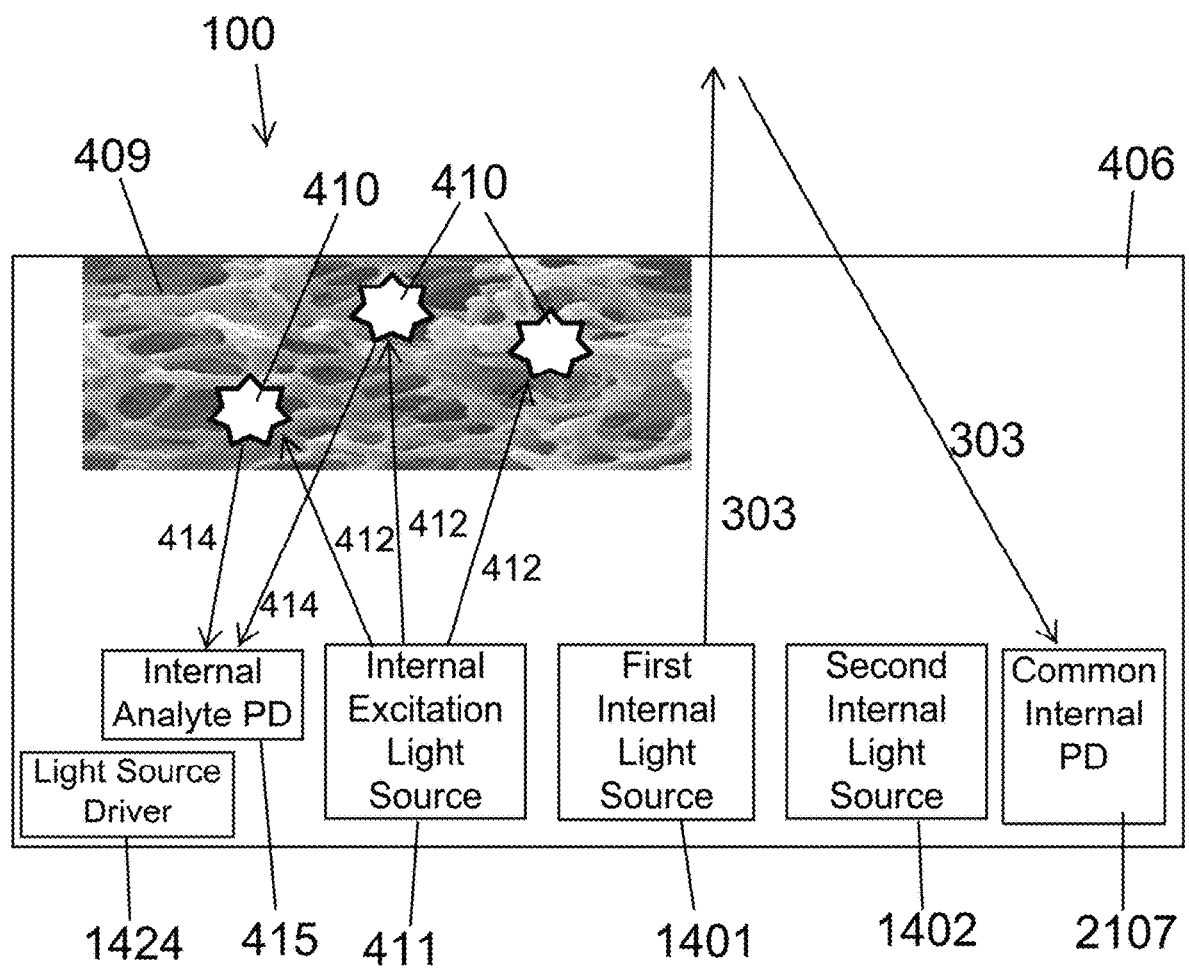
FIGS. 21A and 21B are schematic views of an implantable device including first and second internal light sources and a common photodetector and embodying aspects of the present invention.
Figure 21B:
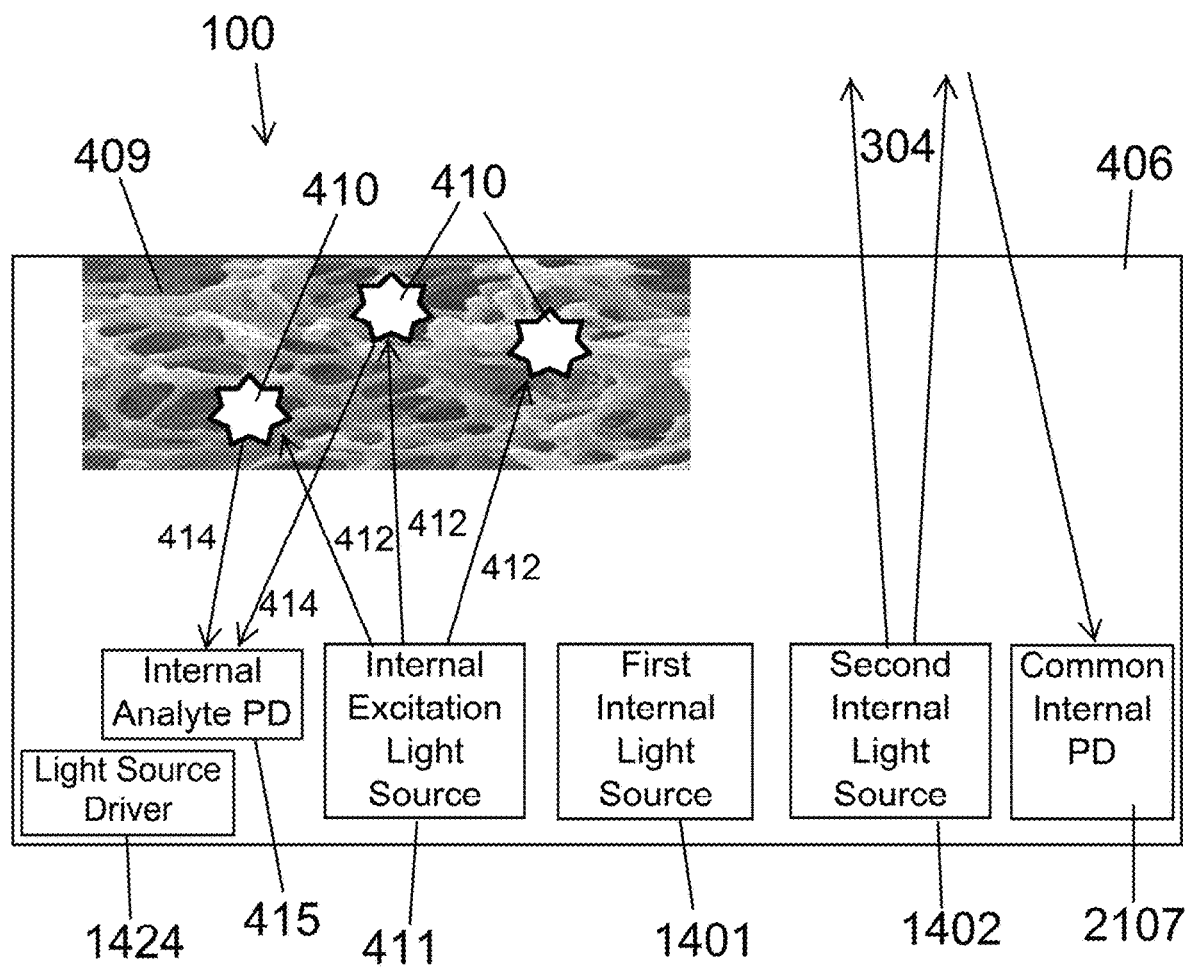

In some of the non-simultaneous alternative embodiments, as shown in FIGS. 19 and 20, the implantable device 100 may include first and second internal photodetectors 407 and 408 that output first and second signals, respectively, in accordance with the received amount of the first and second light 303 and 304, respectively. However, this is not required, and, in some other non-simultaneous alternative embodiments, as illustrated in FIGS. 21A and 21B, the implantable device 100 may instead include one or more common internal photodetectors 2107.

In some embodiments, the one or more common internal photodetectors 2107 may be configured to output a first signal during a first time period during which the one or more first internal light sources 1401 emit first light 303 and to output a second signal during a second time period during which the one or more second internal light sources 1402 emit second light 304. The first signal may be indicative of the amount of first light 303 received by the one or more common internal photodetectors 2107 during the first time period, and the second signal may be indicative of the amount of second light 304 received by the one or more common internal photodetectors 2107 during the second time period. In some non-limiting embodiments, the one or more common internal photodetectors 2107 may be configured to output the first and second signals because one or more optical filters may allow light within a wavelength range including the first and second wavelength ranges of the first and second light 303 and 304 to pass through while preventing light outside the wavelength range from reaching the one or more common photodetectors 2107. FIG. 21A shows a common internal photodetector 2107 receiving the first light 303 during a first period, and FIG. 21B shows the common internal photodetector 2107 receiving the second light 304 during a second period.

In some embodiments, the interface device of the external device 101 (e.g. the inductive element 103) may be configured to receive data from the implantable device 101. In some embodiments, the received data may include one or more of a first measurement indicative of the amount of the first light 303 received by the one or more first internal photodetectors 407 (or by the one or more common internal photodetectors 2107) of the implantable device 100, a second measurement indicative of the amount of second light 304 received by the one or more second internal photodetectors 408 (or by the one or more common internal photodetectors 2107), an analyte measurement indicative of the amount of emission light 414 received by the internal analyte photodetector 415, and a temperature measurement indicative of a temperature within the implantable device 100. In some embodiments, the external device 101 (e.g., the PIC controller 920 of the external device 101) may be configured to calculate an analyte level using at least one or more of the first, second, analyte, and temperature measurements. In some embodiments, the external device 101 (e.g., the PIC controller 920 of the external device 101) may be additionally or alternatively configured to calculate an amount or volume of blood in a pocket around the implantable device 101 using at least one or more of the first and second measurements.

Figure 22B:
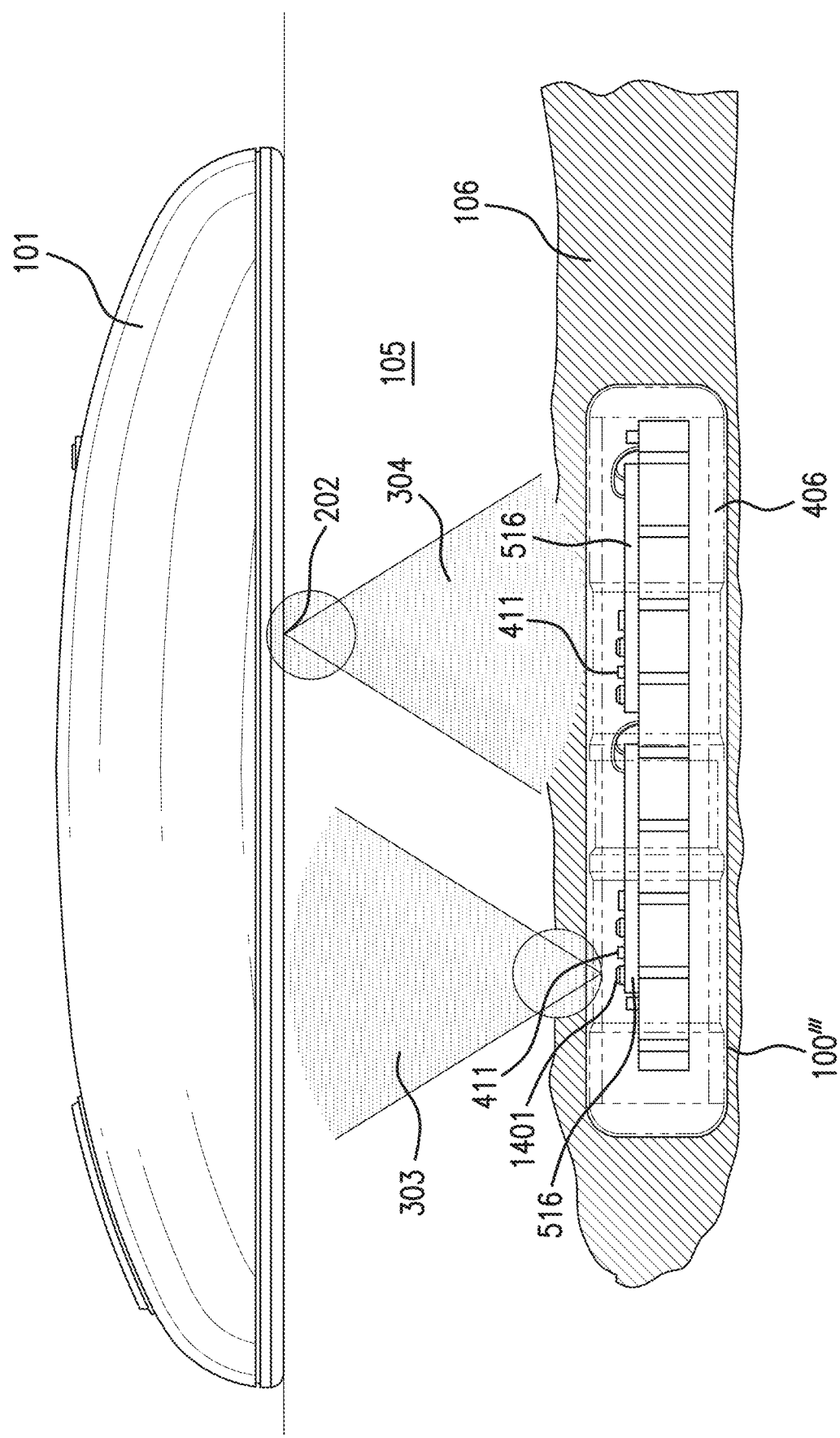

In some embodiments, as described above, one device (e.g., one of the external device 101 or the implantable device 100) may emit both the first light 303 and second light 304, and one device (e.g., the other of the external device 101 or the implantable device 100) may receive and measure both the first light 303 and second light 304. However, this is not required, and, in some alternative embodiments, the implantable device 100 may emit one of the first light 303 and the second light 304 and receive and measure the other of the first light 303 and the second light 304, and the external device 101 may emit the other of the first light 303 and the second light 304 and receive and measure the one of the first light 303 and the second light 304. For example, in some alternative embodiments, as shown in FIGS. 22A and 22B, the implantable device 100 may emit the first light 303 (e.g., using one or more first internal light sources 1401) and receive and measure the second light 304 (e.g., using one or more second internal photodetectors 408), and the external device 101 may detect the first light 304 (e.g., using one or more first external photodetectors 1107) and emit the second light 304 (e.g., using one or more second external light sources 202). In these alternative embodiments, the one or more first internal light sources 1401 that emit the first light 303 and the one or more second internal photodetectors 408 that receive and measure the second light 304 may be mounted on or fabricated in the same substrate 516 (as shown in FIG. 22A), or the one or more first internal light sources 1401 may be mounted on a substrate 516 that is separate and distinct from a substrate 516 on or in which the one or more second internal photodetectors 408 are mounted or fabricated (as shown in FIG. 22B). For another example, in some alternative embodiments, as shown in FIG. 22C, the implantable device 100 may receive and measure the first light 303 (e.g., using one or more first internal photodetectors 407) and emit the second light 304 (e.g., using one or more second internal light sources 1402), and the external device 101 may emit the first light 304 (e.g., using one or more first external light sources 201) and receive and measure the second light 304 (e.g., using one or more second external photodetectors 1108).

Figure 23:
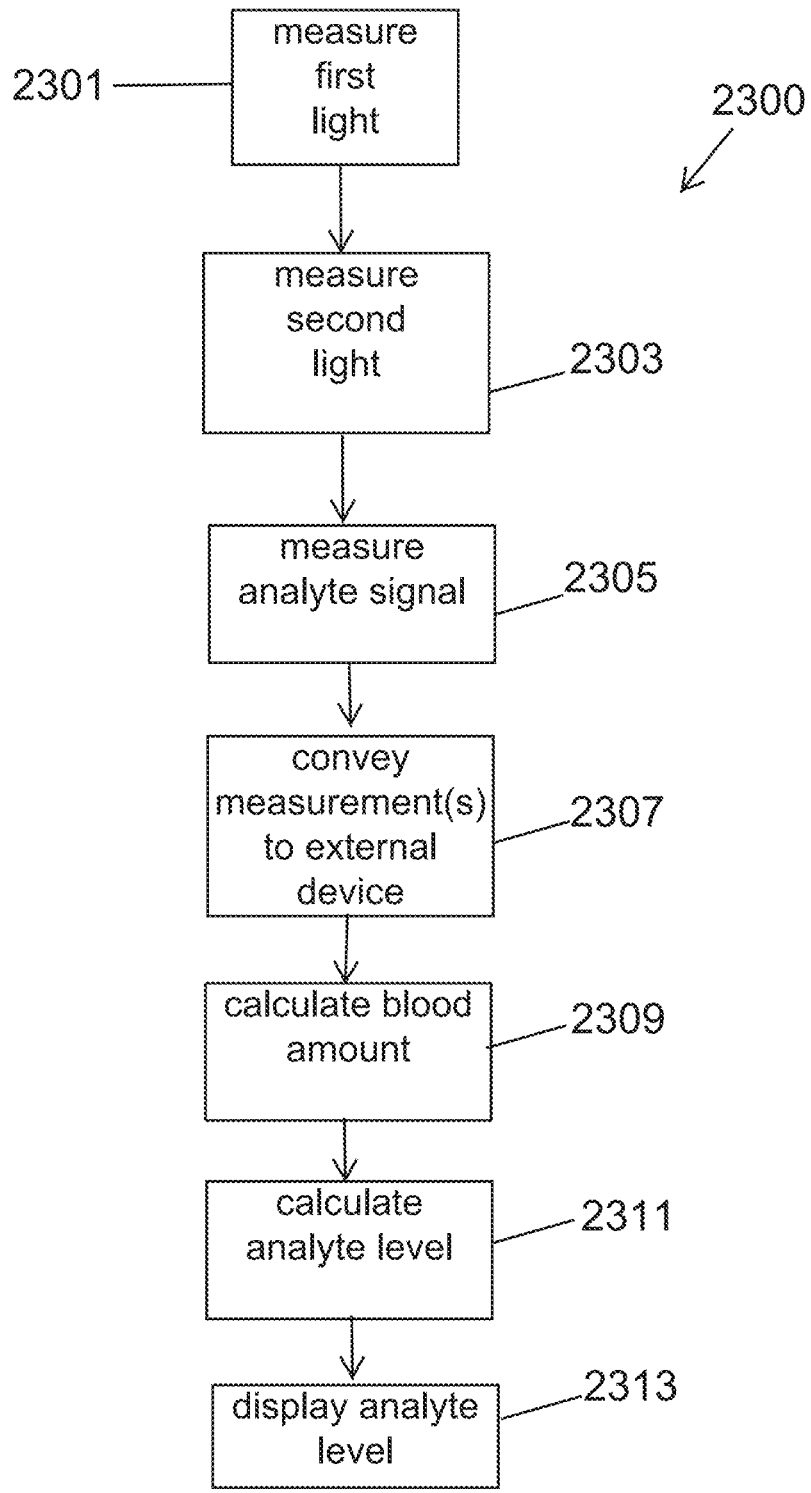
FIG. 23 is a flow chart illustrating a process for calculating an amount of blood and/or clotting surrounding an implantable device and an analyte level embodying aspects of the present invention.

FIG. 23 illustrates non-limiting embodiment of a process 2300 that may be performed by the system 50. In some embodiments, the process 2300 may measure an amount or volume of blood and/or clotting in a pocket surrounding an implantable medical device 101. In some embodiments, the process 2300 may compensate for the effect of the measured amount or volume of blood and/or clotting on when calculating an analyte level.

In some embodiments, the process 2300 may include a step 2301 in which the analyte monitoring system 50 measures an amount of a first light 303. In some embodiments, the first light 303 may be emitted by one or more first external light sources 201 (see, e.g., FIGS. 2, 3, 7G, 8, 9, and 22C) or one or more first internal light sources 1401 (see, e.g., FIGS. 14A-14C and 18A-22B). In some embodiments, the first light 303 may be measured by one or more first photodetectors, which may output a first signal in accordance with an amount of first light 303 received by the one or more first photodetectors. In some non-limiting embodiments, the one or more first photodetectors may include one or more first internal photodetectors 407 (see FIGS. 4, 5B, 6, 7E, 19, and 20), one or more common internal photodetectors 1007 or 2107 (see FIGS. 10A-10B and 21A-21B), one or more first external photodetectors 1107 (see FIGS. 11-13), or one or more common external photodetectors 1507 (see FIGS. 15-17).

In some embodiments, the process 2300 may include a step 2303 in which the analyte monitoring system 50 measures an amount of a second light 304. In some embodiments, the second light 304 may be emitted by one or more second external light sources 202 (see FIGS. 2, 3, 7G, 8, 9, 22A, and 22B) or one or more second internal light sources 1402 (see FIGS. 14A-14C, 18A-21B, and 22C). In some embodiments, the second light 304 may be measured by one or more second photodetectors, which may output a second signal in accordance with an amount of second light 304 received by the one or more second photodetectors. In some non-limiting embodiments, the one or more second photodetectors may include one or more second internal photodetectors 408 (see FIGS. 4, 5B, 6, 7E, 19, and 20), one or more common internal photodetectors 1007 or 2107 (see FIGS. 10A-10B and 21A-21B), one or more second external photodetectors 1108 (see FIGS. 11-13), or one or more common external photodetectors 1507 (see FIGS. 15-17).

In some embodiments, the process 2300 may include a step 2305 in which the analyte monitoring system 50 measures an analyte signal. In some embodiments, the step 2305 may include the implantable device 100 using one or more sensing elements to detect one or more detectable properties of the indicator element 409 of the implantable device 100. In some embodiments, the one or more sensing elements may output an analyte signal indicative of the amount or concentration of the analyte in the medium within the living animal. In some embodiments, the step 2305 may include the implantable device 100 using one or more internal excitation light sources 411 to emit excitation light 412 to the indicator element 409. In some embodiments, the analyte indicator 410 of the indicator element 409 may receive the excitation light 412 and emit emission light 414. In some embodiments, one or more internal analyte photodetectors 415 may receive the emission light 414 and generate an analyte measurement signal based on the amount of emission light 414 received by the internal analyte photodetector 224.

In some embodiments, one or more of steps 2301, 2303, and 2305 may be performed simultaneously. In some alternative embodiments, one or more of steps 2301, 2303, and 2305 may be performed sequentially (in any order).

In some embodiments, the process 2300 may include a step 2307 in which the implantable device 100 conveys one or more of a first measurement indicative of the amount of the first light 303 received by the first photodetector, a second measurement indicative of the amount of the second light 304 received by the second photodetector, and an analyte measurement indicative of the amount of emission light 414 received by the internal analyte photodetector 415. In some embodiments, in step 2307, the external device 101 may receive one or more of the first measurement, second measurement, and analyte measurement. In some non-limiting embodiments in which one or more of the first and second photodetectors is an external photodetector, the step 2307 may not include convey and receiving one or more of the first and second measurements. In some embodiments, the implantable device 100 may convey (and the external device 101) the first, second, and analyte measurements after the completion of steps 2301, 2303, and 2305 are completed. However, this is not required, and, in some alternative embodiments, one or more of the first, second, and analyte measurements may be conveyed and received individually (e.g., after the completion of each of steps 2301, 2303, and 2305).

In some embodiments, the process 2300 may include a step 2309 in which the system 50 (e.g., the PIC controller 920 of the external device 101) calculates an amount or volume of blood and/or clotting in a pocket (e.g., pocket 106 of FIG. 1B) around the implantable device 101 based at least on one or more of the first and second measurements. In some embodiments, in step 2309 the system 50 (e.g., the PIC controller 920 of the external device 101) may generate a photoplethysmogram using one or more of the first and second measurements.

In some embodiments, the process 2300 may include a step 2311 in which the system 50 (e.g., the PIC controller 920 of the external device 101) calculates an analyte level using at least the analyte measurement and one or more of the first and second measurements. In some non-limiting embodiments, the system 50 may compensate for the calculated amount or volume of blood and/or clotting in the pocket when calculating the analyte level.

In some embodiments, the process 2300 may include a step 2313 in which the system 50 displays one or more of the calculated analyte level, the calculated amount or volume of blood and/or clotting in the pocket, and the photoplethysmogram. In some embodiments, in step 2313, the external device 101 may display the analyte level, calculated amount of blood and/or clotting, and/or photoplethysmogram on a display of the external device 101. In some embodiments, in step 2313, the external device 101 may additionally or alternatively convey one or more of the calculated analyte level, the calculated amount or volume of blood and/or clotting, and the generated photoplethysmogram to the display device 107, and the display device 107 may additionally or alternatively display one or more of the calculated analyte level, the calculated amount or volume of blood and/or clotting in the pocket, and the generated photoplethysmogram.

In some embodiments, the system 50 (e.g., the PIC controller 920 of the external device 101) may use the calculated amount or volume of blood and/or clotting in the pocket for one or more of (i) compensation of signal dip, (ii) sensing blood with multiple optical measurements geometries (inside-out, outside-in), (iii) sensing blood oxygenation for predicting the local blood dynamics, (iv) sensing blood oxygenation for better compensation of signal dip, (v) sensing hemodynamics (e.g., heart rate and/or oxygenation) for patient medical information, (vi) sensing hemodynamics for more accurate lag compensation, and (vii) anesthesia applications (e.g., an implantable oxygenation sensor for anesthesia applications).

In some embodiments, the external device 101 may perform a calibration to account for changes that occur when the external device 101 is moved relative to the implantable device 100. In some embodiments, the external device 101 may move relative to the implantable device 100 each time the external device 101 is removed and placed back on the user's skin. For instance, a user may remove the external device 101 (e.g., while swimming and/or to recharge the external device 101) and then place the external device 101 back on the skin at a later time. In some embodiments, movement of the external device 101 relative to the implantable device 100 may change the amounts of the first and second lights 303 and 304 received by the photodetectors.

In some embodiments, the calibration may include taking one or more initial dynamic light measurements and then adjusting one or more subsequent dynamic light measurements to have a dynamic range and/or offset similar to the dynamic range and/or offset of the initial dynamic light measurements. In some embodiments, the dynamic light measurements may be accomplished using two or more time slots of a measurement sequence to measure the light at different times. In some non-limiting embodiments, the initial and subsequent dynamic light measurements may include dynamic measurements of one or more of the first and second light 303 and 304 emitted from one of the implantable and external devices 100 and 101 and received by the other of the implantable and external devices 100 and 101. In some non-limiting embodiments, the initial and subsequent dynamic light measurements may additionally or alternatively include dynamic measurements of the reflected intensity of one or more of the first and second light 303 and 304 (see FIGS. 19, 21A, and 21B). In some non-limiting embodiments, the calibration may additionally or alternatively account for changes with respect to the one or more indicator elements 409 (e.g., changes to the opacity of the one or more indicator elements 409, which may affect the amount of the first and second lights 303 and 304 that passes through the one or more indicator elements 409).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:
1. A system comprising:
 a first light source configured to emit light over a first wavelength range;

a first photodetector configured to output a first signal indicative of an amount of the first light received by the first photodetector;

an implantable device comprising one of the first light source and the first photodetector; and an external device comprising:
the other of the first light source and the first photodetector; and
a controller configured to calculate an amount of blood in a pocket around the implantable device using at least a measurement of the first signal.

2. The system of claim 1, further comprising a second light source configured to emit light over a second wavelength range, which is different than the first wavelength range;

wherein one of the implantable device and the external device comprises the second light source.

3. The system of claim 2, wherein the first photodetector is a common photodetector configured to output the first signal indicative of the amount of the first light received by the common photodetector and to output a second signal indicative of an amount of the second light received by the common photodetector.

4. The system of claim 3, wherein the controller is configured to calculate the amount of blood in the pocket around the implantable device using at least the measurement of the first signal and a measurement of the second signal.

5. The system of claim 2, further comprising a second photodetector configured to output a second signal indicative of an amount of the second light received by the second photodetector, wherein the first and second photodetectors are different photodetectors.

6. The system of claim 5, wherein one of the implantable device and the external device comprises the first and second light sources, and the other of the implantable device and the external device comprises the first and second photodetectors.

7. The system of claim 5, wherein one of the implantable device and the external device comprises the first light source and the second photodetector, and the other of the implantable device and the external device comprises the second light source and the first photodetector.

8. The system of claim 2, wherein the first wavelength ranges includes red light, and the second wavelength range includes infrared light.

9. The system of claim 2, wherein the controller is configured to cause the first and second light sources to emit the first light and second light simultaneously.

10. The system of claim 2, wherein the controller is configured to cause the first light source to emit the first light during a first time period and to cause the second light source to emit the second light during a second time period, and the first and second time periods are different time periods.

11. The system of claim 1, wherein the implantable device further comprises:
an excitation light source configured to emit excitation light over an excitation wavelength range;
an analyte indicator configured to receive the excitation light and emit emission light over an emission light wavelength range, wherein the amount of emission light varies in accordance with an amount or concentration of an analyte in a medium within a living animal; and an analyte photodetector configured to output an analyte signal indicative of an amount of the emission light received by the analyte photodetector.

12. The system of claim 11, wherein the controller is configured to calculate an analyte level based on at least a measurement of analyte signal and one or more of a measurement of the first signal and a measurement of the second signal.

13. The system of claim 12, wherein the controller is further configured to compensate for the calculated amount of blood in the pocket when calculating the analyte level.

14. The system of claim 11, wherein the emission wavelength range includes fluorescent light, the first wavelength range includes red light, and the second wavelength range includes infrared light.

15. A method comprising:
using a first light source to emit light over a first wavelength range;
using a first photodetector to output a first signal indicative of an amount of the first light received by the first photodetector; and
using a controller of an external device to calculate an amount of blood in a pocket around the implantable device using at least a measurement of the first signal;
wherein an implantable device comprises one of the first light source and the first photodetector, and the external device comprises the other of the first light source and the first photodetector.

16. The method of claim 15, further comprising using a second light source to emit light over a second wavelength range, which is different than the first wavelength range;
wherein one of the implantable device and the external device comprises the second light source.

17. The method of claim 16, using the first photodetector to output the first signal indicative of the amount of the first light received by the first photodetector and to output a second signal indicative of an amount of the second light received by the first photodetector.

18. The method of claim 17, wherein the controller calculates the amount of blood in the pocket around the implantable device using at least the measurement of the first signal and a measurement of the second signal.

19. The method of claim 16, further comprising using a second photodetector to output a second signal indicative of an amount of the second light received by the second photodetector, wherein the first and second photodetectors are different photodetectors.

20. The method of claim 15, further comprising:
using an excitation light source of the implantable device to emit excitation light over an excitation wavelength range;
using an analyte indicator of the implantable device to receive the excitation light and emit emission light over an emission light wavelength range, wherein the amount of emission light varies in accordance with an amount or concentration of an analyte in a medium within a living animal; and
using an analyte photodetector of the implantable device to output an analyte signal indicative of an amount of the emission light received by the analyte photodetector.

21. The method of claim 20, further comprising using the controller of the external device to calculate an analyte level based on at least a measurement of analyte signal and one or more of a measurement of the first signal and a measurement of the second signal.

22. The method of claim 21, wherein calculating the analyte level comprises compensating for the calculated amount of blood in the pocket.

* * * * *